United States Patent
Bonrath et al.

(10) Patent No.: US 9,573,872 B2
(45) Date of Patent: *Feb. 21, 2017

(54) USING MIXTURES OF E/Z ISOMERS TO OBTAIN QUANTITATIVELY SPECIFIC PRODUCTS BY COMBINING ASYMMETRIC HYDROGENATION AND ISOMERIZATION

(71) Applicant: DSM IP ASSETS B.V., Heerlen (NL)

(72) Inventors: Werner Bonrath, Kaiseraugst (CH); Thomas Netscher, Kaiseraugst (CH); Jonathan Alan Medlock, Kaiseraugst (CH); René Tobias Stemmler, Kaiseraugst (CH); Gerardus Karel Maria Verzijl, Kaiseraugst (CH); Andreas Hendrikus Maria De Vries, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/652,362

(22) PCT Filed: Dec. 18, 2013

(86) PCT No.: PCT/EP2013/077246
§ 371 (c)(1),
(2) Date: Jun. 15, 2015

(87) PCT Pub. No.: WO2014/096107
PCT Pub. Date: Jun. 26, 2014

(65) Prior Publication Data
US 2016/0185702 A1    Jun. 30, 2016

(30) Foreign Application Priority Data

Dec. 18, 2012  (EP) .................... 12197857

(51) Int. Cl.
*C07C 45/62*  (2006.01)
*C07C 45/67*  (2006.01)

(52) U.S. Cl.
CPC .......... *C07C 45/67* (2013.01); *C07C 45/62* (2013.01); *C07B 2200/07* (2013.01)

(58) Field of Classification Search
CPC ...... C07C 45/62; C07C 45/67; C07B 2200/00
USPC .......................................... 568/384; 549/369
See application file for complete search history.

(56) References Cited

U.S. PATENT DOCUMENTS 5,908,957 A    6/1999  Wildermann

FOREIGN PATENT DOCUMENTS

| CN | 1201787 | 12/1998 |
|---|---|---|
| CN | 1449393 | 10/2003 |
| EP | 1 179 531 | 2/2002 |
| FR | 2 302 996 | 10/1976 |
| WO | WO 2006/066863 | 6/2006 |

OTHER PUBLICATIONS

International Search Report for PCT/EP2013/077246, mailed Mar. 11, 2014.
Justicia, et al., "Palladium mediated C-H activation in the field of terpenoids: synthesis of rostratone", *Tetrahedron Letters*, May 24, 2004, vol. 45, No. 22, pp. 4293-4296.
Matsubara, et al., "Synthesis of New Acetals and their Derivatives from Terpene Aldehyde and Alcohol", Yuki Gosei Kagaku Kyokaishi, *Journal of Synthetic Organic Chemistry*, Japan, vol. 28, No. 8, Jan. 1, 1970, pp. 1679-1682.
Gopalan et al., "Polyene cyclizations using mercury (II) triflate-N,N-dimethylaniline complex—participation by internal nucleophiles", *Tetrahedron Letters*, Mar. 1, 1992, vol. 33 No. 13, pp. 1679-1682.
Takeshi et al., "Preparation of 4,6-0-alkylidene-.alpha.,.alpha.-trehalose as surfactants", XP002697173, retrieved May 14, 2013, 2 pages.
Kubota et al., "Novel synthetic reactions using bis(2,2,2-trifluoroethoxy)triphenylphosphorane", *The Journal of Organic Chemistry*, Dec. 1, 1980, vol. 45, No. 25, pp. 5052-5057.
CN Appln. No. 201380065928.1, Official Action (Mar. 22, 2016).
RN 187262-19-7, ACS (STN-Register), Mar. 19, 1997.
Carey et al, *Advanced Organic Chemistry*, Part B, Reaction and Synthesis, Plenum Press, New York, pp. 323-324 (Jan. 31, 1986).
Smidt et al, "Enantioselective Hydrogenation of Alenes with Iridium-PHOX Catalysts: A Kinetic Study of Anion Effects", Chem. Eur.J, 2004, 10, 4685-4693.

*Primary Examiner* — Sikarl Witherspoon
(74) *Attorney, Agent, or Firm* — Nixon & Vanderhye P.C.

(57) ABSTRACT

The present invention relates to a process of manufacturing compound having stereogenic centers from a mixture of E/Z isomers of unsaturated compounds having prochiral double bonds. The hydrogenation product has a specific desired configuration at the stereogenic centers. The process involves an asymmetric hydrogenation and an isomerization step. The process is very advantageous in that it forms the desired chiral product from a mixture of stereoisomers of the starting product in an efficient way.

17 Claims, 5 Drawing Sheets

Figure 1A:
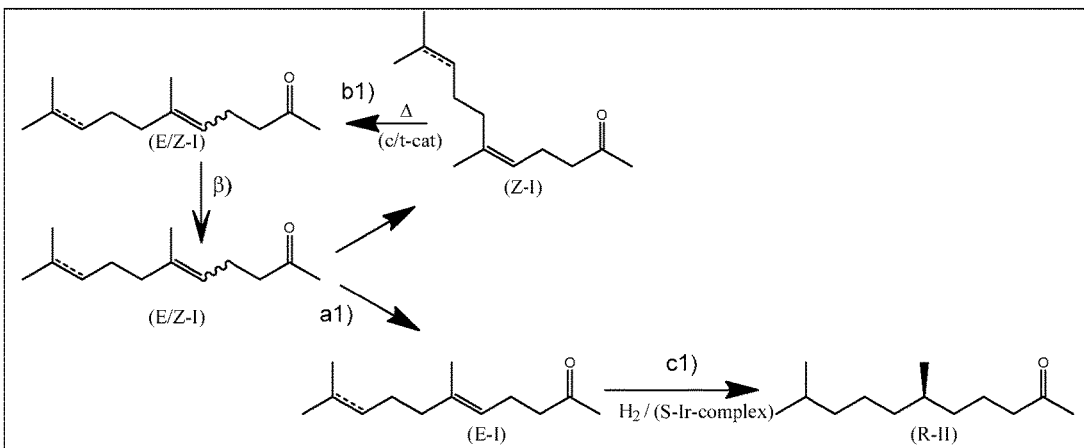

USING MIXTURES OF E/Z ISOMERS TO OBTAIN QUANTITATIVELY SPECIFIC PRODUCTS BY COMBINING ASYMMETRIC HYDROGENATION AND ISOMERIZATION

This application is the U.S. national phase of International Application No. PCT/EP2013/077246 filed 18 Dec. 2013, which designated the U.S. and claims priority to EP Patent Application No. 12197857.1 filed 18 Dec. 2012, the entire contents of each of which are hereby incorporated by reference.

TECHNICAL FIELD

The present invention relates to field of asymmetric hydrogenation and the synthesis of chiral ketones, aldehydes, acetals and ketals.

BACKGROUND OF THE INVENTION

Chiral ketones and aldehydes are very important products or intermediates for the synthesis of compounds in the fields of flavours and fragrances or pharmaceutical products and vitamins.

These products have stereogenic centres which makes their properties very unique.

One possibility of creating stereogenic carbon centres is addition of compounds, particularly of molecular hydrogen, to prochiral carbon-carbon double bonds of suitable starting materials.

Classic chemical reactions mainly result in mixtures of the stereoisomers at said stereogenic centres and require the use of expensive separation processes.

Therefore for a long time there has been a large demand for highly stereoselective reactions leading to specific stereogenic configurations.

WO 2006/066863 A1 discloses an asymmetric hydrogenation of alkenes to yield specific configurations of the stereogenic centres being formed by the hydrogenation.

However, technically alkenes very often are mixtures of E and Z isomers.

It is known that carbon-carbon double bonds of alkenes can be isomerized. Transition metal derivatives as well as sulphur compounds such as sulfides or disulfides or monomercaptanes are known to isomerize farnesol as described for example in DE 25 57 837.

U.S. Pat. No. 4,028,385 discloses transition metal catalysts as well as organic sulphur compounds such as sulfides or disulfides or monomercaptanes for the isomerization isomerize of farnesylacetic acids and esters as well as rectification of the corresponding stereoisomeric mixtures.

However, the disclosure of isomerization in these documents has not been in the context of asymmetric hydrogenations.

SUMMARY OF THE INVENTION

Therefore, the problem to be solved by the present invention is to offer a process which allows using mixtures of E/Z isomers of unsaturated compounds having prochiral carbon-carbon double bonds to yield a hydrogenated product having the desired configuration at the stereogenic centre being formed by the hydrogenation.

Surprisingly, it has been shown that this problem can be solved by the process according to claim 1.

In this process mixtures of isomers can be used and all isomers can be converted to the desired product.

It has been shown that particularly the hydrogenation of acetals and ketals are very effective and offer a much better efficiency of the chiral complexes used in the asymmetric hydrogenations.

Further aspects of the invention are subject of further independent claims. Particularly preferred embodiments are subject of dependent claims.

DETAILED DESCRIPTION OF THE INVENTION

In a first aspect the present invention relates to a process of manufacturing compound of formula (I-A) or (I-B) or an acetal or a ketal thereof from a mixture of E/Z isomers of compound of formula (I) or (II) or an acetal or a ketal thereof

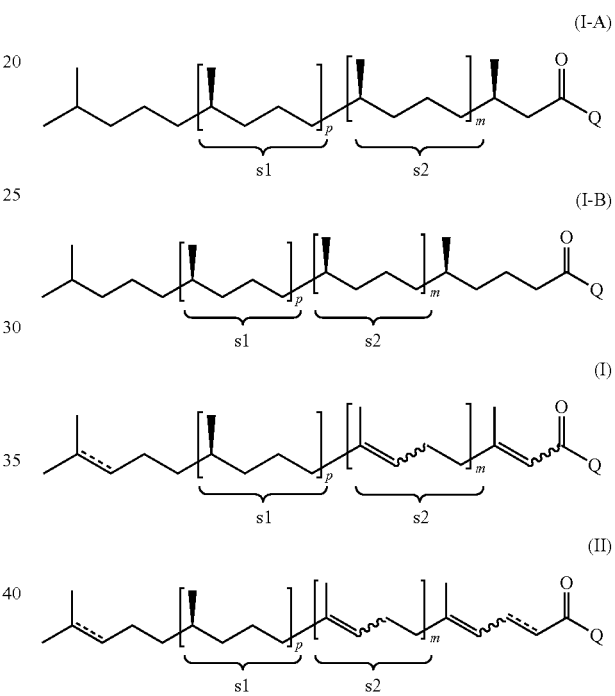

wherein Q stands for H or $CH_3$ and m and p stand independently from each other for a value of 0 to 3 with the proviso that the sum of m and p is 0 to 3, and where a wavy line represents a carbon-carbon bond which is linked to the adjacent carbon-carbon double bond so as to have said carbon-carbon double bond either in the Z or in the E-configuration and where the substructures in formula (I) and (II) represented by s1 and s2 can be in any sequence;

and wherein the double bond having dotted lines ( ═══ ) in formula (I) or (II) represent either a single carbon-carbon bond or a double carbon-carbon bond;

comprising the steps either a1) separating an isomer having E-configuration from the mixture of E/Z isomers of compound of formula (I) or (II) or the acetal or ketal thereof;

and b1) submitting the isomers having the Z-configuration of compound of formula (I) or (II) or the acetal or ketal thereof to cis/trans isomerisation and adding the isomerization product to the mixture of isomers of compound of formula (I) or (II) or the acetal or ketal thereof;

and c1) submitting the separated isomer having the E-configuration of compound of formula (I) or (II) or the acetal or ketal thereof to hydrogenation by molecular hydrogen in the presence of a chiral iridium complex of formula (III) having the S-configuration at the stereogenic centre indicated by *;

or a2) separating an isomer having Z-configuration from the mixture of E/Z isomers of compound of formula (I) or (II) or the acetal or ketal thereof;

and b2) submitting the isomers having the E-configuration of compound of formula (I) or (II) or the acetal or ketal thereof to cis/trans isomerisation and adding the isomerization product to the mixture of isomers of compound of formula (I) or (II) or the acetal or ketal thereof;

and c2) submitting the separated isomer having the Z-configuration of compound of formula (I) or (II) or the acetal or ketal thereof to hydrogenation by molecular hydrogen in the presence of a chiral iridium complex of formula (III) having the R-configuration at the stereogenic centre indicated by *;

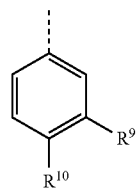

(III)

wherein n is 1 or 2 or 3, preferred 1 or 2;

$X^1$ and $X^2$ are independently from each other hydrogen atoms, $C_{1-4}$-alkyl, $C_{5-7}$-cycloalkyl, adamantyl, phenyl (optionally substituted with one to three $C_{1-5}$-alkyl, $C_{1-4}$-alkoxy, $C_{1-4}$-perfluoroalkyl groups and/or one to five halogen atoms)), benzyl, 1-naphthyl, 2-naphthyl, 2-furyl or ferrocenyl;

$Z^1$ and $Z^2$ are independently from each other hydrogen atoms, $C_{1-5}$-alkyl or $C_{1-5}$-alkoxy groups;

or $Z^1$ and $Z^2$ stand together for a bridging group forming a 5 to 6 membered ring;

$Y^\ominus$ is an anion, particularly selected from the group consisting of halide, $PF_6^-$, $SbF_6^-$, tetra(3,5-bis(trifluoromethyl)phenyl)borate($BAr_F^-$), $BF_4^-$, perfluorinated sulfonates, preferably $F_3C$—$SO_3^-$ or $F_9C_4$—$SO_3^-$; $ClO_4^-$, $Al(OC_6F_5)_4^-$, $Al(OC(CF_3)_3)_4^-$, $N(SO_2CF_3)_2^-N(SO_2C_4F_9)_2^-$ and $B(C_6F_5)_4^-$;

$R^1$ represents either phenyl or o-tolyl or m-tolyl or p-tolyl or a group of formula (IVa) or (IVb) or (IVc)

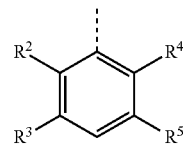

(IVa)

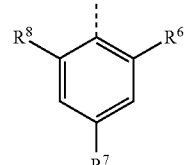

(IVb)

(IVc)

wherein $R^2$ and $R^3$ represent either both H or a $C_1$-$C_4$-alkyl group or a halogenated $C_1$-$C_4$-alkyl group or represent a divalent group forming together a 6-membered cycloaliphatic or an aromatic ring which optionally is substituted by halogens atoms or by $C_1$-$C_4$-alkyl groups or by $C_1$-$C_4$-alkoxy groups $R^4$ and $R^5$ represent either both H or a $C_1$-$C_4$-alkyl group or a halogenated $C_1$-$C_4$-alkyl group or a divalent group forming together a 6-membered cycloaliphatic or an aromatic ring which optionally is substituted by halogens atoms or by $C_1$-$C_4$-alkyl groups or by $C_1$-$C_4$-alkoxy groups;

$R^6$ and $R^7$ and $R^8$ represent each a $C_1$-$C_4$-alkyl group or a halogenated $C_1$-$C_4$-alkyl group;

$R^9$ and $R^{10}$ represent either both H or a $C_1$-$C_4$-alkyl group or a halogenated $C_1$-$C_4$-alkyl group or a divalent group forming together a 6-membered cycloaliphatic or an aromatic ring which optionally is substituted by halogens atoms or by $C_1$-$C_4$-alkyl groups or by $C_1$-$C_4$-alkoxy groups;

and wherein * represents a stereogenic centre of the complex of formula (III).

The sum of m and p is preferably 0 to 2, particularly 0 or 1.

The term "unsaturated ketone or aldehyde" or "unsaturated acetal or ketal" relates in the whole document to compounds of formula (I) or (II) or to the preferred embodiments thereof.

The term "independently from each other" in this document means, in the context of substituents, moieties, or groups, that identically designated substituents, moieties, or groups can occur simultaneously with a different meaning in the same molecule.

A "$C_{x-y}$-alkyl" group is an alkyl group comprising x to y carbon atoms, i.e., for example, a $C_{1-3}$-alkyl group is an alkyl group comprising 1 to 3 carbon atoms. The alkyl group can be linear or branched. For example —CH(CH$_3$)—CH$_2$—CH$_3$ is considered as a $C_4$-alkyl group.

A "$C_{x-y}$-alkylene" group is a $C_{x-y}$-alkylene group comprising x to y carbon atoms, i.e., for example $C_2$-$C_6$ alkylene group is an alkyl group comprising 2 to 6 carbon atoms. The alkylene group can be linear or branched. For example the group —CH(CH₃)—CH₂— is considered as a $C_3$-alkylene group.

A "phenolic alcohol" means in this document an alcohol which has a hydroxyl group which is bound directly to an aromatic group.

The term "stereogenic centre" as used in this document is an atom, bearing groups such that interchanging of any two of the groups leads to a stereoisomer. Stereoisomers are isomeric molecules that have the same molecular formula and sequence of bonded atoms (constitution), but that differ in the three-dimensional orientations of their atoms in space.

Cis/trans isomers are configurational isomers having different orientation at the double bond. In this document the term "cis" is equivalently used for "Z" and vice versa as well as "trans" for "E" and vice versa. Therefore, for example the term "cis/trans isomerization catalyst" is equivalent to the term "E/Z isomerization catalyst".

The terms "E/Z", "cis/trans" and "R/S" denote mixtures of E and Z, of cis and trans, and of R and S, respectively.

In case identical labels for symbols or groups are present in several formulae, in the present document, the definition of said group or symbol made in the context of one specific formula applies also to other formulae which comprises said same label.

In the present document any single dotted line represents the bond by which a substituent is bound to the rest of a molecule.

"Assay yield" of an asymmetric hydrogenation is in the present application the molar ratio of number of molecules of completely saturated ketones or aldehydes or ketals or acetals to the number of molecules of unsaturated ketones or aldehydes or ketals or acetals being submitted to the hydrogenation.

The process of manufacturing compound of formula (I-A) or (I-B) or an acetal or a ketal thereof uses a mixture of E/Z isomers of compound of formula (I) or (II) or an acetal or a ketal thereof as staring material.

The compound of formula (I) or (II) or the acetals or ketals thereof have prochiral carbon-carbon double bonds.

Particularly preferred is compounds of (II), particularly being selected from the group consisting of 6,10-dimethylundeca-3,5,9-trien-2-one, 6,10-dimethylundeca-5,9-dien-2-one, 6,10-dimethylundec-5-en-2-one, 6,10-dimethylundec-3-en-2-one, 6,10-dimethylundec-3,5-diene-2-one, 6,10,14-trimethylpentadeca-5,9,13-trien-2-one, 6,10,14-trimethylpentadeca-5,9-dien-2-one, 6,10,14-trimethylpentadec-5-en-2-one and (R)-6,10,14-trimethylpentadec-5-en-2-one as well as all their possible E/Z-isomers.

Most preferably the compound of formula (I) or (II) is selected from the group consisting of 3,7-dimethyloct-6-enal, 3,7-dimethylocta-2,6-dienal, 3,7-dimethyloct-2-enal, 6,10-dimethylundeca-3,5,9-trien-2-one, 6,10-dimethylundeca-5,9-dien-2-one, 6,10-dimethylundec-5-en-2-one, 6,10-dimethylundec-3-en-2-one, 6,10-dimethylundec-3,5-diene-2-one, 6,10,14-trimethylpentadeca-5,9,13-trien-2-one, 6,10,14-trimethylpentadeca-5,9-dien-2-one, 6,10,14-trimethylpentadec-5-en-2-one and (R)-6,10,14-trimethylpentadec-5-en-2-one as well as all their possible E/Z-isomers.

Most preferably the compound of formula (I) or (II) is a ketone.

Acetal/Ketal Formation

The formation of a ketal from a ketone, or of an acetal from an aldehyde, per se, is known to the person skilled in the art.

The ketal or acetal of compound of formula (I) or (II) can be preferably formed from the above mentioned compound of formula (I) or (II) and an alcohol.

It is known to the person skilled in the art that there are alternative routes of synthesis for acetal or ketals. In principle, the ketal and acetals can also be formed by treating a ketone or an aldehyde with ortho-esters or by trans-ketalization such as disclosed for example in Pério et al., *Tetrahedron Lett.*, 1997, 38 (45), 7867-7870, or in Lorette, *J. Org. Chem.* 1960, 25, 521-525, the entire content of both is hereby incorporated by reference.

Preferably the ketal or acetal is formed from the above mentioned compound of formula (I) or (II) and an alcohol.

The alcohol used for the ketal or acetal formation can, principally, be any alcohol, i.e. the alcohol may comprise one or more hydroxyl groups. The alcohol may be a phenolic alcohol or an aliphatic or cycloaliphatic alcohol. Preferably, however, the alcohol has one hydroxyl groups (=monol) or two hydroxyl groups (=diol).

In case the alcohol has one hydroxyl group, the alcohol is preferably an alcohol which has 1 to 12 carbon atoms. Particularly, the alcohol having one hydroxyl group is selected from the group consisting of methanol, ethanol, 1-propanol, 2-propanol, 1-butanol, 2-methyl-1-propanol, 2-butanol, pentane-1-ol, 3-methylbutane-1-ol, 2-methylbutane-1-ol, 2,2-dimethylpropan-1-ol, pentane-3-ol, pentane-2-ol, 3-methylbutane-2-ol, 2-methylbutan-2-ol, hexane-1-ol, hexane-2-ol, hexane-3-ol, 2-methyl-1-pentanol, 3-methyl-1-pentanol, 4-methyl-1-pentanol, 3-methyl-2-pentanol, 4-methyl-2-pentanol, 2-methyl-3-pentanol, 2,2-dimethyl-1-butanol, 2,3-dimethyl-1-butanol, 3,3-dimethyl-1-butanol, 3,3-dimethyl-2-butanol, 2-ethyl-1-butanol, and all structural isomers of heptanol, octanol and halogenated $C_1$-$C_8$-alkyl alcohols, particularly 2,2,2-trifluoroethanol. Particularly suitable are primary or secondary alcohols. Preferably primary alcohols are used as alcohols with one hydroxyl group. Particularly methanol, ethanol, 1-propanol, 2-propanol, 1-butanol, 2-butanol or 2,2,2-trifluoroethanol, preferably methanol, ethanol, 1-propanol, 1-butanol or 2,2,2-trifluoroethanol, are used as alcohols with one hydroxyl group.

In another embodiment the alcohol is a diol. Preferably the diol is selected from the group consisting of ethane-1,2-diol, propane-1,2-diol, propane-1,3-diol, butane-1,4-diol, butane-1,3-diol, butane-1,2-diol, butane-2,3-diol, 2-methylpropane-1,2-diol, 2-methylpropane-1,3-diol, 2,2-dimethylpropane-1,3-diol, 1,2-dimethylpropane-1,3-diol, 3-methylpentane-2,4-diol and 2-(hydroxymethyl)-cyclohexanol, benzene-1,2-diol and cyclohexane-1,2-diols. From two cyclohexane-1,2-diols the preferred stereoisomer is syn-cyclohexane-1,2-diol (=cis-cyclohexane-1,2-diol).

The two hydroxyl group are in one embodiment bound to two adjacent carbon atoms, hence these diols are vicinal diols. Vicinal diols form a 5 membered ring in a ketal or acetal.

Particularly suitable are vicinal diols which are selected from the group consisting of ethane-1,2-diol, propane-1,2-diol, butane-1,2-diol, butane-2,3-diol, 2-methylpropane-1,2-diol, benzene-1,2-diol and syn-cyclohexane-1,2-diol, particularly ethane-1,2-diol.

Other particularly suitable are diols, in which the hydroxyl groups are separated by 3 carbon atoms, and, hence, form a very stable 6 membered ring in a ketal or acetal. Particularly suitable diols of this type are propane-1,3-diol, butane-1,3-diol, 2-methylpropane-1,3-diol, 2-methylbutane-1,3-diol, 2,2-dimethylpropane-1,3-diol, 1,2-dimethylpropane-1,3-diol, 3-methylpentane-2,4-diol and 2-(hydroxymethyl)cyclohexanol.

Preferably primary alcohols are used as diols.

In one embodiment the acetal or ketal of the compound of formula (I) or (II) is obtained by the reaction of the compound of formula (I) or (II) with an alcohol, particularly a monol or a diol, preferably an alcohol selected from the group consisting of is halogenated $C_1$-$C_8$-alkyl alcohol or which is selected from the group consisting of ethane-1,2-diol, propane-1,2-diol, propane-1,3-diol, butane-1,4-diol, butane-1,3-diol, butane-1,2-diol, butane-2,3-diol, 2-methylpropane-1,2-diol, 2-methylpropane-1,3-diol, 2,2-dimethylpropane-1,3-diol, 1,2-dimethylpropane-1,3-diol, 3-methylpentane-2,4-diol and 2-(hydroxymethyl)cyclohexanol, benzene-1,2-diol and cyclohexane-1,2-diols.

The reaction conditions and stoichiometry used for the acetal or ketal formation are known to the person skilled in the art. Particularly the acetal or ketal is formed under the influence of an acid.

The preferred ketal or acetal of formula (I) or (II) are of formula (XI) or (XII)

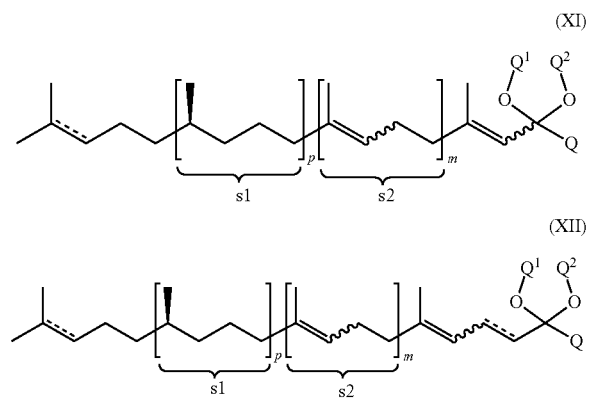

The groups and symbols in formula (XI) and (XII) have the same meaning as defined before in this document for formula (I) and (II).

$Q^1$ and $Q^2$ stand either individually both for a $C_1$-$C_{10}$ alkyl group or a halogenated $C_1$-$C_{10}$ alkyl group;

or form together a $C_2$-$C_6$ alkylene group or a $C_6$-$C_8$ cycloalkylene group.

$Q^1$ and $Q^2$ stand particularly for either a linear $C_1$-$C_{10}$ alkyl group or fluorinated linear $C_1$-$C_{10}$ alkyl group, preferably a linear $C_1$-$C_4$ alkyl group or a —$CH_2CF_3$ group or a group of formula

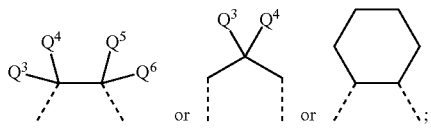

in which $Q^3$, $Q^4$, $Q^5$ and $Q^6$ are independently from each other hydrogen atoms or methyl or ethyl groups.

Preferably the ketal or the acetal of formula (XI) or (XII) are (E)-2-(4,8-dimethylnona-3,7-dien-1-yl)-2,5,5-trimethyl-1,3-dioxane, (E)-2,6-dimethyl-10,10-bis(2,2,2-trifluoroethoxy)undeca-2,6-diene, (E)-2-(4,8-dimethylnon-3-en-1-yl)-2,5,5-trimethyl-1,3-dioxane, (E)-6,10-dimethyl-2,2-bis(2,2,2-trifluoroethoxy)undec-5-ene, (E)-2,5,5-trimethyl-2-(4,8,12-trimethyltridec-3-en-1-yl)-1,3-dioxane, (R,E)-2,5,5-trimethyl-2-(4,8,12-trimethyltridec-3-en-1-yl)-1,3-dioxane, (E)-6,10,14-trimethyl-2,2-bis(2,2,2-trifluoroethoxy)pentadec-5-ene, (R,E)-6,10,14-trimethyl-2,2-bis(2,2,2-trifluoroethoxy)pentadec-5-ene, (Z)-2-(4,8-dimethylnona-3,7-dien-1-yl)-2,5,5-trimethyl-1,3-dioxane, (Z)-2,6-dimethyl-10,10-bis(2,2,2-trifluoroethoxy)undeca-2,6-diene, (Z)-2-(4,8-dimethylnon-3-en-1-yl)-2,5,5-trimethyl-1,3-dioxane, (Z)-6,10-dimethyl-2,2-bis(2,2,2-trifluoroethoxy)undec-5-ene, (Z)-2,5,5-trimethyl-2-(4,8,12-trimethyltridec-3-en-1-yl)-1,3-dioxane, (R,Z)-2,5,5-trimethyl-2-(4,8,12-trimethyltridec-3-en-1-yl)-1,3-dioxane, 2,5,5-trimethyl-2-((3E,7E)-4,8,12-trimethyltrideca-3,7,11-trien-1-yl)-1,3-dioxane, (6E,10E)-2,6,10-trimethyl-14,14-bis(2,2,2-trifluoroethoxy)pentadeca-2,6,10-triene, 2,5,5-trimethyl-2-((3E,7E)-4,8,12-trimethyltrideca-3,7-dien-1-yl)-1,3-dioxane, (5E,9E)-6,10,14-trimethyl-2,2-bis(2,2,2-trifluoroethoxy)pentadeca-5,9-diene, 2,5,5-trimethyl-2-((3Z,7E)-4,8,12-trimethyltrideca-3,7,11-trien-1-yl)-1,3-dioxane, 2,5,5-trimethyl-2-((3E,7Z)-4,8,12-trimethyltrideca-3,7,11-trien-1-yl)-1,3-dioxane, 2,5,5-trimethyl-2-((3Z,7Z)-4,8,12-trimethyltrideca-3,7,11-trien-1-yl)-1,3-dioxane, (6Z,10E)-2,6,10-trimethyl-14,14-bis(2,2,2-trifluoroethoxy)pentadeca-2,6,10-triene, (6E,10Z)-2,6,10-trimethyl-14,14-bis(2,2,2-trifluoroethoxy)pentadeca-2,6,10-triene, (6Z,10Z)-2,6,10-trimethyl-14,14-bis(2,2,2-trifluoroethoxy)pentadeca-2,6,10-triene, 2,5,5-trimethyl-2-((3Z,7E)-4,8,12-trimethyltrideca-3,7-dien-1-yl)-1,3-dioxane, 2,5,5-trimethyl-2-((3E,7Z)-4,8,12-trimethyltrideca-3,7-dien-1-yl)-1,3-dioxane, 2,5,5-trimethyl-2-((3Z,7Z)-4,8,12-trimethyltrideca-3,7-dien-1-yl)-1,3-dioxane, (5Z,9E)-6,10,14-trimethyl-2,2-bis(2,2,2-trifluoroethoxy)pentadeca-5,9-diene, (5E,9Z)-6,10,14-trimethyl-2,2-bis(2,2,2-trifluoroethoxy)pentadeca-5,9-diene, (5Z,9Z)-6,10,14-trimethyl-2,2-bis(2,2,2-trifluoroethoxy)pentadeca-5,9-diene, (E)-2-(2,6-dimethylhept-1-en-1-yl)-5,5-dimethyl-1,3-dioxane, (E)-3,7-dimethyl-1,1-bis(2,2,2-trifluoroethoxy)oct-2-ene, (E)-3,7-dimethyl-1,1-bis(2,2,2-trifluoroethoxy)octa-2,6-diene, (Z)-2-(2,6-dimethylhept-1-en-1-yl)-5,5-dimethyl-1,3-dioxane, (Z)-3,7-dimethyl-1,1-bis(2,2,2-trifluoroethoxy)oct-2-ene, (Z)-3,7-dimethyl-1,1-bis(2,2,2-trifluoroethoxy)octa-2,6-diene, 2,6-dimethyl-8,8-bis(2,2,2-trifluoroethoxy)oct-2-ene, (R)-2,6-dimethyl-8,8-bis(2,2,2-trifluoroethoxy)oct-2-ene, 2-((1Z,3E)-4,8-dimethylnona-1,3,7-trien-1-yl)-2,5,5-trimethyl-1,3-dioxane, 2-((1E,3Z)-4,8-dimethylnona-1,3,7-trien-1-yl)-2,5,5-trimethyl-1,3-dioxane, 2-((1Z,3Z)-4,8-dimethylnona-1,3,7-trien-1-yl)-2,5,5-trimethyl-1,3-dioxane, (6Z,8E)-2,6-dimethyl-10,10-bis(2,2,2-trifluoroethoxy)undeca-2,6,8-triene, (6E,8Z)-2,6-dimethyl-10,10-bis(2,2,2-trifluoroethoxy)undeca-2,6,8-triene, (6Z,8Z)-2,6-dimethyl-10,10-bis(2,2,2-trifluoroethoxy)undeca-2,6,8-triene, (Z)-2,5-dimethyl-2-(4,8,12-trimethyltridec-3-en-1-yl)-1,3-dioxane, (R,Z)-2,5-dimethyl-2-(4,8,12-trimethyltridec-3-en-1-yl)-1,3-dioxane, (Z)-6,10,14-trimethyl-2,2-bis(2,2,2-trifluoroethoxy)pentadec-5-ene, (R,Z)-6,10,14-trimethyl-2,2-bis(2,2,2-trifluoroethoxy)pentadec-5-ene.

Sequence of Steps

The process of invention has two principle possibilities of sequences.

In the first embodiment the process comprises the steps a1) and b1) and c1):

a1) separating an isomer having E-configuration from the mixture of E/Z isomers of compound of formula (I) or (II) or the acetal or ketal thereof;
and
b1) submitting the isomers having the Z-isomers of compound of formula (I) or (II) or the acetal or ketal thereof to cis/trans isomerisation and adding the isomerization product to the mixture of isomers of compound of formula (I) or (II) or the acetal or ketal thereof;
and c1) submitting the separated isomer having the E-configuration of compound of formula (I) or (II) or the acetal or ketal thereof to hydrogenation by molecular hydrogen in the presence of a chiral iridium complex of formula (III) having the S-configuration at the stereogenic centre indicated by *.

In the second embodiment the process comprises the steps a2) and b2) and c2):

a2) separating an isomer having Z-configuration from the mixture of E/Z isomers of compound of formula (I) or (II) or the acetal or ketal thereof;
and b2) submitting the isomers having the E-configuration of compound of formula (I) or (II) or the acetal or ketal thereof to cis/trans isomerisation and adding the isomerization product to the mixture of isomers of compound of formula (I) or (II) or the acetal or ketal thereof;
and c2) submitting the separated isomer having the Z-configuration of compound of formula (I) or (II) or the acetal or ketal thereof to hydrogenation by molecular hydrogen in the presence of a chiral iridium complex of formula (III) having the R-configuration at the stereogenic centre indicated by *.

Separation

In step a1) and a2) an isomer having E-configuration or having Z-configuration is separated from the mixture of E/Z isomers of compound of formula (I) or (II) or the acetal or ketal thereof.

This separation of isomers in step a1) and a2) can be done in different ways. A first possibility is the separation by means of chromatography.

A further and preferred way of separation is that the separation of isomers in step a1) or a2) is done by distillation. The separation is possible by the fact that the isomers have different boiling points. In order to minimize thermal degradation of the isomers it is advisable to distil under reduced pressure and by means of a distillation column.

Very often the boiling points of the isomers are very similar, however, by using specific distillation techniques and equipment separation or at least enrichment of the desired isomers is nevertheless possible.

In order to optimize the purity of the isomers separated from the mixture, the distillation is made by using specific distillation techniques to ensure that impurities of other isomers are as low as possible. This particularly is also achieved in that only a part, namely the purest fractions, of the desired isomer is collected in a distillation whereas a remainder is left in the distillation flask and that the less pure fractions are either further distilled or joined to the remainder of the distillation.

The separation of the isomers having E-configuration as well as the separation of the isomers having Z-configuration can be achieved by sequential fractional distillation or by using by suitable distillation techniques or equipment. For example by using a side take-off point at a rectification column and eventually further rectification of the material collected at said side take-off, such as the technique and equipment that has been disclosed for example in EP 2 269 998 A2, particularly FIGS. 1 and 3, the entire content of which is hereby incorporated by reference.

The isomer being separated is preferable as pure as possible and contains as little of the other isomers as possible.

In case the compound of formula (I) or (II) contains more than one prochiral carbon-carbon double bonds, such compounds may have the same ("all Z" or "all E") E/Z configurations or have different E/Z configurations (e.g. EZ or ZE). For the purpose of this invention, it is advisable that only those isomers of formula (I) or (II) having the E-configuration at all prochiral carbon-carbon double bonds and only those isomers of formula (I) or (II) having the Z-configuration at all prochiral carbon-carbon double bonds are separated for the asymmetric hydrogenation in step c1) or c2). It is preferred that compounds of formula (I) or (II) which have in the same molecule different E/Z configurations at the prochiral carbon-carbon double bonds are submitted in step b1) or b2) to a step of cis/trans isomerization of said prochiral carbon-carbon double bonds.

Cis/Trans Isomerization

In steps b1) and b2) the isomers are cis/trans isomerized.

Cis/trans isomerization is preferably done in the presence of a cis/trans isomerization catalyst.

In a preferred embodiment the distillation is done in the presence of a cis/trans isomerization catalyst.

Cis/trans isomerization catalysts are catalysts which isomerize the carbon carbon double bonds.

It has been found that for the purpose of this invention said cis/trans isomerization catalyst is preferably nitrogen monoxide (NO) or an organic sulphur compound, particularly a polythiol.

Particularly suitable as cis/trans isomerization catalysts are polythiols of formula (X) or aromatic polythiols, preferably polythiols of formula (X)

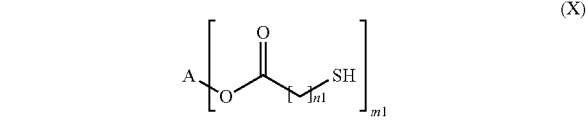

(X)

wherein n1 represents an integer from 1 to 4, particularly 2,
and m1 represents an integer from 2 to 8, particularly 3 or 4, preferably 4;
and A represents an aliphatic m1-valent hydrocarbon group of the molecular weight of between 28 g/mol and 400 g/mol, particularly between 90 and 150 g/mol.

The polythiols pentaerythritol tetra(mercaptoacetate), trimethylolpropane tris(mercaptoacetate), glycol dimercaptoacetate, pentaerythritol tetra-(3-mercaptopropionate), trimethylolpropanetri-(3-mercaptopropionate)(=2-ethyl-2-(((3-mercaptopropanoyl)oxy)methyl)propane-1,3-diyl bis (3-mercaptopropanoate)) and glycol di-(3-mercaptopropionate) have been shown to be highly preferred polythiols of formula (X) and are the preferred polythiols of all the above mentioned polythiols.

Particularly preferred as aromatic polythiols are 4,4'-dimercaptobiphenyl or 4,4'-thiodibenzenethiol.

The use of polythiols of formula (X) as cis/trans isomerization catalysts is very advantageous in that polythiols have generally very low vapor pressures (i.e. high boiling points) allowing them to be used at elevated temperatures, e.g. while distilling the low boiling isomer. Furthermore, the polythiols bear a high density of thiol-functionalities per molecular weight, which is very advantageous, in that only little catalyst needs to be added.

The use of polythiol as cis/trans isomerization catalysts is very advantageous as they allow a very fast isomerization.

Nitrogen monoxide (NO) is a gas and can be introduced to the ketone or ketal to be isomerized as such or in the form of a gas mixture, particularly in combination with at least one inert gas, particularly with nitrogen. In the case a gas mixture is used the amount of nitrogen monoxide in the gas mixture is preferably in the range of 1-99%, particularly of 5-95%, by weight of the gas mixture. Particularly, in view of corrosion and toxicity, the amount of nitrogen monoxide in the gas mixture is preferably in the range of 10-60% by weight of the gas mixture.

The use of nitrogen monoxide as cis/trans isomerization catalysts is very advantageous in that the isomerization catalyst can be removed very easily from the ketone or ketal to be isomerized.

Nitrogen monoxide is preferably introduced to the ketone or ketal at atmospheric pressure or up to 1 MPa overpressure. The over-pressure preferably amounts to 10 to 300 kPa.

Nitrogen monoxide (NO) or a mixture of nitrogen monoxide (NO) with other gases is preferably introduced in a continuous way by means of a tube and bubbled through the ketone or ketal to be isomerized.

The use of cis/trans isomerization allows the transformation of a pure cis or trans isomer or any mixtures of the isomers to yield a thermodynamically equilibrated mixture of the cis and trans isomer. Overall, this enables the separation of the desired isomer by distillation and transformation (isomerization) of the non-preferred isomer (residual isomer) into the desired isomer.

The distillation can be performed in the presence of the cis/trans isomerization catalyst (one-pot isomerization or in-situ isomerization), so that the desired isomer is re-formed continuously and can be separated by distillation.

Furthermore, the cis/trans isomerization can occur in a separate vessel in which the cis/trans isomerization catalyst is added to the remainder of the distillation. Hence, the residual isomer is isomerized by means of a cis/trans isomerization catalyst and subsequently added to the corresponding starting mixture of isomers.

The use of the cis/trans isomerization in step b1) or b2) allows a high yield in the desired isomer. In preferred cases, it can be achieved that essentially all of the undesired isomer is overall isomerized to the desired isomer.

Preferably, particularly in the case where the isomerization catalyst is not nitrogen monoxide, more preferably in the case of polythiols as isomerization catalysts, the isomerization is undertaken at temperatures higher than 20° C., particularly at a temperature of between 20° C. and the boiling point of the desired isomer, particularly between 50° C. and the boiling point of the desired isomer. The isomerization can occur at ambient pressure or at reduced pressure. In case of the one-pot isomerization the isomerization is preferably undertaken under reduced pressure.

Particularly for the case of nitrogen monoxide being cis/trans isomerization catalyst the isomerization is undertaken at ambient or over-pressure.

It further has been observed that in the isomerization with polythiols addition of polar solvents such as amides, pyrrolidones, sulfones, sulfoxides, ionic liquids, particularly N,N-dimethylformide (DMF) or N-methyl-2-pyrrolidone (NMP), sulfolane, dimethylsulfoxide (DMSO) and 1-butyl-3-methylimidazolium bromide has an accelarating effect on the isomerization.

Therefore, it is preferred that the process of a cis/trans isomerization is undertaken in the presence of a polar solvent, particularly a polar solvent which is selected from the group consisting of ionic liquids, particularly 1-butyl-3-methylimidazolium bromide, N,N-dimethylformide (DMF), N-methyl-2-pyrrolidone (NMP), sulfolane and dimethylsulfoxide (DMSO).

More preferred it is that the process of a cis/trans isomerization is undertaken in the presence of a polar solvent, particularly a polar solvent which is selected from the group consisting of ionic liquids, particularly 1-butyl-3-methylimidazolium bromide, N,N-dimethylformide (DMF), N-methyl-2-pyrrolidone (NMP) and dimethylsulfoxide (DMSO).

The amount of cis/trans isomerization catalyst is preferably between 1 and 20% by weight in relation to the amount of the compound of formula (I) or (II).

Asymmetric Hydrogenation

In steps c1) and c2) the separated isomer having the E-configuration or the Z-configuration of compound of formula (I) or (II) or the acetal or ketal thereof are submitted to hydrogenation by molecular hydrogen in the presence of a chiral iridium complex of formula (III).

It is important to realize that it has been found that the isomers of compound of formula (I) or (II) having the E-configuration at the prochiral carbon-carbon double bond(s) are asymmetrically hydrogenated by molecular hydrogen in the presence of a chiral iridium complex of formula (III) having the S-configuration at the stereogenic centre indicated by * stereogenic carbon centre(s) having the R configuration is formed in the hydrogenated compound, i.e. in compound of formula (I-A) or (I-B) (step c1).

It is important to realize that it has been found that the isomers of compounds of formula (I) or (II) having the E-configuration at the prochiral carbon-carbon double bond(s) are asymmetrically hydrogenated to the R-stereoisomer(s), i.e. compounds of formula (I-A) or (I-B) (step c1), by molecular hydrogen in the presence of a chiral iridium complex of formula (III) having the S-configuration at the stereogenic centre indicated by *.

It has been further found that the isomers of compounds of formula (I) or (II) having the Z-configuration at the prochiral carbon-carbon double bond(s) are asymmetrically hydrogenated to the R-stereoisomer(s), i.e. compounds of formula (I-A) or (I-B) (step c2), by molecular hydrogen in the presence of a chiral iridium complex of formula (III) having the R-configuration at the stereogenic centre indicated by *.

The complex of formula (III) is neutral, i.e. the complex consists of a complex cation of formula (III') and anion Y as defined before.

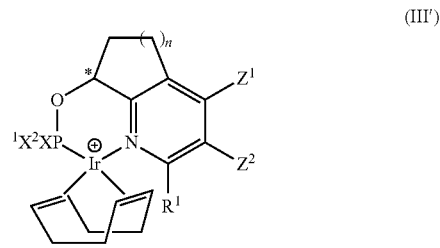

(III')

The person skilled in the art knows that anions and cations may be dissociated.

$X^1$ and/or $X^2$ represent preferably hydrogen atoms, methyl, ethyl, n-propyl, iso-propyl, n-butyl, iso-butyl, tert-butyl, n-pentyl, iso-pentyl, neopentyl, cyclopentyl, cyclohexyl, cycloheptyl, adamantly, phenyl, benzyl, o-tolyl, m-tolyl, p-tolyl, 4-methoxyphenyl, 4-trifluoromethylphenyl, 3,5-di-tert-butylphenyl, 3,5-dimethoxyphenyl, 1-naphthyl, naphthyl, 2-furyl, ferrocenyl or a phenyl group which is substituted with one to five halogen atoms.

In case of $X^1$ and/or $X^2$ representing phenyl groups which are substituted with one to five halogen atoms, the phenyl groups substituted by fluorine atoms are particularly useful, i.e. $C_6H_4F$, $C_6H_3F_2$, $C_6H_2F_3$, $C_6HF_4$ or $C_6F_5$.

In case of $X^1$ and/or $X^2$ representing phenyl groups which are substituted with one to three $C_{1-4}$-alkyl, the phenyl groups substituted by methyl group(s) are particularly useful, particularly ortho-tolyl and para-tolyl.

Preferably both $X^1$ and $X^2$ represent the same substituent.

Most preferred both $X^1$ and $X^2$ are phenyl or ortho-tolyl groups.

It is preferred that the $C_1$-$C_4$-alkyl or alkoxy groups used in the definition of $R^2$, $R^3$, $R^4$, $R^5$ $R^6$, $R^7$, $R^8$, $R^9$ and $R^{10}$ above are primary or secondary, preferably primary, alkyl or alkoxy groups.

A particularly suited substituent $R^1$ of formula (IVa) is the 9-anthryl or 1-naphthyl group.

A further particularly suited substituent $R^1$ of formula (IVb) is the mesityl group.

A further particularly suited substituent $R^1$ of formula (IVc) is the 2-naphthyl group.

Preferably $R^1$ is represented by phenyl (abbreviated as "Ph") or formula (IV-1) or (IV-2) or (IV-3), particularly (IV-1) or (IV-3).

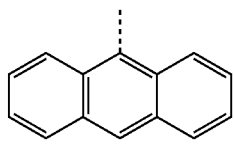

(IV-1)

abbreviated as "Anth"

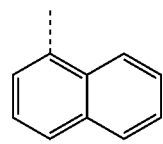

(IV-2)

abbreviated as "1-Naphth"

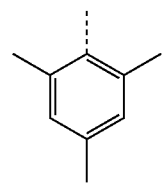

(IV-3)

abbreviated as "Mes"

It has been found that the most preferred substituent $R^1$ is either 9-anthryl or phenyl.

The preferred chiral iridium complexes of formula (III) are the complexes of formulae (III-A), (III-B), (III-C), (III-D), (III-E) and (III-F).

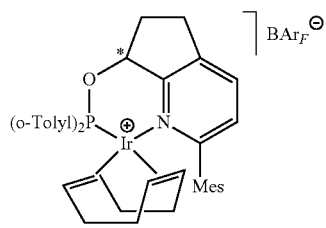

(III-A)

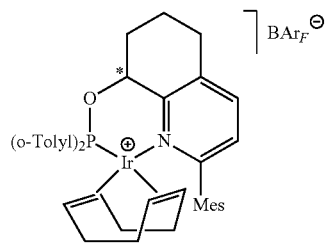

(III-B)

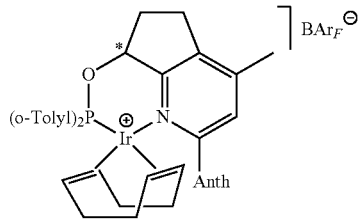

(III-C)

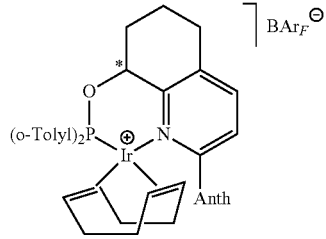

(III-D)

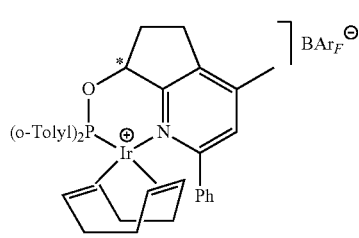

(III-E)

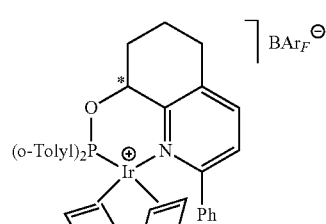

(III-F)

Most preferred as chiral iridium complexes of formula (III) are the complexes of formulae (III-C) and (III-D) and (III-F), particularly the one of formula (III-C) or (III-F).

The chiral iridium complexes of formula (III) can be synthesized accordingly as described in detail in *Chem. Sci.*, 2010, 1, 72-78 whose entire content is hereby incorporated by reference.

The iridium complex of formula (III) is chiral. The chirality at said chiral centre marked by the asterisk is either S or R, i.e. there exist two enantiomers (IIIa) and (IIIb) of the chiral complex of formula (III):

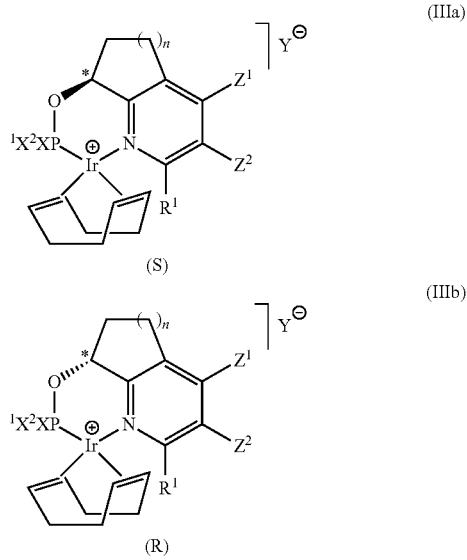

The individual enantiomers of the complex of formula (III) could be principally separated after the complexation step from a racemic mixture. However, as *Chem. Sci.*, 2010, 1, 72-78 discloses, the synthesis of the complex of formula (III) comprises a reaction involving a non-racemic chiral alcohol. As it is known that the further reaction steps do not modify the chirality of the complex its isomeric purity (S:R-ratio) is governed therefore by the enantiomeric purity of said alcohol. As said corresponding alcohol can be obtained in a R/S ratio of more than 99% resp. lower than 1%, the complex of formula (III) can be obtained in extremely high enantiomeric purities, particularly in a R/S ratio of more than 99% resp. lower than 1%.

The chiral iridium complex is preferably used in an excess of one enantiomer.

Particularly, it is preferred that the ratio of the molar amounts of the individual enantiomers R:S of the chiral iridium complex of formula (III) is more than 90:10 or less than 10:90, preferably in the range of 100:0 to 98:2 or 0:100 to 2:98. Most preferred is that this ratio is about 100:0 resp. about 0:100. The ultimately preferred ratio is 100:0 resp. 0:100.

In one embodiment the stereogenic centre indicated by * has the R-configuration.

In another embodiment the stereogenic centre indicated by * has the S-configuration.

The hydrogenating agent is molecular hydrogen ($H_2$).

The amount of chiral iridium complex is preferably present during the hydrogenation in an amount in the range from 0.0001 to 5 mol-%, preferably from about 0.001 to about 2 mol-%, more preferably from about 0.001 to about 1 mol-%, most preferably from 0.001 to 0.1 mol-%, based on the amount of the compound of formula (I) or (II) or the acetal or ketal thereof.

The hydrogenation can be carried out in substance or in an inert carrier, particularly in an inert solvent, or a mixture of inert solvents. The hydrogenation is preferred carried out in substance (neat).

Preferred suitable solvents are halogenated hydrocarbons, hydrocarbons, carbonates, ethers and halogenated alcohols.

Particularly preferred solvents are hydrocarbons, fluorinated alcohols and halogenated hydrocarbons, particularly halogenated aliphatic hydrocarbons.

Preferred examples of hydrocarbons are hexane, heptane, toluene, xylene and benzene, particularly toluene and heptane.

Preferred ethers are dialkylethers. Particularly useful ethers are dialklyethers with less than 8 carbon atoms. Most preferred ether is methyl tert.-butyl ether ($CH_3$—O—C($CH_3$)$_3$).

Preferred halogenated alcohols are fluorinated alcohols. A particularly preferred fluorinated alcohol is 2,2,2-trifluoroethanol.

One preferred group of halogenated hydrocarbon are halogenated aromatic compounds, particularly chlorobenzene.

Preferred examples of halogenated aliphatic hydrocarbons are mono- or polyhalogenated linear or branched or cyclic $C_1$- to $C_{15}$-alkanes. Especially preferred examples are mono- or polychlorinated or -brominated linear or branched or cyclic $C_1$- to $C_{15}$-alkanes. More preferred are mono- or polychlorinated linear or branched or cyclic $C_1$- to $C_{15}$-alkanes. Most preferred are dichloromethane, 1,2-dichloroethane, 1,1,1-trichloroethane, chloroform, and methylene bromide.

The most preferred solvent for the hydrogenation is dichloromethane.

The amount of solvent used is not very critical. However, it has been shown that the concentration of the ketone or ketal to be hydrogenated is preferably between 0.05 and 1 M, particularly between 0.2 and 0.7 M.

The hydrogenation reaction is conveniently carried out at an absolute pressure of molecular hydrogen from about 1 to about 100 bar, preferably at an absolute pressure of molecular hydrogen from about 20 to about 75 bar. The reaction temperature is conveniently between about 0 to about 100° C., preferably between about 10 to about 60° C.

The sequence of addition of the reactants and solvent is not critical.

The technique and apparatus suitable for the hydrogenation is principally known to the person skilled in the art.

By the asymmetric hydrogenation a prochiral carbon-carbon double bond is hydrogenated to form a chiral stereogenic centre at one or both of the carbon atoms.

Hydrogenated Compounds

As a result of the asymmetric hydrogenation in steps c1) and c2) the compound of formula (I-A) or (I-B) or an acetal or a ketal thereof is formed.

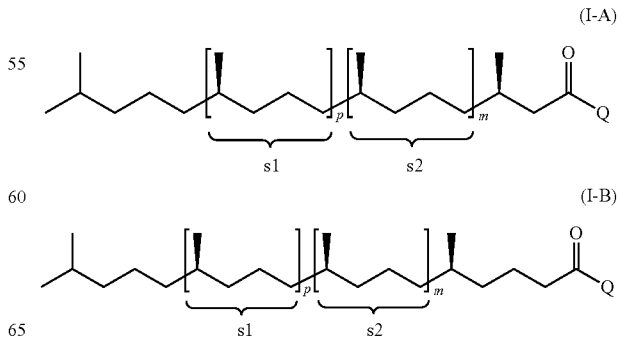

In case the carbon-carbon double bonds of compound of formula (I) or (II) or the acetals or ketals thereof is prochiral a stereogenic centre is formed in step c1) and c2). This stereogenic centre has the R-configuration. In case the carbon-carbon double bonds of compound of formula (I) or (II) or the acetals or ketals thereof are not prochiral no stereogenic centre has been formed in step c1) and c2).

Preferred compounds of formula (I-A) and (I-B) are (R)-3,7-dimethyloctanal, (R)-6,10-dimethylundecan-2-one and (6R,10R)-6,10,14-trimethylpentadecan-2-one.

In case the compound of formula (I) or (II) has been asymmetrically hydrogenated in the form of a ketal or acetal, after the asymmetric hydrogenation the asymmetrically hydrogenated ketal or acetal has preferably the formula (XV) or (XVI) or (XVII).

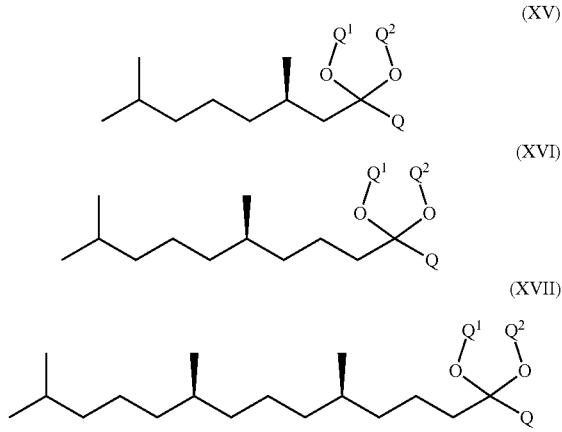

and wherein Q and $Q^1$ and $Q^2$ are as defined for formula (XI) or (XII).

Particularly the ketal or acetal of formula (XV) or (XVI) or (XVII) is selected from the group consisting of formula (XVa), (R)-2-(4,8-dimethylnonyl)-2,5,5-trimethyl-1,3-dioxane, (R)-6,10-dimethyl-2,2-bis(2,2,2-trifluoroethoxy)undecane, and (6R,10R)-6,10,14-trimethyl-2,2-bis(2,2,2-trifluoroethoxy)pentadecane.

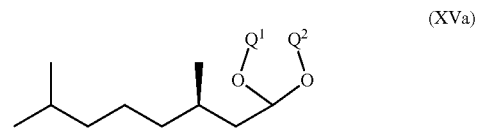

In formula (XVa) Q and $Q^1$ and $Q^2$ are as defined for formula (XI) or (XV).

In one embodiment the ketal or acetal of formula (XI) or (XV) are selected from the group consisting of (R)-1,1-dimethoxy-3,7-dimethyloctane, (R)-1,1-diethoxy-3,7-dimethyloctane, (R)-3,7-dimethyl-1,1-dipropoxyoctane, (R)-1,1-dibutoxy-3,7-dimethyloctane, (R)-1,1-diisobutoxy-3,7-dimethyloctane, (R)-3,7-dimethyl-1,1-bis(2,2,2-trifluoroethoxy)octane, (R)-2-(2,6-dimethylheptyl)-1,3-dioxolane, 2-((R)-2,6-dimethylheptyl)-4-methyl-1,3-dioxolane, 2-((R)-2,6-dimethylheptyl)-4,5-dimethyl-1,3-dioxolane, 2-((R)-2,6-dimethylheptyl)hexahydro-benzo[d][1,3]dioxole, (R)-2-(2,6-dimethylheptyl)-1,3-dioxane, (R)-2-((R)-2,6-dimethylheptyl)-5-methyl-1,3-dioxane, (R)-2-(2,6-dimethylheptyl)-5,5-dimethyl-1,3-dioxane; (R)-2-(4,8-dimethylnonyl)-2,5,5-trimethyl-1,3-dioxane, (R)-6,10-dimethyl-2,2-bis(2,2,2-trifluoroethoxy)undecane and (6R,10R)-6,10,14-trimethyl-2,2-bis(2,2,2-trifluoroethoxy)pentadecane.

In a further embodiment the ketal or acetal of formula (XI) or (XV) are selected from the group consisting of (R)-3,7-dimethyl-1,1-bis(2,2,2-trifluoroethoxy)octane, (R)-2-(2,6-dimethylheptyl)-5,5-dimethyl-1,3-dioxane; (R)-2-(4,8-dimethylnonyl)-2,5,5-trimethyl-1,3-dioxane, (R)-6,10-dimethyl-2,2-bis(2,2,2-trifluoroethoxy)undecane and (6R,10R)-6,10,14-trimethyl-2,2-bis(2,2,2-trifluoroethoxy)pentadecane.

Despite the fact that the asymmetric hydrogenation of the compounds of formula (I) or (II) by means of molecular hydrogen in the presence of a chiral iridium complex, particularly those of formula (III), is already rather fast and efficient and shows high conversion rates as well as excellent selectivities, it has been observed that the asymmetric hydrogenation can even be improved when ketals or acetals of the corresponding ketones are asymmetrically hydrogenated.

In a preferred embodiment of the invention the asymmetric hydrogenation in step c1) and/or step c2) takes place in the presence of an additive which is selected from the group consisting of organic sulfonic acids, transition metal salts of organic sulfonic acids, metal alkoxides, aluminoxanes, alkyl aluminoxanes and $B(R)_{(3-v)}(OZ)_v$; wherein v stands for 0, 1, 2 or 3 and R stands for F, a $C_{1-6}$-alkyl, a halogenated $C_{1-6}$-alkyl, an aryl or halogenated aryl group; and Z stands a $C_{1-6}$-alkyl, a halogenated $C_{1-6}$-alkyl, an aryl or halogenated aryl group.

Particularly suitable additives are selected from the group consisting of triflic acid, alkyl aluminoxanes, particularly methyl aluminoxane, ethyl aluminoxane, tetra alkoxy titanates, $B(R)_{(3-v)}(OZ)_v$; particularly tri-isopropylborate and triethylborane and $BF_3$, preferably in the form of a $BF_3$ etherate.

Particularly useful as the transition metal salts of organic sulfonic acids are scandium, indium, yttrium and zirconium salts of organic sulfonic acids.

Metal alkoxides are known to the person skilled in the art. This term particularly relates to the alkoxides of the elements of the group 4 and 13 of the periodic system. It is also known to the person skilled in the art that the metal alkoxides often do not form well-defined structures. Characteristically, metal alkoxides have hydrocarbyl group bound by an oxygen atom to a metal centre. A metal alkoxide may also have different metal centres which are bridged by oxygen or oxygen containing groups, such as for example (polynuclear) aluminium oxoalkoxides.

Particularly useful as metal alkoxides are titanium alkoxides (also being called alkoxy titanates) zirconium alkoxides (also being called alkoxy zirconates) or aluminium alkoxides.

A particularly preferred class of metal alkoxide is of the type of polynuclear aluminium oxoalkoxides such as disclosed in *J. Chem. Soc., Dalton Trans.*, 2002, 259-266 or in *Organometallics* 1993, 12, 2429-2431.

Alkyl aluminoxanes, are known products which are particularly useful as co-catalysts for olefin polymerizations of the Ziegler-Natta type. They are prepared by controlled hydrolysis of trialkylaluminium compound, particularly trimethylaluminium or triethylaluminium. The hydrolysis can be achieved for example by hydrated metal salts (metal salts containing crystal water).

Preferably the additive is selected from the group consisting of triflic acid, alkyl aluminoxanes, particularly methyl aluminoxane, ethyl aluminoxane, tetra alkoxy titanates, $B(R)_{(3-v)}(OZ)_v$; particularly tri-isopropylborate and triethylborane and $BF_3$, preferably in the form of a $BF_3$ etherate.

More preferred are triflic acid, alkyl aluminoxanes, particularly methyl aluminoxane, ethyl aluminoxane, tetra alkoxy titanates, $B(R)_{(3-v)}(OZ)_v$; particularly tri-isopropylborate and triethylborane.

Especially good results have been obtained by an additive with has been obtained from trimethylaluminoxane and 2,2,2-trifluoroethanol or from trialkylaluminium and 2,2,2-trifluoroethanol.

It has been found that the quality and speed of the asymmetric hydrogenation using molecular hydrogen in the presence of a chiral iridium complex is enhanced significantly when the above mentioned additives are used.

It has been further observed that, most significantly, the efficiency of the asymmetric hydrogenation is maximized when the above mentioned additives are used with the corresponding ketal or acetals of the compound of formula (I) or (II).

The increased efficiency has the effect that the amount of chiral iridium complex can be remarkably lowered by using an ketal or acetal of compound of formula (I) or (II) and/or addition of the mentioned additive(s), particularly in the combination with fluorinated alcohols, particularly 2,2,2-trfluoroethanol, to achieve a given yield and stereospecific hydrogenation in the asymmetric hydrogenation as compared to the corresponding asymmetric hydrogenation of the compound of formula (I) or (II) as such.

Furthermore, in case the acetal or the ketal of compound of formula (I) or (II) has been hydrogenated in step c1) and/or c2), that the hydrogenated ketal or acetal can be hydrolysed to the corresponding ketone or aldehyde, i.e. to compound of formula (I-A) or (I-B) in an optional step e). The hydrolysis and conditions for the hydrolysis of the hydrogenated ketal or acetal to the corresponding ketone or aldehyde are known to the person skilled in the art. Particularly suitable is the hydrolysis by means of an acid and isolation of the ketone or aldehyde, particularly by means of extraction.

In a further aspect the invention relates to a ketal of formula (XX-A)

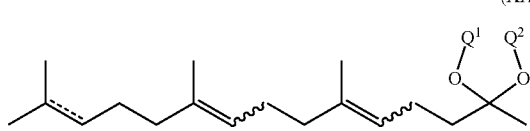

(XX-A)

wherein $Q^1$ and $Q^2$ are as defined in detail before for formula (XI) and (XII) and wherein the double bond having dotted lines ( ------ ) represent either a single carbon-carbon bond or a double carbon-carbon bond.

In a further aspect the invention relates to a ketal of formula (XX-B)

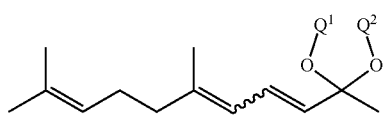

(XX-B)

wherein $Q^1$ and $Q^2$ are as defined in detail before for formula (XI) and (XII) and where a wavy line represents a carbon-carbon bond which is links the adjacent carbon-carbon double bonds so as to have said carbon-carbon double bonds either in the Z or in the E-configuration.

In a further aspect the invention relates to an acetal of formula (XX-C)

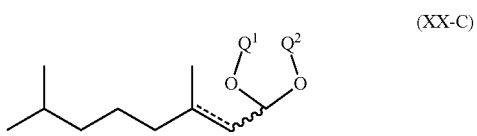

(XX-C)

wherein $Q^1$ and $Q^2$ are as defined in detail before for formula (XI) and (XII) and wherein the double bond having dotted lines ( ------ ) represent either a single carbon-carbon bond or a double carbon-carbon bond; and wherein a wavy line represents a carbon-carbon bond which is either linked to an adjacent single carbon bond ( ------ ) representing ( ———— ) or to an adjacent carbon-carbon double bond ( ------ ) representing ( ════ ) so as to have said carbon-carbon double bond either in the Z or in the E-configuration.

In a further aspect the invention relates to an acetal of formula (XXI-A) or (XXI-B) or (XXI-C) or (XXI-D)

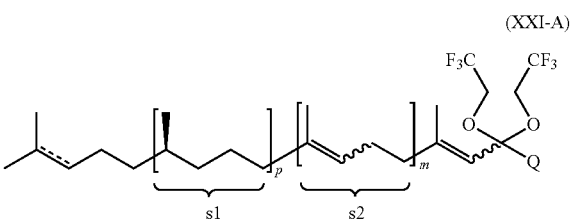

(XXI-A)

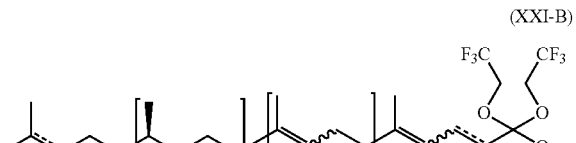

(XXI-B)

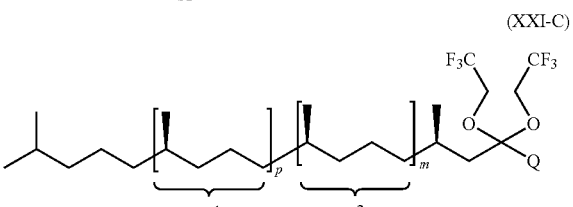

(XXI-C)

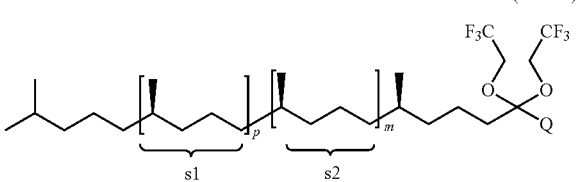

(XXI-D)

wherein Q stands for H or $CH_3$ and m and p stand independently from each other for a value of 0 to 3 with the proviso that the sum of m and p is 0 to 3, wherein the double bond having dotted lines ( ----- ) in the above formulae represents either a single carbon-carbon bond or a double carbon-carbon bond; and wherein a wavy line represents a carbon-carbon bond which is linked to an adjacent single carbon bond ( ----- ) representing ( ——— ) or to an adjacent carbon-carbon double bond ( ----- ) representing ( ===== ) so as to have said carbon-carbon double bond either in the Z or in the E-configuration.

All these compounds of formula (XX-A), (XX-B), (XX-C), (XXI-A), (XXI-B), (XXI-C) or (XXI-D) are sub groups of the acetals or ketals of compound of formula (I) or (II) or acetals or ketones of the compound of formula (I-A) or (I-B) which have been shown to be very interesting starting materials or products of the process of manufacturing compound of formula (I-A) or (I-B) or an acetal or a ketal thereof described in detail before.

In a further aspect, the invention relates to a composition comprising
 at least one ketal of formula (XI) or (XII) and
 at least one chiral iridium complex of formula (III)

The ketal of formula (XI) or (XII) and chiral iridium complex of formula (III), their ratios and as well their preferred embodiments, properties and effects have been discussed in this documents already in great detail.

Compound of formula (I-A), (I-B) as well as particularly compounds of formula (XX-A), (XX-B), (XX-C), (XXI-A), (XXI-B), (XXI-C) or (XXI-D) as well as compositions comprising a ketal of formula (XI) or (XII) and a chiral iridium complex of formula (III) are interesting to be used as intermediates for the synthesis of tocopherols, vitamin K1, as well as for the synthesis of compositions in the field of flavours and fragrances or pharmaceutical products. The majority of them have a typical odour which makes them also very attractive to be used as ingredients in products of the industry of flavours and fragrances such as in perfumes.

FIGURES

In the following paragraphs some preferred embodiments of the inventions are further discussed by means of schematic FIGS. 1 to 3. This, however, is not to be understood as limiting the invention to the embodiments described here in the figures.

Figure 1B:
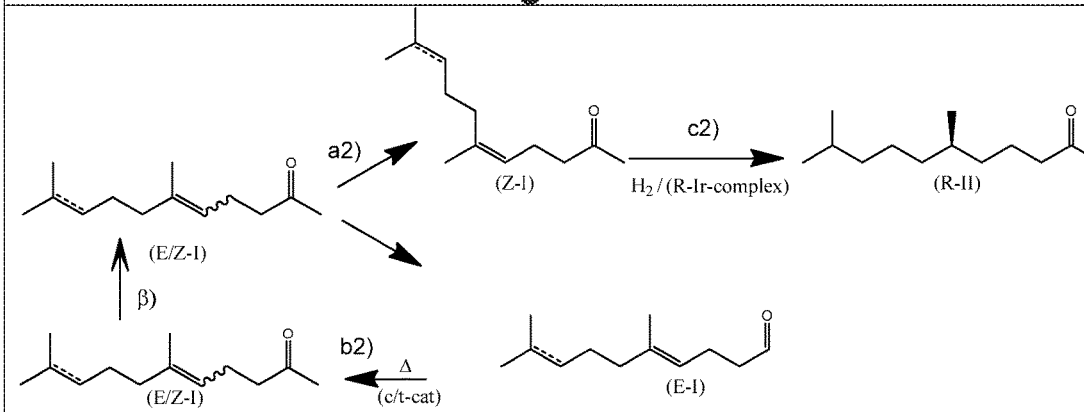
Figure 1C:
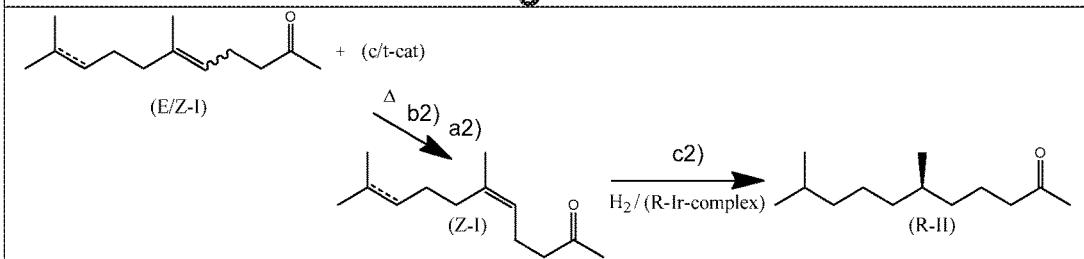
Figure 2A:
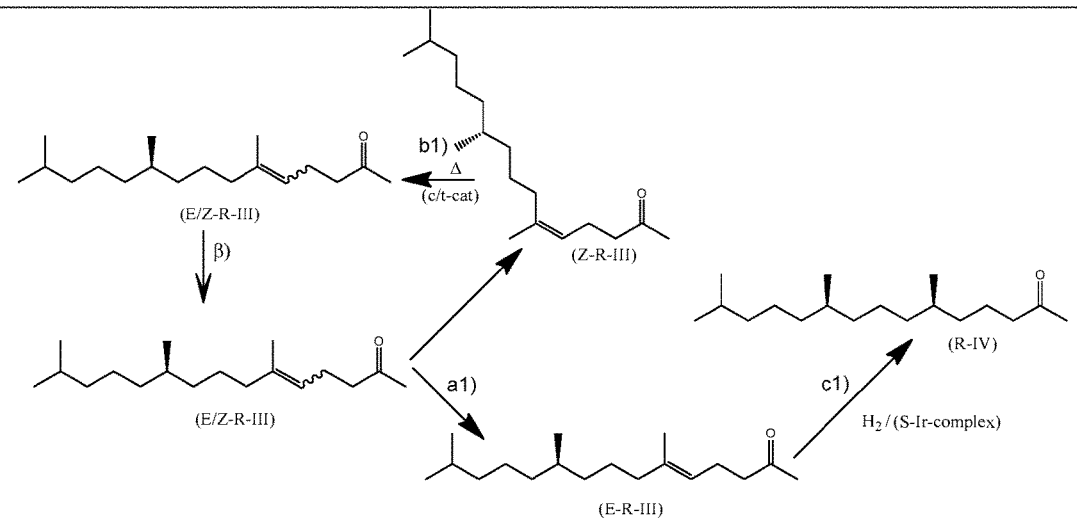
Figure 2B:
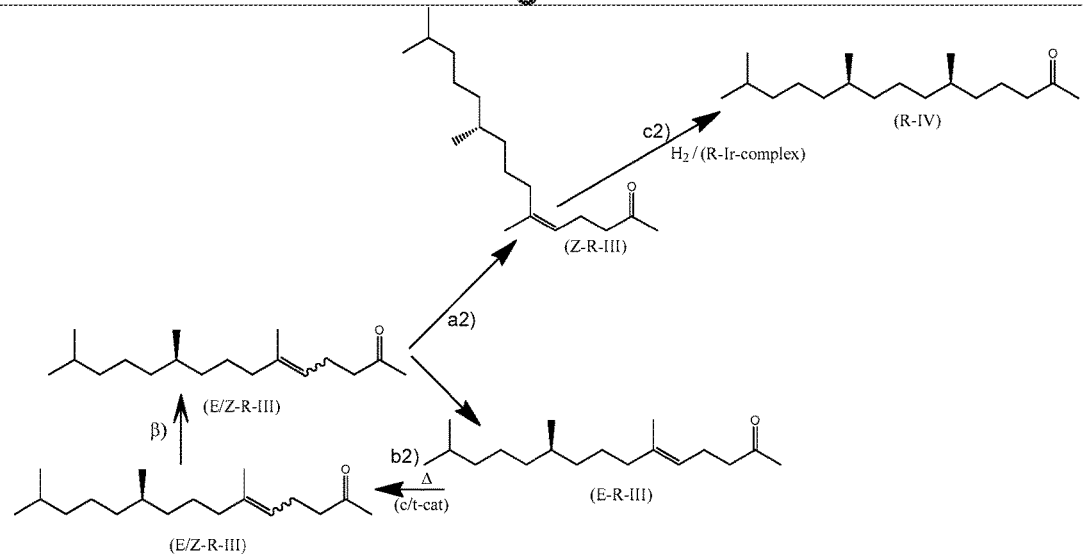
Figure 2C:
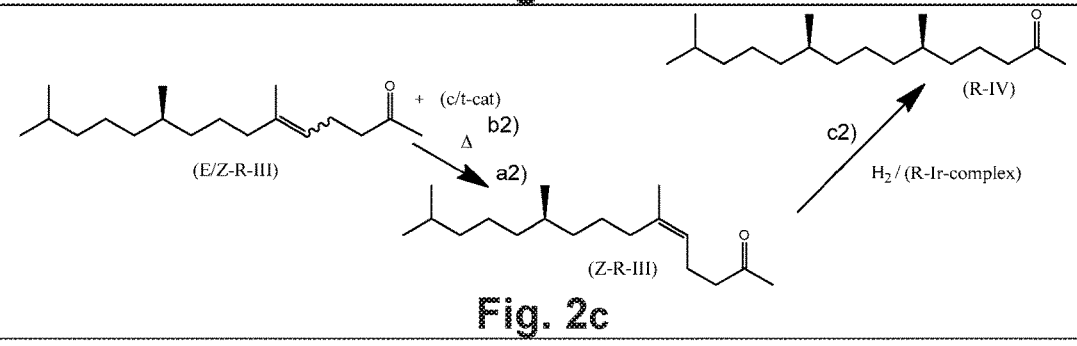
Figure 3:
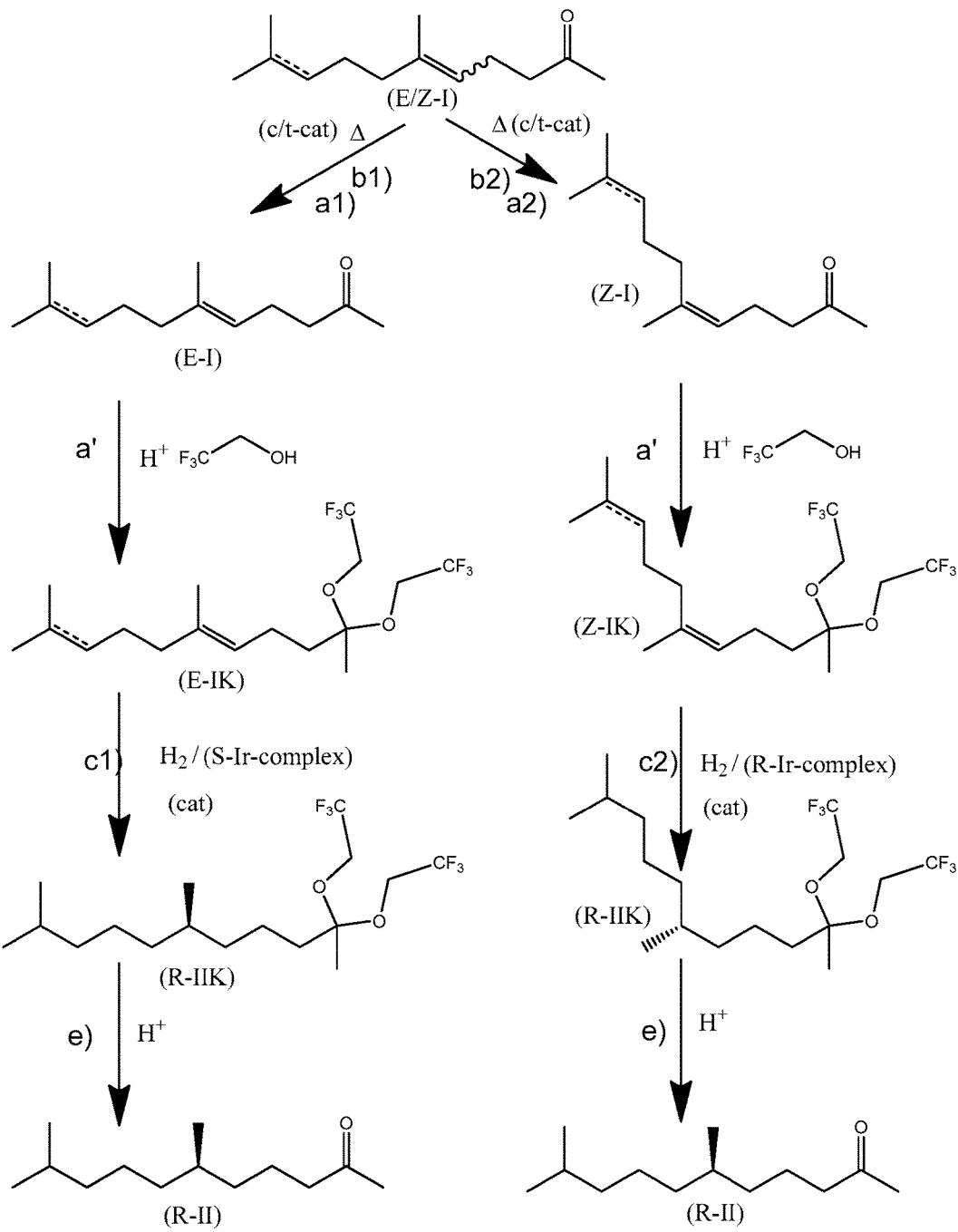

The FIGS. 1 to 3 show schematically an embodiment of the process of invention on 6,10-dimethylundec-5-en-2-one and 6,10-dimethylundeca-5,9-dien-2-one and 6,10,14-trimethylpentadec-5-en-2-one as examples of compounds of formula (I) and (II).

The reference signs in parentheses in the figures, such as (R-II) are used for identification purposes as described below and are not to be confused with the indication of formula such as (II) used in the rest of this document.

In FIGS. 1 a) and b), the process is schematically shown for the synthesis of (R)-6,10-dimethylundecan-2-one (R-II) from an E/Z mixture (E/Z-I) of 6,10-dimethylundec-5-en-2-one or 6,10-dimethylundeca-5,9-dien-2-one.

FIG. 1 a) shows the first pathway. The E-isomer (E-I) (i.e. (E)-6,10-dimethylundec-5-en-2-one or (E)-6,10-dimethylundeca-5,9-dien-2-one, respectively) is separated in step a1) from the corresponding Z-isomer (Z-I) (i.e (Z)-6,10-dimethylundec-5-en-2-one or (Z)-6,10-dimethylundeca-5,9-dien-2-one, respectively) are separated from the mixture of E/Z isomers (E/Z-I). The separation in step a1) is preferably done by distillation over a column.

The E-isomer (E-I) is asymmetrically hydrogenated in step c1) using molecular hydrogen in the presence of the chiral iridium complex of formula (IIIa) (S-Ir-complex) having the S-configuration at the stereogenic centre indicated by * in formula (III). Z-isomer (Z-I) is subjected to cis/trans isomerization in step b1) by addition of a cis/trans isomerization catalyst (c/t-cat) and heating. The cis/trans isomerization catalyst preferably used is NO or a polythiol, particularly of formula (X). By the action of the cis/trans isomerization catalyst the (Z-isomer (Z-I)) is isomerized to a mixture of the E-isomer and the Z-isomer (E/Z-I) which can be added in step β) to the mixture.

FIG. 1 b) shows the second pathway. The Z-isomer (Z-I) (i.e. (Z)-6,10-dimethylundec-5-en-2-one or (Z)-6,10-dimethylundeca-5,9-dien-2-one, respectively) is separated in step a2) from the corresponding E-isomer (E-I) (i.e (E)-6,10-dimethylundec-5-en-2-one or (E)-6,10-dimethylundeca-5,9-dien-2-one, respectively) are separated from the mixture of E/Z isomers (E/Z-I). The separation in step a2) is preferably done by distillation over a column.

The Z-isomer (Z-I) is asymmetrically hydrogenated in step c2) using molecular hydrogen in the presence of the chiral iridium complex of formula (IIIa) (R-Ir-complex) having the R-configuration at the stereogenic centre indicated by * in formula (III). E-isomer (E-I) is subjected to cis/trans isomerization in step b2) by addition of a cis/trans isomerization catalyst (c/t-cat) and heating. The cis/trans isomerization catalyst preferably used is NO or a polythiol, particularly of formula (X). By the action of the cis/trans isomerization catalyst the (E-isomer (E-I)) is isomerized to a mixture of the E-isomer and the Z-isomer (E/Z-I) which can be added in step β) to the mixture.

In FIG. 1c) the (Z)-isomer (Z-I) is asymmetrically hydrogenated as described above for FIG. 1b) in step c2). A cis/trans isomerization catalyst (c/t-cat) is added to the mixture of the E-isomer and the Z-isomer (E/Z-I). In step a2) the separation of the isomer (Z-isomer (Z-I)) is done by distillation in the presence of the cis/trans isomerization catalyst in a (one-pot isomerization or in-situ isomerization). As the Z-isomer is separated by distillation, the remainder, enriched in the higher boiling isomer, including the E-isomer, is isomerized so that in the distillation vessel a thermodynamic equilibrium between the Z- and E-isomers is formed continuously. This procedure may allow all of the undesired isomer being present in the isomer mixture at the beginning to be converted to the Z-isomer. The scheme would analogously apply in the case where the E-isomer would be isomer to be separated in step a1), isomerized in step b1) and hydrogenated in step c1).

FIG. 2 shows schematically a different example. FIG. 2 corresponds to the FIG. 1 except that the individual substances are extended by a C5 unit. In analogy, at least one isomer of the mixture (E/Z-R-III) of (R,E)-6,10,14-trimethylpentadec-5-en-2-one and (R,Z)-6,10,14-trimethylpentadec-5-en-2-one (E/Z-R-III) is separated in step b1) or b2) and asymmetrically hydrogenated to (6R,10R)-6,10,14-trimethylpentadecan-2-one (R-IV) in step b1) or b2).

FIG. 3) shows schematically the preferred process using a ketal or acetal during the hydrogenation process. On the left side the one-pot isomerization in step b1) and separation of the E-isomer (E-I) (i.e. (E)-6,10-dimethylundec-5-en-2-one or (E)-6,10-dimethylundeca-5,9-dien-2-one from the mixture of E/Z isomers (E/Z-I) is shown. The separation in step a1) is preferably done by distillation over a column. The E-isomer (E-I) is converted into the corresponding ketal, i.e. into the ketal of the E-isomer (E-IK) by using an alcohol (in FIG. 3 2,2,2-trifluoroethanol is shown) in the presence of an acid. The ketal of the E-isomer (E-IK) is asymmetrically hydrogenated in step c1) using molecular hydrogen in the presence of the chiral iridium complex of formula (IIIa) (S-Ir-complex) having the S-configuration at the stereogenic centre indicated by * in formula (III). The ketal of (R)-6,10-dimethylundecan-2-one (R-IIK) is hydrolysed by acid into (R)-6,10-dimethylundecan-2-one (R-II) in step e).

On the right side the second variant is shown. The Z-isomer (E-Z) (i.e. (Z)-6,10-dimethylundec-5-en-2-one or (Z)-6,10-dimethylundeca-5,9-dien-2-one is separated from the mixture of E/Z isomers (E/Z-I) in step a2) which is preferably done by distillation over a column. The remainder of the distillation (a2) is is isomerized by one-pot isomerization in step b2). The Z-isomer (Z-I) is then converted into the corresponding ketal, i.e. into the ketal of the Z-isomer (Z-IK) by using an alcohol (in FIG. 3 2,2,2-trifluoroethanol is shown) in the presence of an acid.

The ketal of the Z-isomer (Z-IK) is asymmetrically hydrogenated in step c2) using molecular hydrogen in the presence of the chiral iridium complex of formula (IIIa) (R-Ir-complex) having the R-configuration at the stereogenic centre indicated by * in formula (III). The ketal of (R)-6,10-dimethylundecan-2-one (R-IIK) is hydrolysed by acid into (R)-6,10-dimethylundecan-2-one (R-II) in step e).

EXAMPLES

The present invention is further illustrated by the following experiments.

Analytical Methods

GC Determination of E/Z-ratio and/or purity of 6,10-dimethylundec-5-en-2-one (DHGA), (R)-6,10-dimethylundecan-2-one (THGA) and (R)-6,10,14-trimethylpentadec-5-en-2-one (R-THFA)

Agilent 6850, column DB-5HT (30 m, 0.25 mm diameter, 0.10 μm film thickness), 107 kPa helium carrier gas). The samples were injected as solutions in hexane, split ratio 300:1, injector temperature 200° C., detector temperature 350° C. Oven temperature program: 100° C. (8 min), 10° C./min to 200° C. (1 min), 20° C./min to 220° C. (4 min), runtime 24 min.

GC Determination of purity of (6R,10R)-6,10,14-trimethylpentadecan-2-one

Agilent 6850, column DB-5HT (30 m, 0.25 mm diameter, 0.10 μm film thickness), 115 kPa helium carrier gas). The samples were injected as solutions in hexane, split ratio 300:1, injector temperature 200° C., detector temperature 350° C. Oven temperature program: 120° C. (5 min), 14° C./min to 260° C. (2 min), 20° C./min to 280° C. (4 min), runtime 22 min.

GC Determination of purity of (3RS,7R,11R)-3,7,11,15-tetramethylhexadec-1-en-3-ol ((R,R)-Isophytol)

Agilent 6850 instrument equipped with FID. Agilent DB-5 column (30 m, 0.32 mm diameter, 0.25 μm film thickness) with 25 psi molecular hydrogen carrier gas. The samples were injected as solutions in acetonitrile with a split ratio of 50:1. Injector temperature: 250° C., detector temperature: 350° C. Oven temperature program: 100° C., 4° C./min to 250° C.

GC Determination of E/Z-ratio and/or purity of 6,10,14-trimethylpentadeca-5,9-dien-2-one, 6,10,14-trimethylpentadeca-5,9,13-trien-2-one, 6,10-dimethylundeca-5,9-dien-2-one and ketals Agilent 6850 instrument, column Agilent DB-5 (123-5032E, 30 m×0.32 mm, film 0.25 μm), the samples were injected as solutions in acetonitrile, split ratio 50:1, injector 250° C., detector 350° C. Oven temperature program: 100° C., 4° C./min until 250° C., 37.5 min total runtime.

| Retention times ($t_R$): | min. |
|---|---|
| (5E,9E)-6,10,14-trimethylpentadeca-5,9,13-trien-2-one (EE-FA) | 22.2 |
| EE-FA-DM | decomp.[2] |
| EE-FA-tfe | 23.1, pc[1] |
| (5Z,9Z)-6,10,14-trimethylpentadeca-5,9,13-trien-2-one (ZZ-FA) | 21.0 |
| ZZ-FA-DM | 23.0, pc[1] |
| ZZ-FA-neo | 27.9 |
| (5E,9E)-6,10,14-trimethylpentadeca-5,9-dien-2-one (EE-DHFA) | 21.2 |
| EE-DHFA-DM | 24.6, pc[1] |
| EE-DHFA-neo | 29.5 |
| EE-DHFA-tfe | 22.4 |
| (5Z,9Z)-6,10,14-trimethylpentadeca-5,9-dien-2-one (ZZ-DHFA) | 20.0 |
| ZZ-DHFA-DM | 23.0, pc[1] |
| ZZ-DHFA-neo | 27.9 |
| (E)-6,10-dimethylundeca-5,9-dien-2-one (E-GA) | 11.0 |
| E-GA-DM | 14.8 |
| E-GA-neo | 20.5 |
| E-GA-tfe | 13.2, pc[1] |
| (Z)-6,10-dimethylundeca-5,9-dien-2-one (Z-GA) | 10.6 |
| Z-GA-DM | 14.0, pc[1] |
| Z-GA-neo | 19.5 |
| E-DHGA-DM | 14.1, pc[1] |
| E-DHGA-neo | 19.6, pc[1] |
| E-DHGA-tfe | 12.5 |
| Z-DHGA-DM | 13.0, pc[1] |
| Z-DHGA-neo | 18.5, pc[1] |
| R,E-THFA-DM | 24.2, pc[1] |
| R,E-THFA-neo | 29.1 |
| R,Z-THFA-DM | 23.1, pc[1] |
| R,Z-THFA-neo | 27.9 |
| R-THGA-DM | 13.1 |
| R-THGA-neo | 18.9 |
| R-THGA-tfe | 11.8 |
| RR-C18-DM | decomp.[2] |
| RR-C18-neo | 28.5 |
| RR-C18-tfe | 21.4 |

[1]pc = partial decomposition
[2]decomp. = decomposition during GC analysis

Analysis of the Asymmetrically Hydrogenated Reaction Products

The corresponding dimethyl, ethylene glycol, neopentyl and bis(trifluoroethyl) ketals were hydrolyzed to the ketones in the presence of aqueous acid and analyzed for conversion and their stereoisomer ratio using the following methods for ketones.

The conversion of the hydrogenation reaction was determined by gas chromatography using an achiral column.

Method for Conversion:

Agilent 7890A GC equipped with FID. Agilent HP-5 column (30 m, 0.32 mm diameter, 0.25 μm film thickness) with 25 psi molecular hydrogen carrier gas. The samples were injected as solutions in dichloromethane with a split ratio of 10:1. Injector temperature: 250° C., detector temperature: 300° C. Oven temperature program: 50° C. (2 min) then 15° C./min to 300° C., hold 5 min.

For the determination of the isomer ratio, the hydrogenated ketones can be reacted with either (+)-diisopropyl-O, O'-bis(trimethylsilyl)-L-tartrate or (−)-diisopropyl-O,O'-bis (trimethylsilyl)-D-tartrate in the presence of trimethylsilyl triflate [Si(CH$_3$)$_3$(OSO$_2$CF$_3$)] to form the diastereomeric ketals as described in A. Knierzinger, W. Walther, B. Weber, R. K. Miller, T. Netscher, *Helv. Chim. Acta* 1990, 73, 1087-1107. The ketals can be analysed by gas chromatography using an achiral column to determine the isomer ratios. For the hydrogenated ketone 6,10-dimethylundecan-2-one, either D-(−)- or L-(+)-diisopropyltartrate can be used. For 6,10,14-trimethylpentadecan-2-one, L-(+)-diisopropyltartrate can be used to measure the quantity of the (6R,10R)-isomer that was present. D-(−)-diisopropyltartrate can be used to determine the amount of the (6S,10S)-isomer. Thus the selectivity of the stereoselective hydrogenation can be determined indirectly.

Method for Determination of Isomers:

Agilent 6890N GC with FID. Agilent CP-Sil88 for FAME column (60 m, 0.25 mm diameter, 0.20 μm film thickness) with 16 psi molecular hydrogen carrier gas. The samples were injected as solutions in ethyl acetate with a split ratio of 5:1. Injector temperature: 250° C., FID detector temperature: 250° C. Oven temperature program: 165° C. (isothermal, 240 min)

The Ir complexes indicated in the following experiments are prepared according to the disclosure in Chem. Sci., 2010, 1, 72-78.

Experiment E1-1

Separation of E/Z isomer mixtures of 6,10-dimethylundec-5-en-2-one (step a1/a2)

7.02 kg of 6,10-dimethylundec-5-en-2-one was prepared according to example 10 of DE 1 193 490 and was analysed by the GC method given above to be a 57%/43% mixture of (E)-6,10-dimethylundec-5-en-2-one and (Z)-6,10-dimethylundec-5-en-2-one (99% purity).

The mixture was distilled using separation equipment consisting of a still (volume: 9 liter) with a falling film evaporator, a rectifying column (70 mm inner diameter, height 5 m). The column was equipped with a very efficient structured packing (Sulzer). The mixture was rectified at a top pressure of approx. 5 mbar and at a column top temperature in the range from 105 to 112° C. and a bottom temperature in the still of about 125° C. The reflux ratio was adjusted to 20.

Fractions containing (Z)-6,10-dimethylundec-5-en-2-one (content of Z-isomer=99%, E-isomer <1%) as well as fractions containing (E)-6,10-dimethylundec-5-en-2-one (content of E-isomer 97%, Z-isomer <3%) were collected. At the end (E)-6,10-dimethylundec-5-en-2-one (content of E-isomer=99.5%, Z-isomer=0.5%) was found left in the still.

Experiment E1-2

Asymmetric hydrogenations of 6,10-dimethylundec-5-en-2-one (step c1/c2)

Both isomers (E)-6,10-dimethylundec-5-en-2-one ("E-DHGA") (E/Z=99.5/0.5) and (Z)-6,10-dimethylundec-5-en-2-one ("Z-DHGA") (Z/E=99/1) were hydrogenated asymmetrically, separate from each other in the following manner:

A 2 L autoclave was charged with 70 g (0.353 mol) of the specific isomer, 700 mL of 2,2,2-trifluoroethanol and a solution of the chiral iridium complex of formula (III-F) having the chirality given in table 1 at the centre indicated by * in said formula (570 mg, 0.356 mmol, 0.1 mol %) in anhydrous dichloromethane (10 g). The autoclave was closed and a pressure of 50 bar of molecular hydrogen was applied. The reaction mixture was heated to 30° C. whilst stirring for 2 hours. Afterwards the pressure was released and the solvent was removed. The product formed is (R)-6,10-dimethylundecan-2-one. The conversion as well as the amount of isomers formed is determined as indicated above and the results are given in table 1.

The products of the two separate asymmetric hydrogenations have been combined.

TABLE 1

Asymmetric hydrogenation of E-DHGA and Z-DHGA.

|  | 1 E-DHGA | 2 Z-DHGA |
|---|---|---|
| Formula of Ir complex | III-F | III-F |
| Configuration of chiral Ir complex at * | S | R |
| Amount of chiral Ir complex [mol-%] | 0.1 | 0.1 |
| Conversion | >99% | >99% |
| (R)-6,10-dimethylundecan-2-one [%] | 95.8 | 93.3 |
| (S)-6,10-dimethylundecan-2-one [%] | 4.2 | 6.7 |

Experiment E1-3

Isomerisation of 6,10-dimethylundec-5-en-2-one (step b1/b2)

In a further experiment the isomers of 6,10-dimethylundec-5-en-2-one have been separated by distillation. The E-isomer (=E-DHGA) has been isolated as having a content of (E)-6,10-dimethylundec-5-en-2-one of 95.5% (determined by GC) and the Z-isomer (=Z-DHGA) has been isolated in an enriched fraction having a content of (Z)-6,10-dimethylundec-5-en-2-one of 72.0% and a content of (E)-6,10-dimethylundeca-5,9-dien-2-one of 27.2% (total 99.2% isomers, determined by GC).

4,4'-Thiodibenzenethiol (3) was added in different concentrations (1% by weight, 3% by weight and 3% by weight) to E-DHGA or Z-DHGA, respectively. Then the mixture was stirred under argon and heated up to 140° C. and isomerized. The amount of E and Z isomers was measured by GC regularly after certain time of heating.

Figure 4:
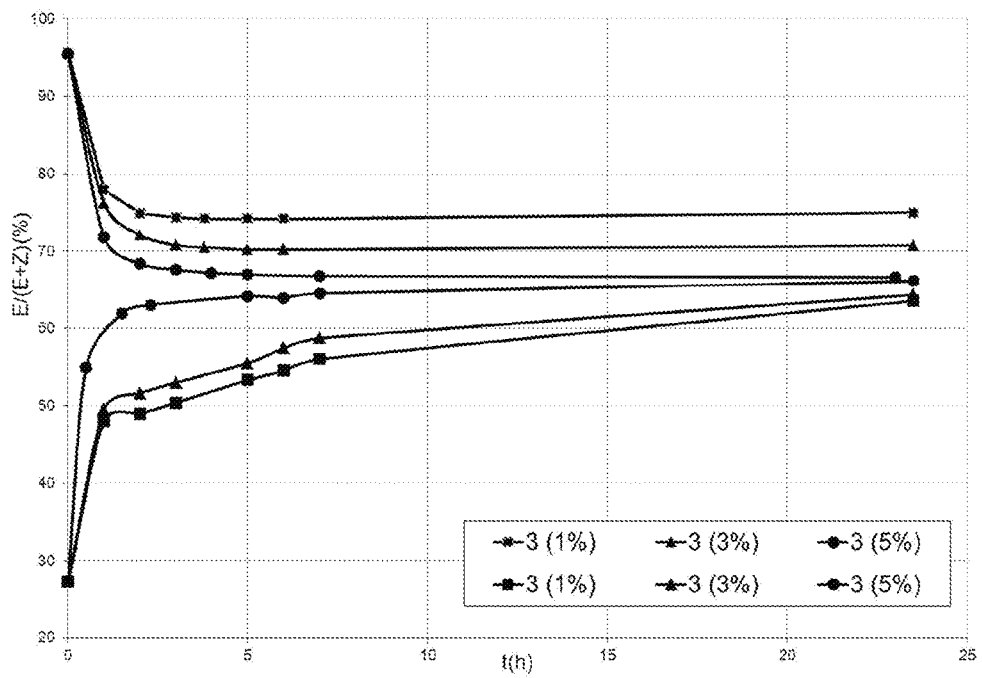

FIG. 4) shows the result of this isomerization experiments. The x-axis represents the time of heating, i.e. time of isomerization at 140° C., and the y-axis represents the percentage of E-isomer of the sum of isomers (E/(E+Z)) measured in the sample. For example a E/(E+Z) value of 80% represents a E/Z ratio of 80:20. FIG. 4) shows the effect of different concentrations of polythiols: 1% ("3 (1%)"), 3% ("3 (3%)") and 5% ("3 (5%)"). The isomerization rate depends on the concentration used. Furthermore, the FIG. 4) illustrates that that the equilibrium cis/trans ratio of 6,10-dimethylundec-5-en-2-one is at about 65% E/(E+Z).

Experiment E2-1

Separation of E/Z isomer mixtures of 6,10,14-trimethylpentadec-5-en-2-one (step a1/a2)

The mixture of (R,E)-6,10,14-trimethylpentadec-5-en-2-one and (R,Z)-6,10,14-trimethylpentadec-5-en-2-one [1.94 kg, 36% (R,Z)-6,10,14-trimethylpentadec-5-en-2-one and 49% (R,E)-6,10,14-trimethylpentadec-5-en-2-one) was fractionated using the separation equipment consisting of a still (volume: 9 liter) with a falling film evaporator, a rectifying column (70 mm inner diameter, height 5 m). The column was equipped with a very efficient structured packing (Sulzer). The rectification process was operated at a top pressure of approx. 2 mbar and at a column top temperature varied in the range from 95 to 122° C. and the bottom temperature in the still was 165° C. The reflux ratio was adjusted to 20. Fractionation of the distillate stream furnished fractions containing (R,Z)-6,10,14-trimethylpentadec-5-en-2-one (content of Z-isomer=97%). At the end (R,E)-6,10,14-trimethylpentadec-5-en-2-one was found left in the still (content of E-isomer=94%). Both isomers were further purified by fractionation and furnished fractions of both E-isomer and Z-isomer each with a purity of 99.5%)

Experiment E2-2

Asymmetric hydrogenations of (R,E)-6,10,14-trimethyl pentadec-5-en-2-one and (R,Z)-6,10,14-trimethylpentadec-5-en-2-one (step c1/c2)

Both isomers (R,E)-6,10,14-trimethylpentadec-5-en-2-one ("R,E-THFA") (E/Z=99.5/0.5, R/S=92/8) and (R,Z)-6,10,14-trimethylpentadec-5-en-2-one ("R,Z-THFA") (Z/E=99.5/0.5, R/S=92/8) were hydrogenated asymmetrically, separate from each other in the following manner:

A 125 mL autoclave was charged with 7.0 g (26 mmol) of the specific isomer, 50 mL of 2,2,2-trifluoroethanol and a solution of the chiral iridium complex of formula (III-F) having the chirality given in table 2 at the centre indicated by * in said formula (42 mg, 0.026 mmol, 0.1 mol %) in anhydrous dichloromethane (4 g). The autoclave was closed and a pressure of 50 bar of molecular hydrogen was applied. The reaction mixture was heated to 30° C. whilst stirring for 16 hours. Afterwards the pressure was released and the solvent removed. The product formed is (6R,10R)-6,10,14-trimethylpentadecan-2-one. The conversion as well as the amount of isomers formed is given in table 2.

The products of the two separate asymmetric hydrogenations have been combined.

In a further experiment in an autoclave 0.25 mmol of (R,E)-6,10,14-trimethylpentadec-5-en-2-one ("R,E-THFA") and 1 mol-%, of the Ir complex of the formula (III-D) and 1.25 ml of absolute (dry) dichloromethane were put. The autoclave was closed and a pressure of 50 bar of hydrogen was applied. Under stirring the reaction solution was kept at room temperature for 14 hours. Afterwards the pressure was released and the solvent removed. For determining the conversion the crude product was analysed by achiral gas chromatography without any further purification. The amount for the isomers has been determined using the above method and given in table 2.

TABLE 2

Asymmetric hydrogenation of R,E-THFA and R,Z-THFA.

|  | 3 R,Z-THFA | 4 R,E-THFA | 5 R,E-THFA |
|---|---|---|---|
| Formula of Ir-complex | III-F | III-F | III-D |
| Configuration of chiral Ir-complex | R | S | S |
| Amount of chiral Ir complex [mol-%] | 0.1 | 0.1 | 1 |
| Conversion | >99% | >99% | 100% |
| (6R,10R)-6,10,14-trimethylpentadecan-2-one [%] | 87.0 | 88.4 | 97.0 |
| (6S,10R)-6,10,14-trimethylpentadecan-2-one [%] | 5.3 | 3.7 | 1.8 |

TABLE 2-continued

Asymmetric hydrogenation of R,E-THFA and R,Z-THFA.

|  | 3 R,Z-THFA | 4 R,E-THFA | 5 R,E-THFA |
|---|---|---|---|
| (6R,10S)-6,10,14-trimethylpentadecan-2-one [%] | 7.7 | 7.9 | 1.2* |
| (6S,10S)-6,10,14-trimethylpentadecan-2-one [%] | 0.0 | 0.0 |  |

*(6R,10S) and (6S,10S) isomers determined as sum.

Experiment E2-3

Isomerisation of (R)-6,10,14-trimethylpentadec-5-en-2-one (step b1/b2)

In a further experiment the isomers of (R)-6,10,14-trimethylpentadec-5-en-2-one have been separated by distillation. The E-isomer has been isolated as having a content of (E)-6,10,14-trimethylpentadec-5-en-2-one of 96.3% (determined by GC) and the (Z)-6,10,14-trimethylpentadec-5-en-2-one has been isolated as having a E/Z ratio of 0.1:89.3 (at 89.4% purity, determined by GC).

5% by weight of pentaerythritol tetrakis (3-mercaptopropionate) was added to the E- or Z-isomer followed by a solvent where indicated in table 3. Then the mixture was stirred and heated up to 90° C. under argon under which conditions isomerization took place. The amount of the individual isomers was measured by GC regularly after certain reaction times.

TABLE 3

Figure 5:
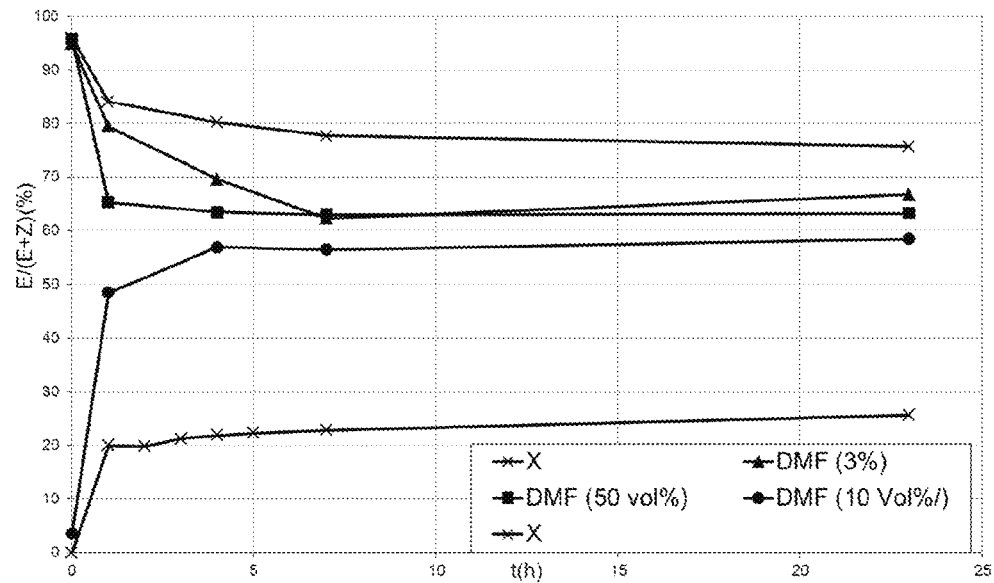

Effect of polar solvents on the isomerization efficiency of pentaerythritol tetrakis (3-mercaptopropionate) for (E)- and (Z)-6,10,14-tri-methylpentadec-5-en-2-one in FIG. 5.

| Example | Solvent | Concentration* |
|---|---|---|
| X | None | — |
| DMF (3 vol. %) | N,N-dimethylformamide | 3% by volume |
| DMF (10 vol. %) | N,N-dimethylformamide | 10% by volume |
| DMF (50 vol. %) | N,N-dimethylformamide | 50% by volume |

*concentration of solvent in ketone.

FIGS. 5a)-c) show the result of these isomerization experiments. The x-axis represents the time of heating, i.e. time of isomerization at 90° C., and the y-axis represents the percentage of E-isomer of the sum of isomers (E/(E+Z)) measured in the sample. For example a E/(E+Z) value of 80% represents a E/Z ratio of 80:20. FIG. 5a) shows the accelerating effect of DMF onto the rate of isomerization. FIG. 5b) shows the accelerating effect of 1-butyl-3-methyl-imidazolium bromide, an ionic liquid, onto the rate of isomerization. FIG. 5c) shows the accelerating effect of DMSO onto the rate of isomerization.

The FIGS. 5a)-c) indicate that the equilibrium cis/trans ratio of (E/Z)-6,10,14-trimethylpentadec-5-en-2-one is around 60-63% E/(E+Z).

Experiment E3-1

Separation of EE/ZZ/(EZ+ZE) isomer mixtures of 61014-trimethylpentadeca-5,9-di en-2-one (step a1/a2)

A sample of 6,10,14-trimethylpentadeca-5,9-dien-2-one being a mixture of (5E,9E)-I (5E,9Z)-I and (5Z,9E)-I and (5Z, 9Z)-6,10,14-trimethylpentadeca-5,9-dien-2-one was separated by fractioned distillation into a low boiling fraction of (5Z,9Z)-isomer (labelled in the following as "ZZ-isomer" or ZZ-DHFA) and a high boiling fraction of (5E,9E) isomer (labelled in the following as "EE-isomer" or EE-DHFA) and a mid boiling fraction containing both (5E,9Z)- and (5ZE, 9E)-isomer (labelled in the following as "EZ/ZE-isomer").

The mid boiling mixture (labelled in the following "EZ/ZE-isomer") of EZ- and ZE-isomers has been isolated as having a content of 93.3% of the sum of (5E,9Z)- and (5Z,9E)-6,10,14-trimethylpentadeca-5,9-dien-2-one, 3.0% (5E,9E)-6,10,14-trimethylpentadeca-5,9-dien-2-one and 1.0% of (5Z,9Z)-6,10,14-trimethylpentadeca-5,9-dien-2-one (total of 97.3% 6,10,14-trimethylpentadeca-5,9-dien-2-one isomers, measured by GC).

Experiment E3-2

Isomerization of (EZ/ZE)-isomer of 6,10,14-trimethylpentadeca-5,9-dien-2-one (b1/b2)

5% by weight of pentaerythritol tetrakis (3-mercaptopropionate) was added to EZ/ZE-isomer of the above experiment E3-1. Then the mixture was stirred and heated up to 90° C. under argon under which conditions isomerization took place. The amount of the individual isomers was measured by GC regularly after certain reaction times.

Figure 6A:
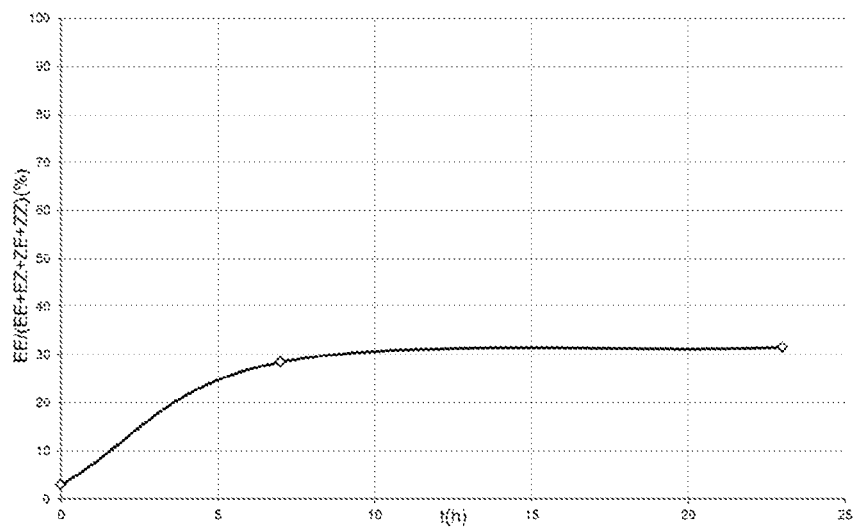
Figure 6B:
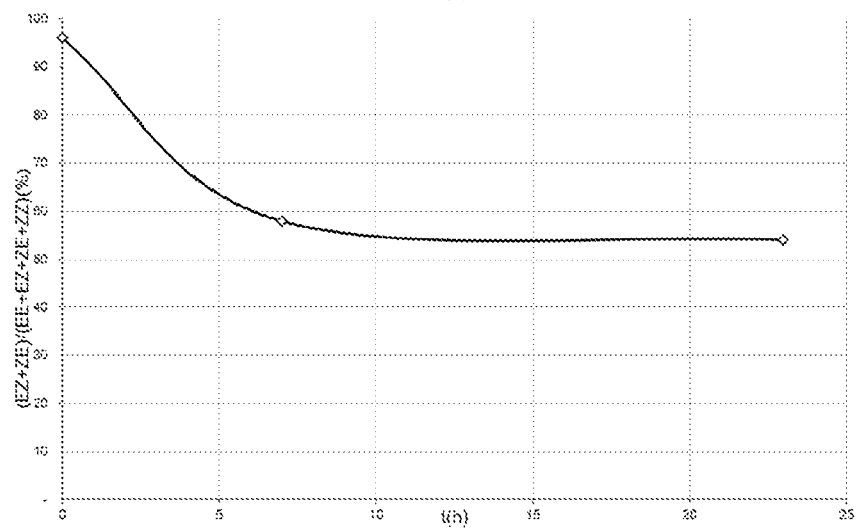
Figure 6C:
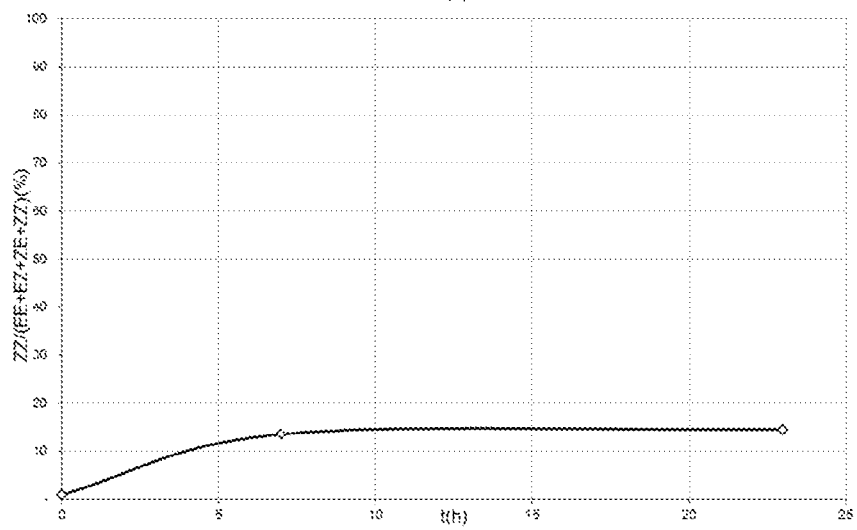

FIGS. 6a)-c) show the result of this isomerization experiment. The x-axis represents the time of heating, i.e. time of isomerization at 90° C., and the y-axis represents in FIG. 6a) the weight ratio of EE/(ZZ+EZ+ZE+EE). The y-axis represents in FIG. 6b) the weight ratio of (EZ+ZE)/(ZZ+EZ+ZE+EE). The y-axis represents in FIG. 6c) the weight ratio of ZZ/(ZZ+EZ+ZE+EE). FIGS. 6a)-c) show that all isomers are isomerized and an equilibrium is approached of at about 15% ZZ/(ZZ+EZ+ZE+EE), about 54% (EZ+ZE)/(ZZ+EZ+ZE+EE) and about 31% EE/(ZZ+EZ+ZE+EE).

Experiment E3-3

Asymmetric hydrogenations of (5E,9E)-6,10,14-trimethylpentadeca-5,9-dien-2-one and (5Z,9Z)-6,10,14-trimethylpentadeca-5,9-dien-2-one (c1/c2)

Both fractions of EE-isomer and ZZ-isomer of the above experiment E3-1 were hydrogenated asymmetrically, separate from each other in the following manner:

0.25 mmol of the corresponding isomer (EE-isomer or ZZ-isomer) of 6,10,14-trimethylpentadeca-5,9-dien-2-one 1 mol-%, of the Ir complex of the formula given in table 2 and 1.25 ml of absolute (dry) dichloromethane (DCM) or 2,2,2-trifluoroethanol (TFE) were place in an autoclave, respectively. The autoclave was closed and a pressure of 50 bar of hydrogen was applied. The reaction solution was stirred at room temperature for 12-18 hours. Afterwards the pressure was released and the solvent removed. For the determination of the conversion the crude product was analysed by achiral gas chromatography without any further purification. The amount for the isomers has been determined using the above method and given in table 4 as examples 7 to 11.

TABLE 4

| Hydrogenation of 6,10,14-trimethylpentadeca-5,9-dien-2-one | | | | | |
|---|---|---|---|---|---|
| | 6 | 7 | 8 | 9 | 10 |
| Isomer[2] | EE | ZZ | ZZ | ZZ | ZZ |
| Formula of Ir-catalyst | III-C | III-F | III-D | III-F | III-D |
| Configuration at* | S | R | R | R | R |
| Amount catalyst [mol-%] | 1 | 1 | 1 | 1 | 1 |
| Solvent | DCM | DCM | DCM | TFE | TFE |
| Conversion [%] | 100 | 100 | 100 | 100 | 100 |
| Isomer-Distribution[1] | | | | | |
| (RR) [%] | 94.5 | 96.0 | 96.6 | 96.3 | 97.2 |
| ((SS) + (RS)) [%] | 4.7 | 1.8 | 1.2 | 1.7 | 1.3 |
| (SR) [%] | 0.9 | 2.2 | 2.2 | 2.0 | 1.6 |

[1](SS) stands for the (6S,10S)-isomer, (RR) stands for the (6R,10R)-isomer, (SR) stands for the (6S,10R)-isomer, (RS) stands for the (6R,10S)-isomer of 6,10,14-trimethylpentadecan-2-one.
[2]EE stands for EE-isomer and ZZ stands for ZZ-isomer of experiment E3-1

Experiment E4

Preparation of Ketals a) Preparation of Dimethyl Ketals

The corresponding ketone as indicated in tables 5a or 5b was added to trimethyl orthoformate (50.8 mL, 49.2 g, 451 mmol, 2.65 eq.) and cooled to 5° C. Sulfuric acid (96%, 32.3 mg, 0.29 mmol, 0.2 mol %) in MeOH (16 mL) was added within 5 min. Subsequently, the reaction was heated to reflux (65° C. IT) for 3 h. After cooling, thin layer chromatography (TLC) analysis indicated full conversion. NaOMe (0.24 mL of a 25% solution in MeOH) was added to neutralize the acid. The mixture was concentrated in vacuo and subsequently diluted with hexane (50 mL). The developed precipitate was filtered off and the filtrate was concentrated. The crude product was purified by distillation, furnishing the desired dimethyl ketal.

The characterization of the ketal is given in detail hereafter.

TABLE 5a

Preparation of dimethyl ketals of 6,10-dimethylundeca-5,9-dien-2-one and 6,10-dimethylundec-5-en-2-one.

| | E-GA-DM | Z-GA-DM | E-DHGA-DM | Z-DHGA-DM |
|---|---|---|---|---|
| Ketone | (E)-6,10-dimethylundeca-5,9-dien-2-one | (Z)-6,10-dimethylundeca-5,9-dien-2-one | (E)-6,10-dimethylundec-5-en-2-one | (Z)-6,10-dimethylundec-5-en-2-one |
| Ketal | (E)-10,10-dimethoxy-2,6-dimethylundeca-2,6-diene | (Z)-10,10-dimethoxy-2,6-dimethylundeca-2,6-diene | (E)-2,2-dimethoxy-6,10-dimethylundec-5-ene | (Z)-2,2-dimethoxy-6,10-dimethylundec-5-ene |

TABLE 5a-continued

Preparation of dimethyl ketals of 6,10-dimethylundeca-5,9-dien-2-one and 6,10-dimethylundec-5-en-2-one.

|  | E-GA-DM | Z-GA-DM | E-DHGA-DM | Z-DHGA-DM |
|---|---|---|---|---|
| Yield [%] | 87 | 73 | 91 | 98 |
| E/Z | 99.4/0.6 | 1.6/98.4 | 95.4/4.6 | 0.4/99.6 |

TABLE 5b

Preparation of dimethyl ketals of 6,10,14-trimethylpentadeca-5,9,13-trien-2-one and 6,10,14-trimethylpentadeca-5,9-dien-2-one.

|  | EE-FA-DM | EE-DHFA-DM | ZZ-DHFA-DM |
|---|---|---|---|
| Ketone | (5E,9E)-6,10,14-trimethyl-pentadeca-5,9,13-trien-2-one | (5E,9E)-6,10,14-trimethylpentadeca-5,9-dien-2-one | (5Z,9Z)-6,10,14-trimethylpentadeca-5,9-dien-2-one |
| Ketal | (6E,10E)-14,14-dimethoxy-2,6,10-trimethyl-pentadeca-2,6,10-triene | (5E,9E)-2,2-dimethoxy-6,10,14-trimethylpentadeca-5,9-diene | (5Z,9Z)-2,2-dimethoxy-6,10,14-trimethylpentadeca-5,9-diene |
| Yield [%] | 95 | 90 | 56 |
| Purity[1] | 95.1 | 99.0 | 96.5 |

[1]Purity determined by quantitative $^1$H-NMR.

Characterization Data:

(E)-10,10-dimethoxy-2,6-dimethylundeca-2,6-diene (E-GA-DM)

$^1$H NMR (300 MHz, CDCl$_3$): δ 1.26 (s, 3H), 1.58 (s, 3H), 1.60 (s, 3H), superimposed by 1.60-1.65 (m, 2H), 1.66 (br s, 3H), 1.92-2.09 (m, 6H), 3.17 (s, 6H), 5.02-5.14 (m, 2H) ppm.

$^{13}$C NMR (75 MHz, CDCl$_3$): δ 15.9 (1C), 17.6 (1C), 20.8 (1C), 22.8 (1C), 25.6 (1C), 26.6 (1C), 36.4 (1C), 39.6 (1C), 47.9 (2C), 101.4 (1C), 123.8 (1C), 124.2 (1C), 131.2 (1C), 135.1 (1C) ppm.

MS (EI, m/z): 240 (M$^+$, <1), 225.3 [(M-CH$_3$)$^+$, 1], 209.3 [(M-CH$_3$O)$^+$, 20], 193.3 (8), 176.2 (18), 161.2 (16), 139.2 (20), 123.2 (14), 107.2 (75), 89.2 (100), 69.2 (65), 41.1 (56).

IR (cm$^{-1}$): 2928 (m), 2857 (w), 2828 (w), 1670 (w), 1452 (m), 1376 (s), 1345 (w), 1302 (w), 1262 (w), 1222 (w), 1196 (m), 1172 (m), 1123 (s), 1102 (s), 1053 (s), 985 (w), 929 (w), 854 (s), 744 (w), 619 (w).

(Z)-10,10-dimethoxy-2,6-dimethylundeca-2,6-diene (Z-GA-DM)

$^1$H NMR (300 MHz, CDCl3): δ 1.27 (s, 3H), 1.56-1.65 (m, 5H), 1.68 (br. s, 6H), 1.96-2.09 (m, 6H), 3.17 (s, 6H), 5.11 (t, J=7.2 Hz, 2H) ppm.

$^{13}$C NMR (75 MHz, CDCl$_3$): δ 17.6 (1C), 20.9 (1C), 22.7 (1C), 23.3 (1C), 25.7 (1C), 26.6 (1C), 31.9 (1C), 36.7 (1C), 48.0 (2C), 101.4 (1C), 124.2 (1C), 124.6 (1C), 131.5 (1C), 135.4 (1C) ppm.

MS (EI, m/z): No GC-MS was obtained due to decomposition on the column.

IR (cm$^{-1}$): 2943 (m), 2858 (w), 2828 (w), 1451 (m), 1376 (m), 1348 (w), 1301 (w), 1261 (w), 1197 (m), 1172 (m), 1153 (w), 1120 (s), 1098 (s), 1053 (s), 929 (w), 854 (m), 833 (m), 745 (w), 622 (w).

(E)-2,2-dimethoxy-6,10-dimethylundec-5-ene (E-DHGA-DM)

$^1$H NMR (300 MHz, CDCl$_3$): δ 0.83 (d, J=6.6 Hz, 6H), 1.02-1.13 (m, 2H), 1.24 (s, 3H), 1.27-1.39 (m, 2H), 1.49 (tqq, J=6.4, 6.4, 6.4 Hz, 1H), superimposed by 1.53-1.63 (m, 2H), superimposed by 1.56 (s, 3H), 1.87-2.03 (m, 4H), 3.13 (s, 6H), 5.07 (tq, J=7.0, 1.4 Hz, 1H) ppm.

$^{13}$C NMR (75 MHz, CDCl$_3$): δ 16.1 (1C), 21.2 (1C), 23.0 (2C), 23.2 (1C), 26.0 (1C), 28.2 (1C), 36.9 (1C), 39.0 (1C), 40.2 (1C), 48.3 (2C), 101.8 (1C), 124.0 (1C), 135.9 (1C) ppm.

MS (EI, m/z): No GC-MS was obtained due to decomposition on the column.

IR (cm$^{-1}$): 2953 (s), 2931 (s), 2870 (m), 2828 (m), 2108 (w), 1668 (w), 1460 (m), 1377 (s), 1367 (m), 1345 (w), 1301 (w), 1262 (m), 1221 (m), 1198 (m), 1172 (s), 1119 (s), 1100 (s), 1077 (s), 1053 (s), 967 (w), 927 (w), 854 (w), 796 (w), 739 (w), 620 (w).

(Z)-2,2-dimethoxy-6,10-dimethylundec-5-ene (Z-DHGA-DM)

$^1$H NMR (300 MHz, CDCl$_3$): δ 0.88 (d, J=6.6 Hz, 6H), 1.12-1.21 (m, 2H), 1.28 (s, 3H), 1.32-1.43 (m, 2H), 1.53 (dspt, J=6.6, 6.6 Hz, 1H), 1.57-1.66 (m, 2H), 1.68 (q, J=1.1 Hz, 3H), 1.94-2.06 (m, 4H), 3.18 (s, 6H), 5.10 (t, J=6.8 Hz, 1H) ppm.

$^{13}$C NMR (75 MHz, CDCl$_3$): δ 20.9 (1C), 22.6 (2C), 22.7 (1C), 23.3 (1C), 25.8 (1C), 27.9 (1C), 31.9 (1C), 36.8 (1C), 38.9 (1C), 48.0 (2C), 101.5 (1C), 124.3 (1C), 135.9 (1C) ppm.

MS (EI, m/z): No GC-MS was obtained due to decomposition on the column.

IR (cm$^{-1}$): 2953 (s), 2870 (w), 2828 (w), 1461 (w), 1376 (m), 1301 (w), 1261 (w), 1205 (w), 1172 (m), 1119 (m), 1097 (m), 1074 (m), 1053 (s), 1022 (w), 927 (w), 854 (m), 738 (w), 621 (w).

(5E,9E)-6,10,14-trimethyl-pentadeca-5,9,13-trien-2-one (EE-FA-DM)

$^1$H-NMR (300.1 MHz, CDCl$_3$): δ=1.28 (s, 2-CH$_3$), 1.56-1.70 (m, 4CH$_3$+CH$_2$), 1.92-2.12 (m, 10H), 3.18 (s, 2 OCH$_3$), 5.05-5.17 (m, 3H$_{olefin}$).

$^{13}$C-NMR (75.5 MHz, CDCl$_3$): δ=16.0 (2C), 17.7, 20.9, 22.8, 25.7, 26.6, 26.8, 36.5, 39.67, 39.72, 48.0 (2 OCH$_3$), 101.5 (C-2), 123.8 and 124.2 and 124.4 (3C$_{olefin}$), 131.3 and 135.0 and 135.3 (3C$_{olefin}$).

IR (ATR, cm$^{-1}$): 2924s, 2856w, 2828w, 1668m, 1450s, 1376s, 1346w, 1302m, 1261m, 1222m, 1196m, 1172m, 1153w, 1123s, 1053s, 985w, 929w, 854s, 744m, 620w

MS (m/z): 308 (M$^+$, 0.1%), 293 [(M-15)$^+$, 0.2], 276 [(M-CH$_3$OH)$^+$, 6], 244 [(M-2CH$_3$OH)$^+$, 4], 207 [(M-CH$_3$OH—C$_5$H$_9$)$^+$, 11], 175 [(M-2CH$_3$OH—C$_5$H$_9$)$^+$, 19], 107 [(M-2CH$_3$OH-2C$_5$H$_9$+H)$^+$, 71], 69 (C$_5$H$_9^+$, 100).

(5E,9E)-6,10,14-trimethylpentadeca-5,9-dien-2-one (EE-DHFA-DM)

$^1$H NMR (300 MHz, CDCl$_3$): δ 0.87 (d, J=6.6 Hz, 6H), 1.06-1.17 (m, 2H), 1.28 (s, 3H), 1.31-1.42 (m, 2H), 1.53 (tqq, J=6.6, 6.6, 6.6 Hz, 1H), superimposed by 1.58 (s, 3H), superimposed by 1.58-1.65 (m, 2H), superimposed by 1.62 (s, 3H), 1.90-2.11 (m, 8H), 3.18 (s, 6H), 5.06-5.15 (m, 2H) ppm.

$^{13}$C NMR (75 MHz, CDCl$_3$): δ 16.3 (1C), 16.4 (1C), 21.3 (1C), 23.0 (2C), 23.3 (1C), 26.2 (1C), 27.0 (1C), 28.3 (1C), 36.9 (1C), 39.0 (1C), 40.1 (1C), 40.3 (1C), 48.4 (2C), 101.9 (1C), 124.25 (1C), 124.31 (1C), 135.66 (1C), 135.71 (1C) ppm.

MS (EI, m/z): No GC-MS was obtained due to decomposition on the column.

IR (cm$^{-1}$): 2953 (m), 2930 (m), 2870 (m), 2828 (w), 1668 (w), 1457 (m), 1377 (m), 1345 (w), 1302 (w), 1262 (m), 1222 (m), 1196 (m), 1172 (m) 1123 (s), 1054 (s), 929 (w), 854 (s), 739 (w), 620 (w).

(5Z,9Z)-6,10,14-trimethylpentadeca-5,9-dien-2-one (ZZ-DHFA-DM)

$^1$H NMR (300 MHz, CDCl$_3$): δ 0.88 (d, J=6.6 Hz, 6H), 1.11-1.21 (m, 2H), 1.28 (s, 3H), 1.30-1.43 (m, 2H), 1.54 (qq, J=6.6 Hz, 1H), superimposed by 1.57-1.66 (m, 2H), 1.67 (br s, 3H), 1.69 (q, J=1.3 Hz, 3H), 1.94-2.10 (m, 8H), 3.18 (s, 6H), 5.12 (t, J=6.4 Hz, 2H) ppm.

$^{13}$C NMR (75 MHz, CDCl$_3$): δ 20.9 (1C), 22.3 (1C), 22.6 (1C), 22.7 (1C), 23.39 (1C), 23.40 (1C), 25.8 (1C), 26.3 (1C), 27.9 (1C), 31.9 (1C), 32.2 (1C), 36.7 (1C), 38.9 (1C), 48.0 (2C), 101.4 (1C), 124.6 (1C), 124.7 (1C), 135.4 (1C), 135.8 (1C) ppm.

MS (EI, m/z): No GC-MS was obtained due to decomposition on the column.

IR (cm$^{-1}$): 2953 (m), 2870 (m), 2828 (w), 1454 (m), 137 (m), 1302 (w), 1261 (m), 1201 (m), 1172 (m), 1152 (m), 1098 (m), 1054 (s), 854 (s), 749 (w), 622 (w).

b) Preparation of Ethylene Glycol Ketals

Under nitrogen, a reaction vessel was charged with glycol (112 mL, 125 g, 2.1 mol), p-toluenesulfonic acid monohydrate (0.150 g, 0.5774 mmol) and 0.5 mol either of (E)-6,10-dimethylundec-5-en-2-one or (Z)-6,10-dimethylundec-5-en-2-one. The mixture was allowed to stir at ambient temperature for 5 hours at reduced pressure (0.39 mbar). While maintaining the low pressure, the temperature was slowly increased to 40° C. At conversion of larger than 95% of the ketone, the temperature was further increased allowing a gentle distillation of glycol and continued until a conversion of more than 99% was achieved.

At room temperature, the product was extracted by a solution of triethylamine in heptane (2 mL triethylamine/L heptane). The glycol phase was separated and the heptane layer was washed with a NaHCO$_3$ solution in water. Separation of the heptane phase, drying over anhydrous Na$_2$SO$_4$, filtration and removal of the solvent in vacuo gave the crude ketal. The ketal was further purified by means of distillation. The corresponding ketal was identified by $^1$H-NMR.

TABLE 5c

Preparation of ethylene glycol ketals.

| | E-DHGA-en | Z-DHGA-en |
|---|---|---|
| Ketone | (E)-6,10-dimethylundec-5-en-2-one | (Z)-6,10-dimethylundec-5-en-2-one |
| Ketal | (E)-2-(4,8-dimethylnon-3-en-1-yl)-2-methyl-1,3-dioxolane | (Z)-2-(4,8-dimethylnon-3-en-1-yl)-2-methyl-1,3-dioxolane |
| Yield [%] | 88 | 87 |

Characterization Data

(E)-2-(4,8-dimethylnon-3-en-1-yl)-2-methyl-1,3-dioxolane (E-DHGA-en)

$^1$H NMR (300 MHz, CDCl$_3$) δ 5.12 (t, 1H), 3.95 (m, 4H), 2.2-2 (m, 2H), 1.94 (t, 2H), 1.8-1.3 (m, 11H), 1.2-1.0 (m, 2H), 0.87 (d, 6H) ppm.

(Z)-2-(4,8-dimethylnon-3-en-1-yl)-2-methyl-1,3-dioxolane (Z-DHGA-en)

$^1$H NMR (300 MHz, CDCl$_3$) δ 5.12 (t, 1H), 3.94 (m, 4H), 2.15-1.9 (m, 4H), 1.7-1.45 (m, 6H), 1.44-1.27 (m, 5H), 1.23-1.08 (m, 2H), 0.88 (d, 6H) ppm.

c) Preparation of Neopentyl Glycol Ketals

The ketone (90.7 mmol) indicated in tables 5d or 5e, 2,2-dimethyl-1,3-propanediol (neopentylglycol, 32.4 g, 283 mmol, 3.4 eq.) and p-toluene sulfonic acid monohydrate (60 mg, 0.31 mmol, 0.3 mol %) were suspended in toluene (300 mL). The reaction was heated to 90° C. upon which a homogeneous solution formed. Subsequently, at 75° C., vacuum was applied cautiously (first 63 mbar, then 24 mbar) in order to slowly distill toluene off (approx. 100 mL over 4 h). After 4 h, thin layer chromatography (TLC) analysis indicated full conversion of the ketone. The reaction was allowed to cool to room temperature and diluted with heptane (300 mL) upon which excess neopentylglycol precipitated. The precipitate was filtered off (17.4 g wet). The filtrate was treated with Et$_3$N (1 mL), subsequently washed with aqueous NaHCO$_3$ solution (2.4% w/w, 2×300 mL), dried over MgSO$_4$ and concentrated in vacuo. The crude product was purified by distillation, furnishing the desired neopentyl ketal. The characterization of the ketal is given in detail hereafter.

TABLE 5d

Preparation of neopentyl glycol ketals.

| | E-GA-neo | Z-GA-neo | E-DHGA-neo | Z-DHGA-neo |
|---|---|---|---|---|
| Ketone | (E)-6,10-dimethylundeca-5,9-dien-2-one | (Z)-6,10-dimethylundeca-5,9-dien-2-one | (E)-6,10-dimethylundec-5-en-2-one | (Z)-6,10-dimethylundec-5-en-2-one |

TABLE 5d-continued

Preparation of neopentyl glycol ketals.

|  | E-GA-neo | Z-GA-neo | E-DHGA-neo | Z-DHGA-neo |
|---|---|---|---|---|
| Ketal | (E)-2-(4,8-di-methylnona-3,7-dien-1-yl)-2,5,5-trimethyl-1,3-dioxane | (Z)-2-(4,8-di-methylnona-3,7-dien-1-yl)-2,5,5-trimethyl-1,3-dioxane | (E)-2-(4,8-di-methylnon-3-en-1-yl)-2,5,5-trimethyl-1,3-dioxane | (Z)-2-(4,8-di-methylnon-3-en-1-yl)-2,5,5-trimethyl-1,3-dioxane |
| Yield [%] | 78 | 87 | 89 | 84 |
| E/Z | 99.4/0.6 | 1.7/98.3 | 95.3/4.7 | 1.6/98.4 |

TABLE 5e

Preparation of neopentyl glycol ketals of 6,10,14-trimethylpenta-deca-5,9-dien-2-one.

|  | EE-DHFA-neo | ZZ-DHFA-neo |
|---|---|---|
| Ketone | (5E,9E)-6,10,14-trimethyl-pentadeca-5,9-dien-2-one | (5Z,9Z)-6,10,14-trimethylpenta-deca-5,9-dien-2-one |
| Ketal | 2,5,5-trimethyl-2-((3E,7E)-4,8,12-trimethyltrideca-3,7-dien-1-yl)-1,3-dioxane | 2,5,5-trimethyl-2-((3Z,7Z)-4,8,12-trimethyltrideca-3,7-dien-1-yl)-1,3-dioxane |
| Yield [%] | 81 | 70 |
| EE/(ZE + ZE)/ZZ | 97.0/3.0/0.0 | 0.0/2.5/97.5 |

Characterization Data (E)-2-(4,8-dimethylnona-3,7-dien-1-yl)-2,5,5-trimethyl-1,3-dioxane (E-GA-neo)

$^1$H NMR (300 MHz, CDCl$_3$): δ 0.92 (s, 3H), 0.99 (s, 3H), 1.37 (s, 3H), 1.59 (s, 3H), 1.61 (s, 3H), 1.67 (s, 3H), 1.68-1.75 (m, 2H), 1.94-2.15 (m, 6H), AB signal (δ$_A$=3.46, δ$_B$=3.52, J$_{AB}$=11.3 Hz, 4H), 5.05-5.17 (m, 2H) ppm.
$^{13}$C NMR (75 MHz, CDCl$_3$): δ 15.9 (1C), 17.6 (1C), 20.8 (1C), 22.0 (1C), 22.6 (1C), 22.7 (1C), 25.6 (1C), 26.7 (1C), 29.9 (1C), 37.3 (1C), 39.6 (1C), 70.3 (2C), 98.8 (1C), 124.1 (1C), 124.3 (1C), 131.2 (1C), 135.1 (1C) ppm.
MS (EI, m/z): 280 (M$^+$, 3), 265 [(M-CH$_3$)$^+$, 14], 176 (21), 129 [(C$_7$H$_{13}$O$_2$)$^+$, 100], 69 (63), 43 (43).
IR (cm$^{-1}$): 2954 (m), 2925 (m), 2858 (m), 2731 (w), 1720 (w), 1669 (w), 1473 (w), 1450 (m), 1394 (m), 1372 (m), 1349 (w), 1306 (w), 1271 (w), 1249 (m), 1211 (m), 1186 (m), 1123 (s), 1088 (s), 1043 (m), 1021 (m), 984 (w), 950 (w), 925 (w), 907 (w), 862 (w), 837 (w), 792 (w), 742 (w), 677 (w), 667 (w).

(Z)-2-(4,8-dimethylnona-3,7-dien-1-yl)-2,5,5-trimethyl-1,3-dioxane (Z-GA-neo)

$^1$H NMR (300 MHz, CDCl$_3$): δ 0.91 (s, 3H), 0.97 (s, 3H), 1.35 (s, 3H), 1.60 (s, 3H), 1.64-1.74 (m, 5H) superimposed by 1.67 (br s, 3H), 1.99-2.18 (m, 6H), AB signal (δ$_A$=3.44, δ$_B$=3.51, J$_{AB}$=11.3 Hz, 4H), 5.07-5.16 (m, 2H) ppm.
$^{13}$C NMR (75 MHz, CDCl$_3$): δ 17.5 (1C), 20.9 (1C), 21.3 (1C), 21.9 (1C), 22.5 (1C), 22.6 (1C), 23.3 (1C), 25.7 (1C), 26.6 (1C), 29.9 (1C), 31.8 (1C), 37.5 (1C), 70.3 (2C), 98.7 (1C), 124.3 (1C), 124.9 (1C), 131.4 (1C), 135.2 (1C) ppm.
MS (EI, m/z): 280 (M$^+$, 3), 265 [(M-CH$_3$)$^+$, 13], 176 (19), 129 [(C$_7$H$_{13}$O$_2$)$^+$, 100], 107 (15), 69 (62), 43 (39).
IR (cm$^{-1}$): 2954 (m), 2927 (m), 2858 (m), 2729 (w), 1721 (w), 1671 (w), 1473 (m), 1450 (m), 1394 (m), 1374 (m), 1349 (w), 1315 (w), 1271 (m), 1249 (m), 1211 (m), 1187 (m), 1149 (w), 1120 (s), 1086 (s), 1043 (m), 1021 (m), 985 (w), 951 (m), 925 (w), 907 (m), 857 (m), 833 (m), 792 (w), 743 (w), 677 (w), 667 (w).

(E)-2-(4,8-dimethylnon-3-en-1-yl)-2,5,5-trimethyl-1,3-dioxane (E-DHGA-neo)

$^1$H NMR (300 MHz, CDCl$_3$): δ 0.87 (d, J=6.6 Hz, 6H), 0.93 (s, 3H), 1.00 (s, 3H), 1.06-1.22 (m, 2H), 1.31-1.43 (m, 2H) superimposed by 1.38 (s, 3H), 1.53 (tqq, J=6.6, 6.6, 6.6 Hz, 1H), 1.61 (br s, 3H), 1.65-1.77 (m, 2H), 1.94 (t, J=7.5 Hz, 2H), 2.05-2.17 (m, 2H), AB signal (δ$_A$=3.46, δ$_B$=3.54, J$_{AB}$=11.4 Hz, 4H), 5.13 (tq, J=7.1, 1.1 Hz, 1H) ppm.
$^{13}$C NMR (75 MHz, CDCl$_3$): δ 15.8 (1C), 20.9 (1C), 22.0 (1C), 22.59 (1C), 22.63 (2C), 22.7 (1C), 25.7 (1C), 27.9 (1C), 29.9 (1C), 37.3 (1C), 38.6 (1C), 39.9 (1C), 70.3 (2C), 98.8 (1C), 123.8 (1C), 135.6 (1C) ppm.
MS (EI, m/z): 282 (M$^+$, 5), 267 [(M-CH$_3$)$^+$, 10], 129 (100), 95 (14), 69 (36), 43 (32).
IR (cm$^{-1}$): 2953 (s), 2929 (m), 2868 (m), 1720 (w), 1468 (m), 1394 (m), 1381 (m), 1368 (m), 1349 (w), 1306 (w), 1270 (w), 1250 (m), 1211 (m), 1187 (w), 1118 (s), 1087 (s), 1066 (m), 1044 (m), 1022 (m), 950 (m), 925 (w), 907 (m), 862 (m), 791 (w), 739 (w), 677 (w), 666 (w).

(Z)-2-(4,8-dimethylnon-3-en-1-yl)-2,5,5-trimethyl-1,3-dioxane (Z-DHGA-neo)

$^1$H NMR (300 MHz, CDCl$_3$): δ 0.87 (d, J=6.6 Hz, 6H), 0.93 (s, 3H), 0.97 (s, 3H), 1.10-1.20 (m, 2H), 1.34-1.41 (m, 3H) superimposed by 1.36 (s, 3H), 1.53 (tqq, J 15=6.6, 6.6, 6.6 Hz, 1H), 1.64-1.75 (m, 2H) superimposed by 1.67 (q, J=1.5 Hz, 3H), 1.95-2.15 (m, 4H), AB signal (δ$_A$=3.46, δ$_B$=3.51, J$_{AB}$=11.1 Hz, 4H), 5.12 (br t, J=7.2 Hz, 1H)
$^{13}$C NMR (75 MHz, CDCl$_3$): δ 21.1 (1C), 22.0 (1C), 22.61 (3C), 22.65 (1C), 23.4 (1C), 25.7 (1C), 27.9 (1C), 29.9 (1C), 31.9 (1C), 37.2 (1C), 38.8 (1C), 70.3 (2C), 98.8 (1C), 124.6 (1C), 135.8 (1C) ppm.
MS (EI, m/z): 282 (M$^+$, 6), 267 [(M-CH$_3$)$^+$, 11], 129 (100), 95 (14), 69 (35), 43 (32).
IR (cm$^{-1}$): 2953 (s), 2867 (m), 1722 (w), 1468 (m), 1394 (m), 1368 (m), 1349 (w), 1306 (w), 1270 (w), 1250 (m), 1211 (m), 1189 (w), 1116 (s), 1086 (s), 1043 (m), 1022 (m), 951 (m), 925 (w), 907 (m), 856 (m), 792 (w), 739 (w), 677 (w), 667 (w).

2,5,5-trimethyl-2-((3E,7E)-4,8,12-trimethyltrideca-3,7-dien-1-yl)-1,3-dioxane (EE-DHFA-neo)

$^1$H NMR (300 MHz, CDCl$_3$): δ 0.86 (d, J=6.6 Hz, 6H), 0.92 (s, 3H), 0.99 (s, 3H), 1.05-1.22 (m, 2H), 1.37 (s, 3H), superimposed by 1.31-1.42 (m, 2H), 1.52 (tqq, J=6.6, 6.6, 6.6 Hz, 1H), 1.57 (s, 3H), 1.61 (s, 3H), 1.67-1.76 (m, 2H), 1.88-2.16 (m, 8H), AB signal ($\delta_A$=3.45, $\delta_B$=3.52, $J_{AB}$=11.3 Hz, 4H), 5.05-5.17 (m, 2H) ppm.

$^{13}$C NMR (75 MHz, CDCl$_3$): δ 15.85 (1C), 15.92 (1C), 20.9 (1C), 22.0 (1C), 22.55 (1C), 22.62 (2C), 22.68 (1C), 25.7 (1C), 26.5 (1C), 27.8 (1C), 29.9 (1C), 37.3 (1C), 38.6 (1C), 39.7 (1C), 39.9 (1C), 70.3 (2C), 98.8 (1C), 123.9 (1C), 124.1 (1C), 135.1 (1C), 135.2 (1C) ppm.

MS (EI, m/z): 350 (M$^+$, 4), 335 [(M-CH$_3$)$^+$, 11], 246 (10), 206 (10), 161 (9), 129 (100), 107 (13), 69 (38), 43 (32).

IR (cm$^{-1}$): 2953 (s), 2928 (s), 2867 (m), 1462 (m), 1394 (m), 1382 (m), 1368 (m), 1305 (w), 1271 (w), 1249 (m), 1211 (m), 1187 (m), 1123 (s), 1087 (s), 1043 (m), 1021 (m), 950 (w), 925 (w), 907 (w), 862 (m) 791 (w), 739 (w), 678 (w).

2,5,5-trimethyl-2 ((3E,7E)-4,8,12-trimethyltrideca-3, 7-dien-1-yl)-1,3-dioxane (ZZ-DHFA-neo)

$^1$H NMR (300 MHz, CDCl$_3$): δ 0.87 (d, J=6.8 Hz, 6H), 0.92 (s, 3H), 0.98 (s, 3H), 1.10-1.21 (m, 2H), 1.29-1.42 (m, 2H), superimposed by 1.36 (s, 3H), 1.53 (qqt, J=6.7, 6.7, 6.7 Hz, 1H), 1.66 (br. s, 3H), 1.68 (q, J=1.4 Hz, 3H), 1.67-1.75 (m, 2H), 1.99 (t, J=7.7 Hz, 2H), 2.02-2.16 (m, 6H), AB signal ($\delta_A$=3.45, $\delta_B$=3.52, $J_{AB}$=11.5 Hz, 4H), 5.02-5.22 (m, 2H) ppm.

$^{13}$C NMR (75 MHz, CDCl$_3$): δ 20.9 (1C), 21.9 (1C), 22.6 (3C), 22.7 (1C), 23.38 (1C), 23.42 (1C), 25.8 (1C), 26.3 (1C), 27.9 (1C), 29.9 (1C), 31.9 (1C), 32.1 (1C), 37.4 (1C), 38.9 (1C), 70.3 (2C), 98.8 (1C), 124.7 (1C), 125.0 (1C), 135.2 (1C), 135.6 (1C) ppm.

MS (EI, m/z): 350 (M$^+$, 5), 335 [(M-CH$_3$)$^+$, 10], 246 (8), 206 (8), 151 (7), 129 (100), 107 (10), 69 (35), 43 (27).

IR (cm$^{-1}$): 2953 (s), 2867 (m), 1452 (m), 1394 (w), 1372 (m), 1315 (w), 1271 (w), 1249 (m), 1211 (m), 1189 (w), 1119 (s), 1087 (s), 1043 (m), 1021 (m), 951 (w), 925 (w), 907 (w), 856 (m) 792 (w), 737 (w), 668 (w).

d) Preparation of bis(trifluoroethyl) Ketals

A 250 mL three-necked flask with stir bar was dried under high vacuum (heat gun at 250° C.), then allowed to cool, flushed with argon and charged with 1,1,1 trifluoroethanol (TFE) (40 mL) under argon. The flask was cooled with an ice-bath while trimethylaluminum (2 M in heptane, 20.0 mL, 40.0 mmol, 1.95 eq.) was added dropwise within 60 min, keeping the temperature below 22° C. The two-phase (TFE/heptane) mixture became clear again after a few minutes and was allowed to stir for an additional 20 min at room temperature. 20.7 mmol of the dimethyl ketal of the corresponding ketone as indicated in tables 5f or 5g, being prepared as shown above, was added dropwise within 5 min at room temperature. After 1.5 h, GC analysis indicated full conversion of starting material. The reaction was quenched with a half-saturated solution of potassium sodium tartrate in water (100 mL), stirred for 2 h at room temperature and finally diluted with n-hexane (200 mL). The organic phase was separated, extracted with n-hexane (2×100 mL), dried over MgSO$_4$ and concentrated. The crude product was purified by column chromatography (neutral aluminium oxide, eluent: n-hexane). The characterization of the ketal is given in detail hereafter.

TABLE 5f

Preparation of bis(trifluoroethyl) ketals of 6,10-dimethylundeca-5,9-dien-2-one and 6,10-dimethylundec-5-en-2-one.

| | E-GA-tfe | E-DHGA-tfe |
|---|---|---|
| Dimethylketal (reactant) | E-GA-DM | E-DHGA-DM |

TABLE 5f-continued

Preparation of bis(trifluoroethyl) ketals of 6,10-dimethylundeca-5,9-dien-2-one and 6,10-dimethylundec-5-en-2-one.

| | E-GA-tfe | E-DHGA-tfe |
|---|---|---|
| Ketal | (E)-2,6-dimethyl-10,10-bis(2,2,2-trifluoroethoxy)undeca-2,6-diene | (E)-6,10-dimethyl-2,2-bis(2,2,2-trifluoroethoxy)undec-5-ene |
| Yield [%] | 85 | 74 |
| E/Z | 99.4/0.6 | 95.0/5.0 |

TABLE 5g

Preparation of bis(trifluoroethyl) ketals of (5E,9E)-6,10,14-trimethylpentadeca-5,9,13-trien-2-one and (5E,9E)-6,10,14-trimethylpentadeca-5,9-dien-2-one.

| | EE-FA-tfe | EE-DHFA-tfe |
|---|---|---|
| Dimethylketal (reactant) | (6E,10E)-14,14-dimethoxy-2,6,10-trimethylpentadeca-2,6,10-triene | (5E,9E)-2,2-dimethoxy-6,10,14-trimethylpentadeca-5,9-diene |
| Ketal | (6E,10E)-2,6,10-trimethyl-14,14-bis(2,2,2-trifluoroethoxy)-pentadeca-2,6,10-triene | (5E,9E)-6,10,14-trimethyl-2,2-bis(2,2,2-trifluoroethoxy)pentadeca-5,9-diene |
| Yield [%] | 71 | 83 |
| EE/(ZE + ZE + ZZ) | 99/1 | 95/5 |

Characterization Data (E)-2,6-dimethyl-10,10-bis(2,2,2-trifluoroethoxy) undeca-2,6-diene (E-GA-tfe)

$^1$H NMR (300 MHz, CDCl$_3$): δ 1.41 (s, 3H), 1.62 (br s, 6H), 1.67-1.76 (m, 2H), superimposed by 1.69 (q, J=0.9 Hz, 3H), 1.93-2.15 (m, 6H), 3.73-3.97 (m, 4H), 5.02-5.18 (m, 2H) ppm.

$^{13}$C NMR (150 MHz, CDCl$_3$): δ 15.9 (1C), 17.6 (1C), 21.3 (1C), 22.6 (1C), 25.7 (1C), 26.6 (1C), 36.9 (1C), 39.6 (1C), 59.3 (q, $J_{C,F}$=35.0 Hz, 2C), 103.4 (1C), 124.0 (q, $J_{C,F}$=275.0 Hz, 2C), 122.7 (1C), 124.1 (1C), 131.5 (1C), 136.2 (1C) ppm.

MS (EI, m/z): 361 [(M-CH$_3$)$^+$, 1], 276 [(M-TFE)$^+$, 15], 225 [(CF$_3$CH$_2$O)$_2$C—CH$_3$)$^+$, 86], 207 (20), 153 (18), 136 (58), 107 (80), 69 (100), 41 (40).

IR (cm$^{-1}$): 2927 (w), 2859 (w), 1459 (w), 1419 (w), 1385 (w), 1281 (s), 1223 (w), 1156 (s), 1133 (s), 1081 (s), 971 (s), 889 (m), 860 (w), 845 (w), 678 (w), 663 (w).

(E)-6,10-dimethyl-2,2-bis(2,2,2-trifluoroethoxy) undec-5-ene (E-DHGA-tfe)

$^1$H NMR (600 MHz, CDCl$_3$): δ 0.88 (d, J=6.8 Hz, 6H), 1.11-1.17 (m, 2H), 1.35-1.40 (m, 2H), 1.41 (s, 3H), 1.54 (qqt, J=6.7, 6.7, 6.7 Hz, 1H), 1.61 (br s, 3H), 1.69-1.73 (m, 2H), 1.95 (t, J=7.7 Hz, 2H), 2.03-2.09 (m, 2H), 3.78-3.91 (m, 4H), 5.09 (tq, J=7.1, 1.3 Hz, 1H) ppm.

$^{13}$C NMR (151 MHz, CDCl$_3$): δ 14.1 (1C), 15.8 (1C), 21.3 (1C), 22.56 (1C), 22.61 (1C), 25.6 (1C), 27.9 (1C), 37.0 (1C), 38.6 (1C), 39.8 (1C), 59.2 (q, $J_{C,F}$=35.0 Hz, 2C), 103.4 (1C), 124.0 (q, $J_{C,F}$=277.0 Hz, 2C), 122.4 (1C), 136.7 (1C) ppm.

MS (EI, m/z): 363 [(M-CH$_3$)$^+$, 1], 278 [(M-TFE)$^+$, 22], 225 [(CF$_3$CH$_2$O)$_2$C—CH$_3$)$^+$, 60], 193 (100), 153 (13), 127 (11), 83 (CF$_3$CH$_2$$^+$, 25), 69 (13), 43 (17).

IR (cm$^{-1}$): 2956 (w), 2933 (w), 2872 (w), 1462 (w), 1419 (w), 1385 (w), 1368 (w), 1281 (s), 1223 (w), 1156 (s), 1134 (s), 1081 (s), 971 (s), 889 (m), 860 (w), 845 (w), 679 (w), 663 (m).

(6E,10E)-2,6,10-trimethyl-14,14-bis(2,2,2-trifluoroethoxy)pentadeca-2,6,10-triene (EE-FA-tfe)

$^1$H NMR (300 MHz, CDCl$_3$): δ 1.41 (s, 3H), 1.61 (br s, 6H), 1.63 (br s, 3H), 1.67-1.75 (m, 2H), superimposed by 1.69 (br q, J=0.9 Hz, 3H), 1.93-2.16 (m, 10H), 3.74-3.95 (m, 4H), 5.11 (br t, J=6.5 Hz, 3H) ppm.

$^{13}$C NMR (75 MHz, CDCl$_3$): δ 15.94 (1C), 15.98 (1C), 17.6 (1C), 21.3 (1C), 22.6 (1C), 25.6 (1C), 26.5 (1C), 26.8 (1C), 37.0 (1C), 39.6 (1C), 39.7 (1C), 59.3 (q, J$_{C,F}$=34.9 Hz, 2C), 103.4 (1C), 124.0 (q, J$_{C,F}$=275.8 Hz, 2C), 122.7 (1C), 124.0 (1C), 124.3 (1C), 131.3 (1C), 135.1 (1C), 136.2 (1C) ppm.

MS (EI, m/z): 444 (M$^+$, 5), 429 [(M-CH$_3$)$^+$, 1], 344 [(M-TFE)$^+$, 4], 225 [(CF$_3$CH$_2$O)$_2$C—CH$_3$)$^+$, 54], 175 (33), 136 (28), 107 (48), 81 (53), 69 (100), 41 (34).

IR (cm$^{-1}$): 2922 (w), 2858 (w), 1457 (w), 1419 (w), 1385 (w), 1282 (s), 1223 (w), 1157 (s), 1133 (s), 1111 (m), 1081 (s), 971 (s), 889 (m), 860 (w), 845 (w), 678 (w), 663 (m).

(5E,9E)-6,10,14-trimethyl-2,2-bis(2,2,2-trifluoroethoxy)pentadeca-5,9-diene (EE-DHFA-tfe)

$^1$H NMR (300 MHz, CDCl$_3$): δ 0.88 (d, J=6.6 Hz, 6H), 1.08-1.20 (m, 2H), 1.32-1.44 (m, 2H), superimposed by 1.41 (s, 3H), 1.54 (tqq, J=6.6, 6.6, 6.6 Hz, 1H), 1.60 (br s, 3H), 1.63 (br s, 3H), 1.67-1.76 (m, 2H), 1.89-2.17 (m, 8H), 3.73-3.97 (m, 4H), 5.04-5.17 (m, 2H) ppm.

$^{13}$C NMR (75 MHz, CDCl$_3$): δ 15.89 (1C), 15.95 (1C), 21.4 (1C), 22.60 (1C), 22.61 (2C), 25.8 (1C), 26.5 (1C), 27.9 (1C), 37.0 (1C), 38.6 (1C), 39.7 (1C), 39.9 (1C), 59.3 (q, J$_{C,F}$=35.5 Hz, 2C), 103.4 (1C), 124.0 (q, J$_{C,F}$=276.0 Hz, 2C), 122.7 (1C), 123.7 (1C), 135.5 (1C), 136.2 (1C) ppm.

MS (EI, m/z): 431 [(M-CH$_3$)$^+$, 1], 346 [(M-TFE)$^+$, 13], 262 (9), 225 [(CF$_3$CH$_2$O)$_2$C—CH$_3$)$^+$, 93], 206 (43), 153 (17), 127 (24), 107 (45), 83 (CF$_3$CH$_2$$^+$, 100), 69 (51), 55 (43), 43 (28).

IR (cm$^{-1}$): 2955 (w), 2931 (w), 2871 (w), 1462 (w), 1419 (w), 1385 (m), 1282 (s), 1223 (w), 1157 (s), 1133 (s), 1080 (s), 971 (s), 889 (m), 860 (w), 845 (w), 679 (w), 663 (m).

Experiment E5

Asymmetric Hydrogenations of Ketals (Step c1/c2)

The ketals and acetals were asymmetrically hydrogenated in the following manner:

An autoclave vessel was charged under nitrogen with chiral iridium complex of formula as indicated in tables 6a-k having the configuration at the chiral centre marked by * as indicated in tables 6a-k, the ketal or acetal (conc.) as indicated in tables 6a-k, solvent as indicated in tables 6a-k. The reaction vessel was closed and pressurized with molecular hydrogen to the pressure (pH$_2$) indicated in tables 6a-k. The reaction mixture was stirred at room temperature for the time (t) as indicated in tables 6a-k under hydrogen. Then the pressure was released and the assay yield and the stereoisomer distribution of the fully hydrogenated product was determined. The catalyst loading (S/C) is defined as mmol ketal or acetal ("substrate")/mmol chiral iridium complex.

The characterization of the hydrogenated ketals/acetals is given hereafter.

TABLE 6a

Asymmetric hydrogenation of different ketals of E-6,10-dimethyl-undeca-5,9-dien-2-one (E-GA).
Conditions: 0.5 mmol ketal, 4 g solvent, pressure p(H$_2$) = 30 bar, 16 h stirring at room temperature.

| | 11 | 12 | 13 | 14 |
|---|---|---|---|---|
| Ketal/ketone | E-GA | E-GA-DM | E-GA-neo | E-GA-neo |
| Formula of Ir complex | III-F | III-F | III-F | III-F |
| Configuration of chiral Ir complex at * | (S) | (S) | (S) | (S) |
| Amount of chiral Ir complex [mol-%] | 0.5 | 0.5 | 0.5 | 0.5 |
| Solvent[1] | DCM | TFE | DCM | TFE |
| Hydrogenated ketal/ketone | R-THGA | R-THGA-DM | R-THGA-neo | R-THGA-neo |
| Conversion [%] | 100 | >99 | >99 | >99 |
| Isomer-Distribution[2,3] | | | | |
| (R) [%] | 96.5 | 95.3 | 97.5 | 98.4 |
| (S) [%] | 3.5 | 4.7 | 2.5 | 1.6 |

[1]TFE = 2,2,2-trifluoroethanol; DCM = dichloromethane
[2](R) stands for the R-isomer, (S) stands for the S-isomer of the corresponding ketal of 6,10-dimethylundecan-2-one
[3]is determined as ketone after hydrolysis of the ketal TABLE 6b Asymmetric hydrogenation of different ketals of Z-6,10-dimethyl-undeca-5,9-dien-2-one (Z-GA).
Conditions: 0.5 mmol ketal, 4 g solvent, pressure p(H$_2$) = 30 bar, 16 h stirring at room temperature.

| | 15 | 16 | 17 | 18 |
|---|---|---|---|---|
| Ketal | Z-GA-DM | Z-GA-DM | Z-GA-neo | Z-GA-neo |
| Formula of Ir complex | III-F | III-F | III-F | III-F |
| Configuration of chiral Ir complex at * | (R) | (R) | (R) | (R) |
| Amount of chiral Ir complex [mol-%] | 0.5 | 0.25 | 0.25 | 0.25 |
| Solvent[1] | DCM | TFE | DCM | TFE |
| Hydrogenated ketal | R-THGA-DM | R-THGA-DM | R-THGA-neo | R-THGA-neo |
| Conversion [%] | >99 | >99 | >99 | >99 |
| Isomer-Distribution[2,3] | | | | |
| (R) [%] | 98.2 | 98.5 | 97.9 | 98.6 |
| (S) [%] | 1.8 | 1.5 | 2.1 | 1.4 |

[1]TFE = 2,2,2-trifluoroethanol; DCM = dichloromethane
[2](R) stands for the R-isomer, (S) stands for the S-isomer of the corresponding ketal of 6,10-dimethylundecan-2-one
[3]is determined as ketone after hydrolysis of the ketal TABLE 6c Asymmetric hydrogenation of different ketals of E-DHGA.

| | 19 | 20 | 21 | 22 |
|---|---|---|---|---|
| Ketal | E-DHGA-DM | E-DHGA-DM | E-DHGA-neo | E-DHGA-tfe |
| Formula of Ir complex | III-F | III-F | III-F | III-F |
| Configuration of chiral Ir complex at * | (S) | (S) | (S) | (S) |
| Amount of chiral Ir complex [mol-%] | 0.25 | 0.5 | 0.25 | 0.5 |
| Solvent[1] | DCM | TFE | DCM | TFE |

TABLE 6c-continued

Asymmetric hydrogenation of different ketals of E-DHGA.

|  | 19 | 20 | 21 | 22 |
|---|---|---|---|---|
| Hydrogenated ketal | R-THGA-DM | R-THGA-DM | R-THGA-neo | R-THGA-tfe |
| Conversion [%] | >99 | >99 | >99 | >99 |
| Isomer-Distribution[2,3] | | | | |
| (R) [%] | 93.8 | 94.3 | 94.7 | 94.8 |
| (S) [%] | 6.2 | 5.7 | 5.3 | 5.2 |

[1]TFE = 2,2,2-trifluoroethanol; DCM = dichloromethane
[2](R) stands for the R-isomer, (S) stands for the S-isomer of the corresponding ketal of 6,10-dimethylundecan-2-one
[3]is determined as ketone after hydrolysis of the ketal

TABLE 6d

Asymmetric hydrogenation of different ketals of Z-DHGA.

|  | 23 | 24 | 25 | 26 |
|---|---|---|---|---|
| Ketal | Z-DHGA-DM | Z-DHGA-DM | Z-DHGA-neo | Z-DHGA-neo |
| Formula of Ir complex | III-F | III-F | III-F | III-F |
| Configuration of chiral Ir complex at * | (R) | (R) | (R) | (R) |
| Amount of chiral Ir complex [mol-%] | 0.25 | 0.5 | 0.5 | 0.5 |
| Solvent[1] | DCM | TFE | DCM | TFE |
| Hydrogenated ketal | R-THGA-DM | R-THGA-DM | R-THGA-neo | R-THGA-neo |
| Conversion [%] | >99 | >99 | >99 | >99 |
| Isomer-Distribution[2,3] | | | | |
| (R) [%] | 99.2 | 99.4 | 97.8 | 98.0 |
| (S) [%] | 0.8 | 0.6 | 2.2 | 2.0 |

[1]TFE = 2,2,2-trifluoroethanol; DCM = dichloromethane
[2](R) stands for the R-isomer, (S) stands for the S-isomer of the corresponding ketal of 6,10-dimethylundecan-2-one
[3]is determined as ketone after hydrolysis of the ketal

TABLE 6e

Asymmetric hydrogenation of different ketals of E,E-FA.
Conditions: 0.5 mmol ketal, 4 g solvent, pressure p(H₂) = 30 bar, 16 h stirring at room temperature

|  | 27 | 28 | 29 |
|---|---|---|---|
| Ketal to be hydrogenated | E,E-FA-DM | E,E-FA-DM | E,E-FA-tfe |
| Formula of Ir-complex | III-F | III-F | III-F |
| Configuration of chiral Ir-complex at * | (S) | (S) | (S) |
| Amount of chiral Ir complex [mol-%] | 0.25 | 0.25 | 0.5 |
| Solvent[1] | DCM | TFE | TFE |
| Conversion [%] | >99 | >99 | >99 |
| Isomer-Distribution[2,3] | | | |
| (RR) [%] | 97.1 | 96.4 | 96.5 |
| ((SS) + (RS)) [%] | 1.3 | 1.3 | 1.5 |
| (SR) [%] | 1.6 | 2.3 | 2.0 |

[1]TFE = 2,2,2-trifluoroethanol; DCM = dichloromethane
[2](SS) stands for the (6S,10S)-isomer, (RR) stands for the (6R,10R)-isomer, (SR) stands for the (6S,10R)-isomer, (RS) stands for the (6R,10S)-isomer of the corresponding ketal of 6,10,14-trimethylpentadecan-2-one
[3]is determined as ketone after hydrolysis of the ketal

TABLE 6f

Asymmetric hydrogenation of different ketals of E,E-DHFA and ZZ-DHFA. Conditions: 0.5 mmol ketal, 4 g solvent, pressure p(H₂) = 30 bar, 16 h stirring at room temperature

|  | 30 | 31 | 32 | 33 | 34 |
|---|---|---|---|---|---|
| Ketal to be hydrogenated | E,E-DHFA-DM | E,E-DHFA-neo | E,E-DHFA-neo | Z,Z-DHFA-DM | Z,Z-DHFA-DM |
| Formula of Ir-complex | III-F | III-F | III-F | III-F | III-F |
| Configuration of chiral Ir-complex at * | (S) | (S) | (S) | (R) | (R) |
| Amount of chiral Ir complex [mol-%] | 0.25 | 0.5 | 0.5 | 0.5 | 0.5 |
| Solvent[1] | DCM | DCM | TFE | DCM | TFE |
| Conversion [%] | >99 | >99 | >99 | >99 | >99 |
| Isomer-Distribution[2,3] | | | | | |
| (RR) [%] | 93.0 | 94.5 | 92.8 | 96.8 | 96.8 |
| ((SS) + (RS)) [%] | 5.5 | 5.5 | 5.9 | 1.4 | 1.6 |
| (SR) [%] | 1.5 | 0.0 | 1.3 | 1.7 | 1.6 |

[1]TFE = 2,2,2-trifluoroethanol; DCM = dichloromethane
[2](SS) stands for the (6S,10S)-isomer, (RR) stands for the (6R,10R)-isomer, (SR) stands for the (6S,10R)-isomer, (RS) stands for the (6R,10S)-isomer of the corresponding ketal of 6,10,14-trimethylpentadecan-2-one
[3]is determined as ketone after hydrolysis of the ketal

TABLE 6g

Asymmetric hydrogenation of different ketals of (R,E)-6,10,14-trimethylpentadec-5-en-2-one leading to (6R,10R)-6,10,14-trimethylpentadecan-2-one. Conditions: 0.5 mmol ketal, 4 g solvent, pressure p(H₂) = 30 bar, 16 h stirring at room temperature

|  | 35 | 36 | 37 |
|---|---|---|---|
| Ketal to be hydrogenated | R-E-THFA-DM | R-E-THFA-DM | R-E-THFA-neo |
| Formula of Ir complex | III-F | III-F | III-F |
| Configuration of chiral Ir complex at * | (S) | (S) | (S) |
| Amount of chiral Ir complex [mol-%] | 0.25 | 0.25 | 0.5 |
| Solvent[1] | DCM | TFE | DCM |
| Conversion [%] | >99 | >99 | >99 |
| Isomer-Distribution[2,3] | | | |
| (RR) [%] | 90.0 | 88.7 | 90.6 |
| ((SS) + (RS)) [%] | 8.0 | 8.7 | 9.4 |
| (SR) [%] | 2.0 | 2.6 | 0.0 |

[1]TFE = 2,2,2-trifluoroethanol; DCM = dichloromethane
[2](SS) stands for the (6S,10S)-isomer, (RR) stands for the (6R,10R)-isomer, (SR) stands for the (6S,10R)-isomer, (RS) stands for the (6R,10S)-isomer of the corresponding ketal of 6,10,14-trimethyl-pentadecan-2-one
[3]is determined as ketone after hydrolysis of the ketal

TABLE 6h

Asymmetric hydrogenation of different ketals of (R,Z)-6,10,14-trimethylpentadec-5-en-2-one leading to (6R,10R)-6,10,14-trimethyl-pentadecan-2-one. Conditions: 0.5 mmol ketal, 4 g solvent, pressure p(H₂) = 30 bar, 16 h stirring at room temperature

|  | 38 | 39 | 40 | 41 |
|---|---|---|---|---|
| Ketal to be hydrogenated | R-Z-THFA-DM | R-Z-THFA-DM | R-Z-THFA-neo | R-Z-THFA-neo |
| Formula of Ir complex | III-F | III-F | III-F | III-F |
| Configuration of chiral Ir complex at * | (R) | (R) | (R) | (R) |
| Amount of chiral Ir complex [mol-%] | 0.5 | 0.5 | 0.5 | 0.5 |

TABLE 6h-continued

Asymmetric hydrogenation of different ketals of (R,Z)-6,10,14-tri-methylpentadec-5-en-2-one leading to (6R,10R)-6,10,14-trimethyl-pentadecan-2-one. Conditions: 0.5 mmol ketal, 4 g solvent, pressure $p(H_2)$ = 30 bar, 16 h stirring at room temperature

|  | 38 | 39 | 40 | 41 |
|---|---|---|---|---|
| Solvent[1] | DCM | TFE | DCM | TFE |
| Conversion [%] | >99 | >99 | >99 | >99 |
| Isomer-Distribution[2,3] | | | | |
| (RR) [%] | 86.3 | 87.4 | 86.8 | 85.5 |
| ((SS) + (RS)) [%] | 8.2 | 7.5 | 8.2 | 9.4 |
| (SR) [%] | 5.5 | 5.1 | 5.0 | 5.1 |

[1]TFE = 2,2,2-trifluoroethanol; DCM = dichloromethane

[2](SS) stands for the (6S,10S)-isomer, (RR) stands for the (6R,10R)-isomer, (SR) stands for the (6S,10R)-isomer, (RS) stands for the (6R,10S)-isomer of the corresponding ketal of 6,10,14-trimethyl-pentadecan-2-one

[3]is determined as ketone after hydrolysis of the ketal.

TABLE 6i

Hydrogenation of E-DHGA and of E-DHGA-en. The effect of ketalization.

|  | 42 | 43 |
|---|---|---|
| Ketone to be hydrogenated | E-DHGA | |
| Ketal to be hydrogenated | | E-DHGA-en |
| Formula of Ir complex | III-F | III-F |
| Configuration of chiral Ir complex at * | (R) | (R) |
| conc.[1] [mol/L] | 1.0 | 0.9 |
| pH$_2$ [bar] | 50 | 50 |
| t [h] | 20 | 20 |
| S/C | 10'000 | 10'000 |
| Solvent | TFE | TFE |
| Assay yield [area-%] | 1 | 97 |
| Isomer-Distribution[3,4] | | |
| (R) [%] | n.d.[2] | 2.2 |
| (S) [%] | n.d.[2] | 97.8 |

[1]conc. = mol ketone or ketal/L solvent

[2]n.d. = not determined (due to low assay yield)

[3](R) stands for the R-isomer, (S) stands for the S-isomer of the ethylene glycol ketal of 6,10-dimethylundecan-2-one

[4]is determined as ketone after hydrolysis of the ketal

TABLE 6j

Hydrogenation of Z-DHGA and of Z-DHGA-en and of Z-DHGA-neo. The effect of ketalization.

|  | 44 | 45 | 46 | 47 |
|---|---|---|---|---|
| Ketone to be hydrogenated | Z-DHGA | | | |
| Ketal to be hydrogenated | | Z-DHGA-en | Z-DHGA-en | Z-DHGA-neo |
| Formula of Ir complex | III-F | III-F | III-F | III-F |
| Configuration of chiral Ir complex at * | (R) | (R) | (R) | (R) |
| conc.[1] [mol/L] | 1.0 | 0.2 | 0.2 | 0.2 |
| pH$_2$ [bar] | 50 | 25 | 25 | 25 |
| t [h] | 20 | 15 | 15 | 24 |
| S/C | 5'000 | 5'000 | 10'000 | 10'000 |
| Solvent | DCM | DCM | DCM | DCM |
| Assay yield [area-%] | 1 | 84 | 39 | 22 |
| Isomer-Distribution[3,4] | | | | |
| (R) [%] | n.d.[2] | 98.6 | 98.4 | 95 |
| (S) [%] | n.d.[2] | 1.4 | 1.6 | 5 |

[1]conc. = mol ketone or ketal/L solvent (DCM = dichloromethane)

[2]n.d. = not determined (due to low assay yield)

[3](R) stands for the R-isomer, (S) stands for the S-isomer of the ethylene glycol ketal of 6,10-dimethylundecan-2-one

[4]is determined as ketone after hydrolysis of the ketal.

TABLE 6k

Hydrogenation of EE-FA and of FA-en. The effect of ketalization.

|  | 48 | 49 | 50 | 51 | 52 | 53 | 54 |
|---|---|---|---|---|---|---|---|
| Ketone to be hydrogenated | EE-FA | EE-FA | | | | EE-FA | |
| Ketal to be hydrogenated | | | EE-FA-en | EE-FA-en | EE-FA-en | | EE-FA-en |
| Formula of Ir complex | III-F | III-F | III-F | III-F | III-F | III-F | III-F |
| Configuration of chiral Ir complex at * | (R) | (R) | (R) | (R) | (R) | (R) | (R) |
| conc.[1] [mol/L] | 0.2 | 0.2 | 0.2 | 0.2 | 0.2 | 0.2 | 0.2 |
| pH$_2$ [bar] | 50 | 25 | 25 | 25 | 25 | 25 | 50 |
| t [h] | 21 | 21 | 24 | 24 | 24 | 24 | 20 |
| S/C | 500 | 1'000 | 2'000 | 5'000 | 10'000 | 2'000 | 2'000 |
| Solvent | DCM | DCM | DCM | DCM | DCM | TFE | TFE |
| Assay yield [area-%] | 96 | 27 | 98 | 37 | 1 | 56 | 97 |

TABLE 6k-continued

Hydrogenation of EE-FA and of FA-en. The effect of ketalization.

|  | 48 | 49 | 50 | 51 | 52 | 53 | 54 |
|---|---|---|---|---|---|---|---|
| Isomer-Distribution[3,4] | | | | | | | |
| (SS) [%] | n.d.[2] | n.d.[2] | 96.3 | 96.3 | n.d.[2] | 94.4 | 96.5 |
| ((RR) + (SR)) [%] | n.d.[2] | n.d.[2] | 1.5 | 1.6 | n.d.[2] | 1.7 | 1.7 |
| (RS) [%] | n.d.[2] | n.d.[2] | 2.2 | 2.1 | n.d.[2] | 3.9 | 1.8 |

[1]conc. = mol ketone or ketal/L solvent (DCM = dichloromethane)
[2]n.d. = not determined
[3](SS) stands for the (6S,10S)-isomer, (RR) stands for the (6R,10R)-isomer, (SR) stands for the (6S,10R)-isomer, (RS) stands for the (6R,10S)-isomer of the ethylene glycol ketal of 6,10,14-trimethyl-pentadecan-2-one
[4]is determined as ketone after hydrolysis of the ketal.

(R)-2,2-dimethoxy-6,10-dimethylundecane (R-THGA-DM)

$^1$H NMR (300 MHz, CDCl$_3$): δ 0.848 (d, J=6.6 Hz, 3H) superimposed by 0.852 (d, J=6.6 Hz, 6H), 1.01-1.41 (m, 11H) superimposed by 1.25 (s, 3H), 1.44-1.61 (m, 3H), 3.16 (s, 6H) ppm.

$^{13}$C NMR (75 MHz, CDCl$_3$): δ 14.1 (1C), 19.6 (1C), 20.9 (1C), 21.7 (1C), 22.6 (1C), 22.7 (1C), 24.8 (1C), 27.9 (1C), 32.7 (1C), 36.8 (1C), 37.2 (1C), 37.4 (1C), 39.3 (1C), 47.9 (1C), 101.7 (1C) ppm.

MS (EI, m/z): No GC-MS was obtained due to decomposition on the column.

IR (cm$^{-1}$): 2951 (s), 2927 (m), 2870 (m), 2828 (m), 1723 (w), 1462 (m), 1377 (m), 1309 (w), 1256 (m), 1215 (m), 1194 (m), 1172 (m), 1111 (m), 1089 (m), 1053 (s), 972 (w), 934 (w), 920 (w), 855 (m), 815 (m), 736 (w), 618 (w).

(R)-2-(4,8-dimethylnonyl)-2,5,5-trimethyl-1,3-dioxane (R-THGA-neo)

$^1$H NMR (300 MHz, CDCl$_3$): δ 0.87 (d, J=6.6 Hz, 9H), 0.91 (s, 3H), 1.01 (s, 3H), 1.04-1.61 (m, 12H) superimposed by 1.36 (s, 3H), 1.61-1.74 (m, 2H), AB signal (δ$_A$=3.44, δ$_B$=3.54, J$_{AB}$=11.7 Hz, 4H) ppm.

$^{13}$C NMR (75 MHz, CDCl$_3$): δ 19.7 (1C), 20.4 (1C), 21.0 (1C), 22.56 (1C), 22.61 (1C), 22.71 (1C), 22.77 (1C), 24.8 (1C), 28.0 (1C), 30.0 (1C), 32.8 (1C), 37.3 (1C), 37.4 (1C), 38.2 (1C), 39.3 (1C), 70.3 (2C), 99.1 (1C) ppm.

MS (EI, m/z): 269 [(M-CH$_3$)$^+$, 65], 199 (8), 129 (100), 109 (8), 69 (32), 55 (10), 43 (25).

IR (cm$^{-1}$): 2953 (s), 2925 (m), 2868 (m), 1722 (w), 1464 (m), 1394 (m), 1371 (m), 1316 (w), 1258 (m), 1212 (m), 1161 (m), 1141 (m), 1111 (s), 1095 (s), 1043 (m), 1020 (m), 951 (m), 925 (m), 907 (m) 870 (m), 855 (m), 801 (m), 792 (m), 737 (m), 677 (w), 667 (w).

(R)-6,10-dimethyl-2,2-bis(2,2,2-trifluoroethoxy)undecane (R-THGA-tfe)

$^1$H NMR (300 MHz, CDCl$_3$): δ 0.88 (d, J=6.6 Hz, 6H), 0.87 (d, J=6.4 Hz, 3H), 1.03-1.23 (m, 5H), 1.39 (s, 3H), 1.38-1.40 (m, 6H), 1.46-1.71 (m, 3H), 3.73-3.94 (m, 4H).

$^{13}$C NMR (75 MHz, CDCl$_3$): δ 19.5 (1C), 21.39 (1C), 21.47 (1C), 22.58 (1C), 22.68 (1C), 24.7 (1C), 28.0 (1C), 32.6 (1C), 37.0 (1C), 37.19 (1C), 37.23 (1C), 39.3 (1C), 59.2 (q, $^2J_{C,F}$=32.5 Hz, 2C), 103.6 (1C), 124.1 (q, $^1J_{C,F}$=279.0 Hz, 2C).

MS (EI, m/z): 365 [(M-CH$_3$)$^+$, 1], 281 (2), 225 [(CF$_3$CH$_2$O)$_2$C—CH$_3$)$^+$, 100], 153 (8), 140 (6), 83 (CF$_3$CH$_2$$^+$, 6), 43 (7).

IR (cm$^{-1}$): 2955 (w), 2929 (w), 2872 (w), 1463 (w), 1419 (w), 1385 (w), 1281 (s), 1216 (w), 1156 (s), 1122 (m), 1082 (s), 972 (m), 892 (m), 861 (w), 737 (w), 679 (w), 663 (m).

(6R,10R)-2,2-dimethoxy-6,10,14-trimethylpentadecane (RR18-DM)

$^1$H NMR (300 MHz, CDCl$_3$): δ 0.83-0.89 (m, 12H), 0.98-1.45 (m, 21H), 1.46-1.65 (m, 3H), 3.18 (s, 6H).

$^{13}$C NMR (75 MHz, CDCl$_3$): δ 19.68 (1C), 19.73 (1C), 21.0 (1C), 21.7 (1C), 22.6 (1C), 22.7 (1C), 24.5 (1C), 24.8 (1C), 28.0 (1C), 32.72 (1C), 32.78 (1C), 36.8 (1C), 37.28 (1C), 37.33 (1C), 37.36 (1C), 37.41 (1C), 39.4 (1C), 48.0 (2C), 101.7 (1C) ppm.

IR (cm$^{-1}$): 2951 (s), 2926 (s), 2869 (s), 2828 (m), 1734 (w), 1723 (w), 1216 (w), 1463 (s), 1377 (s), 1308 (w), 1255 (m), 1215 (m), 1172 (s), 1105 (s), 1090 (s), 1054 (s), 971 (w), 933 (w), 860 (s), 815 (m), 736 (w) 618 (w).

2,5,5-trimethyl-2-((4R,8R)-4,8,12-trimethyltridecyl)-1,3-dioxane (RR18-neo)

$^1$H NMR (300 MHz, CDCl$_3$): δ 0.78-0.95 (m, 15H), 0.95-1.61 (m, 19H), superimposed by 1.01 (s, 3H), 1.36 (s, 3H), 1.63-1.74 (m, 2H), AB signal (δ$_A$=3.44, δ$_B$=3.55, J$_{AB}$=11.7 Hz, 4H) ppm.

$^{13}$C NMR (75 MHz, CDCl$_3$): δ 19.72 (1C), 19.74 (1C), 20.4 (1C), 20.9 (1C), 22.56 (1C), 22.62 (1C), 22.72 (1C), 22.77 (1C), 24.5 (1C), 24.8 (1C), 28.0 (1C), 30.0 (1C), 32.8 (1C), 32.8 (1C), 37.28 (1C), 37.35 (1C), 37.42 (2C), 38.2 (1C), 39.4 (1C), 70.3 (2C), 99.1 (1C) ppm.

MS (EI, m/z): 339 [(M-CH$_3$)$^+$, 83], 269 (5), 129 (100), 69 (21), 43 (18).

IR (cm$^{-1}$): 2952 (s), 2925 (s), 2867 (m), 1463 (m), 1394 (m), 1372 (m), 1258 (m), 1211 (m), 1189 (w), 1141 (w), 1100 (s), 1043 (m), 1020 (m), 951 (w), 925 (w), 907 (m), 858 (m), 792 (w), 737 (w), 677 (w).

(6R,10R)-6,10,14-trimethyl-2,2-bis(2,2,2-trifluoroethoxy)pentadecane (RR18-tfe)

$^1$H NMR (600 MHz, CDCl$_3$): δ 0.86 (d, J=6.6 Hz, 3H), 0.879 (d, J=6.6 Hz, 3H), 0.882 (d, J=6.6 Hz, 3H), 0.884 (d, J=6.6 Hz, 3H), 1.03-1.46 (m, 18H), superimposed by 1.40 (s, 3H), 1.54 (qqt, J=6.6, 6.6, 6.6 Hz, 1H), 1.60-1.70 (m, 2H), 3.77-3.90 (m, 4H) ppm.

$^{13}$C NMR (151 MHz, CDCl$_3$): δ 19.6 (1C), 19.7 (1C), 21.4 (1C), 21.5 (1C), 22.6 (1C), 22.7 (1C), 24.5 (1C), 24.8 (1C), 28.0 (1C), 32.6 (1C), 32.8 (1C), 37.0 (1C), 37.24 (1C), 37.30 (1C), 37.34 (1C), 37.43 (1C), 39.4 (1C), 59.2 (q, $^2J_{C,F}$=35.0 Hz, 2C), 103.6 (1C), 124.0 (q, $^1J_{C,F}$=277.0 Hz, 2C) ppm.

MS (EI, m/z): 435 [(M-CH$_3$)$^+$, 1], 351 (1), 250 (1), 225 [(CF$_3$CH$_2$O)$_2$C—CH$_3$)$^+$, 100], 153 (7), 140 (5), 83 (CF$_3$CH$_2$+, 3), 43 (6).

IR (cm$^{-1}$): 2954 (m), 2927 (m), 2871 (w), 1463 (w), 1419 (w), 1384 (w), 1281 (s), 1215 (w), 1157 (s), 1123 (m), 1082 (s), 972 (s), 892 (m), 861 (w), 737 (w), 679 (w), 663 (m).

Experiment E6

Hydrolysis of Hydrogenated Ketals

After the asymmetric hydrogenation of ketals as shown in experiment E5, the hydrogenated ketals obtained were hydrolysed to (R)-6,10-dimethylundecan-2-one or (6R,10R)-6,10,14-trimethylpentadecan-2-one, respectively.
Method 1—Neopentyl Ketals, Dimethyl Ketals from Asymmetric Hydrogenation Reactions in Dichloromethane A sample of the reaction mixture from the asymmetric hydrogenation reaction (1-2 ml) was stirred with an equal volume of 1 M aqueous solution of hydrochloric acid at room temperature for 1 hour. Dichloromethane (2 ml) was added and the layers were separated. The aqueous layer was washed with dichloromethane (2 ml) twice. The combined organic layers were evaporated under reduced pressure to yield the ketone as a colourless to pale-yellow oil. The crude ketone was then analysed for purity and isomer ratio.
Method 2—Ethylene Glycol Ketals, bis(trifluoroethanol) Ketals and Dimethyl Ketals from Asymmetric Hydrogenation Reactions in Trifluoroethanol A sample of the reaction mixture from the asymmetric hydrogenation reaction (1-2 ml) was stirred with 0.5 ml of a solution of 9:1:0.2 (by volume) methanol:water:trifluoroacetic acid at 40° C. for 1 hour. Dichloromethane (2 ml) and water (2 ml) were added and the layers were separated. The aqueous layer was washed with dichloromethane (2 ml) twice. The combined organic layers were evaporated under reduced pressure to yield the ketone as a colourless to pale-yellow oil. The crude ketone was then analysed for purity and isomer ratio.

Experiment E7

Preparation of Additives

The additives tetraisopropyl orthotitanate (Ti(OiPr)$_4$), yttrium triflate (Y(OTf)$_3$), sodium tetrakis[3,5-bis(trifluoromethyl)phenyl]borate (NaBAr$_F$) and trimethylaluminum (TMA) are commercially available and were used as received.
TMA/TFE: A 2 M TMA (TMA: trimethylaluminum (Al(CH$_3$)$_3$)) solution in heptane (1 mmol) was quenched with TFE (3.1 mmol), leading to small excess of free TFE. This additive is used after being been freshly prepared.

Experiment E8

Asymmetric Hydrogenations of Ketones in the Presence of Additives (Steps c1/c2)

An autoclave vessel was charged under nitrogen with chiral iridium complex of formula (III-F) of the R configuration at the chiral centre marked by *, Z-DHGA or ZZ-FA (conc.) as indicated in tables 7a or 7b, solvent as indicated in tables 7a or 7b and an additive as indicated in tables 7a or 7b. The reaction vessel was closed and pressurized with molecular hydrogen to the pressure (pH$_2$) of 50 bar. The reaction mixture was stirred at room temperature for 20 hours under hydrogen. Then the pressure was released and the assay yield and the stereoisomer distribution of the fully hydrogenated product was determined. The catalyst loading (S/C) is defined as mmol ketone ("substrate")/mmol chiral iridium complex.

TABLE 7a

Hydrogenation of Z-DHGA. The effect of additives.

|  | 55 | 56 |
| --- | --- | --- |
| Ketone to be hydrogenated | Z-DHGA | Z-DHGA |
| conc.[1] [mol/L] | 1.0 | 0.8 |
| S/C | 5'000 | 5'000 |
| Solvent | DCM | DCM |
| Additive | — | TMA/TFE |
| Additive concentration [mol-%][2] | — | 5 |
| Assay yield [area-%] | 1 | 40 |
| (R)-6,10-dimethylundecan-2-one [%] | n.d.[3] | 98.3 |
| (S)-6,10-dimethylundecan-2-one [%] | n.d.[3] | 1.7 |

[1]conc. = mol ketone/L solvent
[2]relative to the molar amount of Z-DHGA.
[3]n.d. = not determined (due to low assay yield).

TABLE 7b

Hydrogenation of ZZ-FA (0.2M in 2,2,2-trifluorethanol (TFE). The effect of the additives.

|  | 57 | 58 | 59 |
| --- | --- | --- | --- |
| Ketone to be hydrogenated | ZZ-FA | ZZ-FA | ZZ-FA |
| S/C | 2000 | 2000 | 2000 |
| Solvent | TFE | TFE | TFE |
| Additive | — | Y(OTf)$_3$ | Ti(OiPr)$_4$ |
| Additive concentration [mol-%][1] | — | 0.2 | 14 |
| Assay yield [area-%] | 9 | 76 | 53 |
| Isomer-Distribution[2] |  |  |  |
| (RR) [%] | 89.9 | 92.8 | 91.8 |
| ((SS) + (RS)) [%] | 5.0 | 3.4 | 3.9 |
| (SR) [%] | 5.1 | 3.8 | 4.3 |

[1]relative to the molar amount of ZZ-FA
[2](SS) stands for the (6S,10S)-isomer, (RR) stands for the (6R,10R)-isomer, (SR) stands for the (6S,10R)-isomer, (RS) stands for the (6R,10S)-isomer of 6,10,14-trimethylpentadecan-2-one.

Experiment E9

Asymmetric Hydrogenations of Ketals in the Presence of Additives (Steps c1/c2)

An autoclave vessel was charged under nitrogen with chiral iridium complex of formula (III-F) of the R configuration at the chiral centre marked by *, the ketal Z-DHGA-en or Z-DHGA-neo in a concentration of 0.2 mol ketal/L solvent (DCM or TFE) and an additive as indicated in table 8. The reactive vessel was closed and pressurized with molecular hydrogen to the pressure 50 bar and stirred at room temperature during 20 hours under hydrogen. Then the pressure was released and the assay yield and the stereoisomer distribution of the fully hydrogenated product were determined. In case of ketals the assay yield and the stereoisomer distribution have been determined after the hydrolysis of the ketal by acid as indicated in experiment E6. The catalyst loading (S/C) is defined as mmol ketal ("substrate")/mmol chiral iridium complex.

TABLE 8

Hydrogenation of different ketals of Z-DHGA at pressure of molecular hydrogen (pH$_2$) of 50 bar and stirring at room temperature during 20 hours. The effect of the additives.

| | 60 | 61 | 62 | 63 | 64 | 65 |
|---|---|---|---|---|---|---|
| Ketal to be hydrogenated | Z-DHGA-en | Z-DHGA-en | Z-DHGA-en | Z-DHGA-en | Z-DHGA-neo | Z-DHGA-neo |
| conc.[1] [mol/L] | 0.2 | 0.2 | 0.2 | 0.2 | 0.2 | 0.2 |
| S/C | 5'000 | 10'000 | 10'000 | 52'000 | 20'000 | 20'000 |
| Solvent[3] | DCM | DCM | TFE | TFE | TFE | TFE |
| Additive | — | — | NaBAr$_F$ | TMA[4] | — | TMA[4] |
| Additive concentration [mol-%][2] | — | — | 0.014 | 100 | — | 10 |
| Assay yield [area-%] | 84 | 39 | 46 | 93 | 4 | 63 |
| Isomer-Distribution[5,6] | | | | | | |
| (R) [%] | 98.6 | 98.4 | 97.5 | 98.1 | 85.4 | 98.8 |
| (S) [%] | 1.4 | 1.6 | 2.5 | 1.9 | 14.6 | 1.2 |

[1] conc. = mol ketal/L solvent
[2] relative to the molar amount of ketal of Z-DHGA
[3] TFE = 2,2,2-trifluoroethanol; DCM = dichloromethane
[4] TMA is quenched by adding into the solvent TFE
[5] (R) stands for the R-isomer, (S) stands for the S-isomer of the corresponding ketal of 6,10-dimethylundecan-2-one
[6] is determined as ketone after hydrolysis of the ketal

The invention claimed is:

1. A process of manufacturing compound of formula (I-A) or (I-B) or an acetal or a ketal thereof from a mixture of E/Z isomers of compound of formula (I) or (II) or an acetal or a ketal thereof:

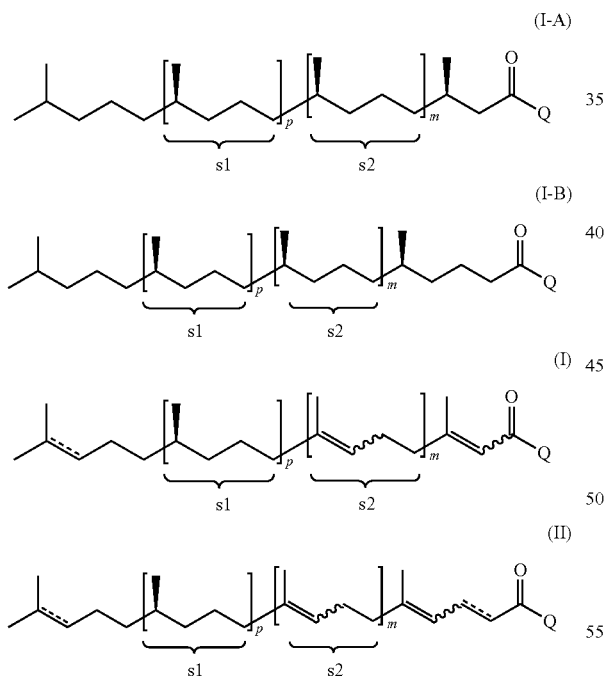

wherein Q stands for H or CH$_3$ and m and p stand independently from each other for a value of 0 to 3 with the proviso that the sum of m and p is 0 to 3, and
wherein a wavy line represents a carbon-carbon bond which is linked to the adjacent carbon-carbon double bond so as to have said carbon-carbon double bond either in the Z or in the E-configuration and where the substructures in formula (I) and (II) represented by s1 and s2 can be in any sequence; and wherein the double bond having dotted lines (════) in formula (I) or (II) represent either a single carbon-carbon bond or a double carbon-carbon bond;
and wherein
the method comprises either the steps of a1)-c1):

a1) separating an isomer having E-configuration from the mixture of E/Z isomers of compound of formula (I) or (II) or the acetal or ketal thereof;

b1) submitting the isomers having the Z-configuration of compound of formula (I) or (II) or the acetal or ketal thereof to cis/trans isomerisation and adding the isomerization product to the mixture of isomers of compound of formula (I) or (II) or the acetal or ketal thereof; and c1) submitting the separated isomer having the E-configuration of compound of formula (I) or (II) or the acetal or ketal thereof to hydrogenation by molecular hydrogen in the presence of a chiral iridium complex of formula (III) having the S-configuration at the stereogenic centre indicated by *;

or the steps of a2)-c2):

a2) separating an isomer having Z-configuration from the mixture of E/Z isomers of compound of formula (I) or (II) or the acetal or ketal thereof;

b2) submitting the isomers having the E-configuration of compound of formula (I) or (II) or the acetal or ketal thereof to cis/trans isomerisation and adding the isomerization product to the mixture of isomers of compound of formula (I) or (II) or the acetal or ketal thereof; and c2) submitting the separated isomer having the Z-configuration of compound of formula (I) or (II) or the acetal or ketal thereof to hydrogenation by molecular hydrogen in the presence of a chiral iridium complex of formula (III) having the R-configuration at the stereogenic centre indicated by *;

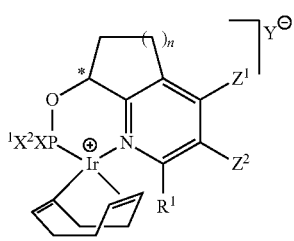

(III)

wherein n is 1, 2 or 3;

$X^1$ and $X^2$ are independently from each other hydrogen atoms, $C_{1-4}$-alkyl, $C_{5-7}$-cycloalkyl, adamantyl, phenyl, optionally substituted with one to three $C_{1-5}$-alkyl, $C_{1-4}$-alkoxy, $C_{1-4}$-perfluoroalkyl groups and/or one to five halogen atoms, benzyl, 1-naphthyl, 2-naphthyl, 2-furyl or ferrocenyl;

$Z^1$ and $Z^2$ are independently from each other hydrogen atoms, $C_{1-5}$-alkyl or $C_{1-5}$-alkoxy groups; or $Z^1$ and $Z^2$ together represent a bridging group forming a 5 to 6 membered ring;

$Y^\ominus$ is an anion selected from the group consisting of halide, $PF_6^-$, $SbF_6^-$, tetra(3,5-bis(trifluoromethyl)phenyl)borate($BAr_F^-$), $BF_4^-$, perfluorinated sulfonates, $ClO_4^-$, $Al(OC_6F_5)_4^-$, $Al(OC(CF_3)_3)_4^-$, $N(SO_2CF_3)_2^-N(SO_2C_4F_9)_2^-$ and $B(C_6F_5)_4^-$;

$R^1$ represents either phenyl or o-tolyl or m-tolyl or p-tolyl or a group of formula (IVa) or (IVb) or (IVc):

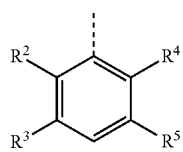

(IVa)

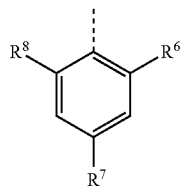

(IVb)

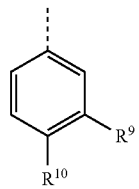

(IVc)

wherein $R^2$ and $R^3$ represent either both H or a $C_1$-$C_4$-alkyl group or a halogenated $C_1$-$C_4$-alkyl group or represent a divalent group forming together a 6-membered cycloaliphatic or an aromatic ring which optionally is substituted by halogens atoms or by $C_1$-$C_4$-alkyl groups or by $C_1$-$C_4$-alkoxy groups;

$R^4$ and $R^5$ represent either both H or a $C_1$-$C_4$-alkyl group or a halogenated $C_1$-$C_4$-alkyl group or a divalent group forming together a 6-membered cycloaliphatic or an aromatic ring which optionally is substituted by halogens atoms or by $C_1$-$C_4$-alkyl groups or by $C_1$-$C_4$-alkoxy groups;

$R^6$, $R^7$ and $R^8$ each represents a $C_1$-$C_4$-alkyl group or a halogenated $C_1$-$C_4$-alkyl group;

$R^9$ and $R^{19}$ represent either both H or a $C_1$-$C_4$-alkyl group or a halogenated $C_1$-$C_4$-alkyl group or a divalent group forming together a 6-membered cycloaliphatic or an aromatic ring which optionally is substituted by halogens atoms or by $C_1$-$C_4$-alkyl groups or by $C_1$-$C_4$-alkoxy groups; and wherein * represents a stereogenic centre of the complex of formula (III).

2. The process according to claim 1, wherein the compound of formula (I) or the compound of (II) is selected from the group consisting of 3,7-dimethyloct-6-enal, 3,7-dimethylocta-2,6-dienal, 3,7-dimethyloct-2-enal, 6,10-dimethylundeca-3,5,9-trien-2-one, 6,10-dimethylundeca-5,9-dien-2-one, 6,10-dimethylundec-5-en-2-one, 6,10-dimethylundec-3-en-2-one, 6,10-dimethylundec-3,5-diene-2-one, 6,10,14-trimethylpentadeca-5,9,13-trien-2-one, 6,10,14-trimethylpentadeca-5,9-dien-2-one, 6,10,14-trimethylpentadec-5-en-2-one, (R)-6,10,14-trimethylpentadec-5-en-2-one and E/Z-isomers thereof.

3. The process according to claim 1, wherein the compound of formula (I) or the compound of formula (II) is a compound of formula (II) selected from the group consisting of 6,10-dimethylundeca-3,5,9-trien-2-one, 6,10-dimethylundeca-5,9-dien-2-one, 6,10-dimethylundec-5-en-2-one, 6,10-dimethylundec-3-en-2-one, 6,10-dimethylundec-3,5-diene-2-one, 6,10,14-trimethylpentadeca-5,9,13-trien-2-one, 6,10,14-trimethylpentadeca-5,9-dien-2-one, 6,10,14-trimethylpentadec-5-en-2-one, (R)-6,10,14-trimethylpentadec-5-en-2-one and E/Z-isomers thereof.

4. The process according to claim 1, wherein the acetal or ketal of the compound of formula (I) or (II) is a reaction product of the compound of formula (I) or (II) with an alcohol selected from the group consisting of halogenated $C_1$-$C_8$-alkyl alcohols, ethane-1,2-diol, propane-1,2-diol, propane-1,3-diol, butane-1,4-diol, butane-1,3-diol, butane-1,2-diol, butane-2,3-diol, 2-methylpropane-1,2-diol, 2-methylpropane-1,3-diol, 2,2-dimethylpropane-1,3-diol, 1,2-dimethylpropane-1,3-diol, 3-methylpentane-2,4-diol, 2 (hydroxymethyl)cyclohexanol, benzene-1,2-diol and cyclohexane-1,2-diols.

5. The process according to claim 1, wherein $R^1$ in formula (III) of the chiral iridium complex of formula (III) is selected from the group consisting of

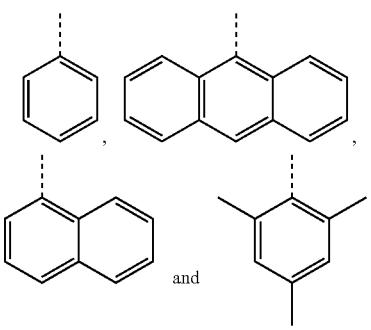

6. The process according to claim 1, wherein the chiral iridium complex is present during hydrogenation in an amount within a range from 0.0001 to 5 mol %, based on the amount of the compound of formula (I) or the compound of formula (II) or the acetal or ketal thereof.

7. The process according to claim 1, wherein the separation of isomers in step a1) or a2) is done by distillation.

8. The process according to claim 1, wherein the cis/trans isomerisation in step b1) or b2) is done in the presence of a cis/trans isomerization catalyst.

9. The process according to claim 8, wherein the cis/trans isomerization catalyst is nitrogen monoxide (NO) or an organic sulphur compound.

10. The process according to claim 8, wherein the cis/trans isomerization catalyst is a polythiol of formula (X):

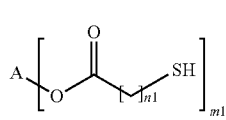
(X)

wherein n1 represents an integer from 1 to 4, and
m1 represents an integer from 2 to 8; and
A represents an aliphatic m1-valent hydrocarbon group having a molecular weight between 28 g/mol and 400 g/mol.

11. The process according to claim 1, wherein the hydrogenation is done in the presence of an additive which is selected from the group consisting of organic sulfonic acids, transition metal salts of organic sulfonic acids, metal alkoxides, aluminoxanes, alkyl aluminoxanes and $B(R)_{(3-v)}(OZ)_v$; wherein
v stands for 0, 1, 2 or 3;
R stands for F, a $C_{1-6}$-alkyl, a halogenated $C_{1-6}$-alkyl, an aryl or halogenated aryl group; and
Z stands a $C_{1-6}$-alkyl, a halogenated $C_{1-6}$-alkyl, an aryl or halogenated aryl group.

12. The process according to claim 1, wherein the anion $Y^\ominus$ is $F_3C\text{—}SO_3^-$ or $F_9C_4\text{—}SO_3^-$.

13. The process according to claim 6, wherein the chiral iridium complex is present during hydrogenation in an amount within the range from about 0.001 to about 2 mol %.

14. The process according to claim 6, wherein the chiral iridium complex is present during hydrogenation in an amount within the range from about 0.01 to about 1 mol %.

15. The process according to claim 9, wherein the cis/trans isomerization catalyst is a polythiol.

16. The process according to claim 10, wherein n1 is 2, m1 is 3 or 4 and A represents an aliphatic m1-valent hydrocarbon group having a molecular weight between 90 and 150 g/mol.

17. A ketal of formula (XX-A):

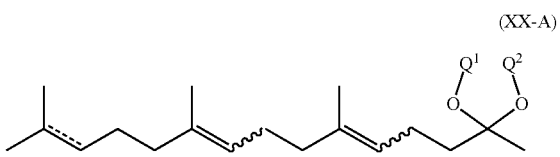
(XX-A)

wherein $Q^1$ and $Q^2$ stand either individually or both for a linear $C_1$-$C_{10}$ alkyl group, a fluorinated linear $C_1$-$C_{10}$ alkyl group or a group of the formula:

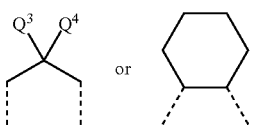

in which $Q^3$ and $Q^4$ are independently from each other hydrogen atoms, methyl groups or ethyl groups; and
wherein a wavy line represents a carbon-carbon bond which is linked to the adjacent carbon-carbon double bond so as to have said carbon-carbon double bond either in the Z or in the E-configuration; and
wherein the double bond having dotted lines ((=====)) represent either a single carbon-carbon bond or a double carbon-carbon bond.

* * * * *